(12) United States Patent
Yeung et al.

(10) Patent No.: US 9,333,041 B2
(45) Date of Patent: May 10, 2016

(54) SURGICAL MANIPULATOR

(71) Applicant: MACDONALD DETTWILER & ASSOCIATES INC, Brampton (CA)

(72) Inventors: Benny Hon Bun Yeung, Toronto (CA); Dennis Gregoris, Toronto (CA); Bronislaw Bednarz, Toronto (CA); Michael A. Gray, Toronto (CA)

(73) Assignee: MACDONALD, DETTWILER AND ASSOCIATES INC., Brampton, ON (CA)

( * ) Notice: Subject to any disclaimer, the term of this patent is extended or adjusted under 35 U.S.C. 154(b) by 0 days.

(21) Appl. No.: 13/899,300

(22) Filed: May 21, 2013

(65) Prior Publication Data
US 2014/0018821 A1 Jan. 16, 2014

Related U.S. Application Data

(63) Continuation of application No. 12/318,151, filed on Dec. 22, 2008, now Pat. No. 8,444,631, which is a continuation-in-part of application No. 11/812,094, filed on Jun. 14, 2007, now Pat. No. 8,491,603.

(60) Provisional application No. 61/008,574, filed on Dec. 21, 2007.

(51) Int. Cl.
*A61B 17/00* (2006.01)
*A61B 19/00* (2006.01)
*B25J 9/04* (2006.01)
(Continued)

(52) U.S. Cl.
CPC ............. *A61B 19/2203* (2013.01); *B25J 9/047* (2013.01); *B25J 9/104* (2013.01); *A61B 19/081* (2013.01); *A61B 19/5212* (2013.01); *A61B 2019/2223* (2013.01); *A61B 2019/2234* (2013.01);
(Continued)

(58) Field of Classification Search
CPC ............... A61B 19/22; A61B 19/2203; A61B 2019/2215; A61B 2019/2223; A61B 2019/223; A61B 2019/2242; A61B 2019/2249
USPC .......................................................... 606/1
See application file for complete search history.

(56) References Cited

U.S. PATENT DOCUMENTS 2,906,143 A 9/1959 Musser
3,397,586 A * 8/1968 Crook ............................. 74/96
(Continued)

FOREIGN PATENT DOCUMENTS

CA 1214695 12/1986
CA 2482853 11/2003
(Continued)

OTHER PUBLICATIONS

U.S. Appl. No. 11/812,094, filed Jun. 14, 2007. Non-Final Office Action dated Jul. 13, 2012.

*Primary Examiner* — William Thomson
*Assistant Examiner* — John R Downey
(74) *Attorney, Agent, or Firm* — Lynn C. Schumacher; Stephen W. Leonard; Hill & Schumacher

(57) ABSTRACT

The present invention provides a surgical manipulator including a manipulator arm, an end-effector held by the robotic arm, surgical tools held by the end-effector and manipulator joints, particularly right-angle drive devices for transmitting rotational motion in one axis to a perpendicular axis.

16 Claims, 64 Drawing Sheets

(51) Int. Cl.
*B25J 9/10* (2006.01)
*A61B 19/08* (2006.01)

(52) U.S. Cl.
CPC . *A61B2019/2242* (2013.01); *A61B 2019/2246* (2013.01); *A61B 2019/464* (2013.01)

(56) References Cited

U.S. PATENT DOCUMENTS

| | | | |
|---|---|---|---|
| 4,312,496 A | 1/1982 | Norminton | |
| 4,452,193 A | 6/1984 | Morris | |
| 4,552,505 A * | 11/1985 | Gorman | 414/735 |
| 4,565,333 A | 1/1986 | Meneian | |
| 4,579,016 A | 4/1986 | Soroka et al. | |
| 4,766,775 A | 8/1988 | Hodge | |
| 4,903,536 A | 2/1990 | Salisbury, Jr. | |
| 4,937,759 A | 6/1990 | Vold | |
| 5,046,375 A | 9/1991 | Salisbury, Jr. | |
| 5,085,556 A * | 2/1992 | Ohtomi | 414/744.3 |
| 5,086,401 A | 2/1992 | Glassman et al. | |
| 5,207,114 A | 5/1993 | Salisbury, Jr. | |
| 5,269,728 A | 12/1993 | Rogers | |
| 5,279,309 A | 1/1994 | Taylor et al. | |
| 5,299,288 A | 3/1994 | Glassman et al. | |
| 5,314,293 A * | 5/1994 | Carlisle et al. | 414/744.5 |
| 5,343,385 A | 8/1994 | Joskowicz | |
| 5,357,824 A * | 10/1994 | Hashimoto | 74/490.03 |
| 5,388,480 A | 2/1995 | Townsend | |
| 5,397,323 A | 3/1995 | Taylor et al. | |
| 5,402,801 A | 4/1995 | Taylor et al. | |
| 5,408,409 A | 4/1995 | Glassman et al. | |
| 5,410,767 A * | 5/1995 | Barud | 5/601 |
| 5,417,210 A | 5/1995 | Funda et al. | |
| 5,429,015 A | 7/1995 | Somes | |
| 5,445,166 A | 8/1995 | Taylor et al. | |
| 5,515,478 A | 5/1996 | Wang | |
| 5,553,198 A | 9/1996 | Wang et al. | |
| 5,553,509 A | 9/1996 | Somes | |
| 5,572,999 A | 11/1996 | Funda et al. | |
| 5,630,431 A | 5/1997 | Taylor et al. | |
| 5,645,520 A | 7/1997 | Nakamura et al. | |
| 5,657,429 A | 8/1997 | Wang et al. | |
| 5,695,500 A | 12/1997 | Taylor et al. | |
| 5,710,870 A | 1/1998 | Ohm et al. | |
| 5,749,362 A | 5/1998 | Funda et al. | |
| 5,754,741 A | 5/1998 | Wang et al. | |
| 5,766,126 A | 6/1998 | Anderson | |
| 5,769,092 A | 6/1998 | Williamson, Jr. | |
| 5,784,542 A | 7/1998 | Ohm et al. | |
| 5,792,135 A | 8/1998 | Madhane et al. | |
| 5,797,900 A | 8/1998 | Madhani et al. | |
| 5,807,377 A | 9/1998 | Madhani et al. | |
| 5,815,640 A | 9/1998 | Wang et al. | |
| 5,825,536 A | 10/1998 | Yasunaga et al. | |
| 5,841,950 A | 11/1998 | Wang et al. | |
| 5,878,193 A | 3/1999 | Wang et al. | |
| 5,887,121 A | 3/1999 | Funda et al. | |
| 5,897,223 A | 4/1999 | Tritchew et al. | |
| 5,907,664 A | 5/1999 | Wang et al. | |
| 5,950,629 A | 9/1999 | Taylor et al. | |
| 5,976,122 A | 11/1999 | Madhani et al. | |
| 5,976,156 A | 11/1999 | Taylor et al. | |
| 6,024,695 A | 2/2000 | Taylor et al. | |
| 6,106,511 A | 8/2000 | Jensen | |
| 6,132,368 A | 10/2000 | Cooper | |
| 6,132,441 A | 10/2000 | Grace | |
| D438,617 S | 3/2001 | Cooper et al. | |
| 6,201,984 B1 | 3/2001 | Funda et al. | |
| 6,206,903 B1 | 3/2001 | Ramans | |
| D441,076 S | 4/2001 | Cooper et al. | |
| D441,862 S | 5/2001 | Cooper et al. | |
| 6,226,566 B1 | 5/2001 | Funda et al. | |
| 6,231,526 B1 | 5/2001 | Taylor et al. | |
| 6,239,874 B1 | 5/2001 | Harwood | |
| 6,246,200 B1 * | 6/2001 | Blumenkranz et al. | 318/568.11 |
| D444,555 S | 7/2001 | Cooper et al. | |
| 6,309,397 B1 | 10/2001 | Julian et al. | |
| 6,312,435 B1 | 11/2001 | Wallace et al. | |
| 6,324,934 B1 * | 12/2001 | Monaghan | 74/490.04 |
| 6,331,181 B1 | 12/2001 | Tierney et al. | |
| 6,346,072 B1 | 2/2002 | Cooper | |
| 6,349,245 B1 | 2/2002 | Finlay | |
| 6,364,888 B1 | 4/2002 | Niemeyer et al. | |
| 6,371,952 B1 | 4/2002 | Madhani et al. | |
| 6,393,340 B2 | 5/2002 | Funda et al. | |
| 6,394,998 B1 | 5/2002 | Wallace et al. | |
| 6,400,352 B1 | 6/2002 | Bruneau et al. | |
| 6,436,107 B1 | 8/2002 | Wang et al. | |
| 6,441,577 B2 | 8/2002 | Blumenkranz | |
| 6,459,926 B1 | 10/2002 | Nowlin et al. | |
| 6,491,701 B2 | 12/2002 | Tierney et al. | |
| 6,547,782 B1 | 4/2003 | Taylor | |
| 6,554,844 B2 | 4/2003 | Lee et al. | |
| 6,594,552 B1 | 7/2003 | Nowlin et al. | |
| 6,645,196 B1 | 11/2003 | Nixon et al. | |
| 6,646,541 B1 | 11/2003 | Wang et al. | |
| 6,659,939 B2 | 12/2003 | Moll et al. | |
| 6,676,669 B2 | 1/2004 | Charles et al. | |
| 6,676,684 B1 | 1/2004 | Morley et al. | |
| 6,685,698 B2 | 2/2004 | Morley et al. | |
| 6,692,485 B1 | 2/2004 | Brock | |
| 6,699,235 B2 | 3/2004 | Wallace et al. | |
| 6,702,805 B1 | 3/2004 | Stuart | |
| 6,714,841 B1 | 3/2004 | Wright et al. | |
| 6,728,599 B2 | 4/2004 | Wang et al. | |
| 6,746,443 B1 | 6/2004 | Morley | |
| 6,766,204 B2 | 7/2004 | Niemeyer et al. | |
| 6,770,081 B1 | 8/2004 | Cooper et al. | |
| 6,783,524 B2 | 8/2004 | Anderson et al. | |
| 6,785,593 B2 | 8/2004 | Wang et al. | |
| 6,788,018 B1 | 9/2004 | Blumenkranz | |
| 6,799,088 B2 | 9/2004 | Wang et al. | |
| 6,804,581 B2 | 10/2004 | Wang et al. | |
| 6,810,281 B2 | 10/2004 | Brock et al. | |
| 6,836,703 B2 | 12/2004 | Wang et al. | |
| 6,837,883 B2 | 1/2005 | Moll et al. | |
| 6,837,892 B2 | 1/2005 | Shoham | |
| 6,839,612 B2 | 1/2005 | Sanchez et al. | |
| 6,840,938 B1 | 1/2005 | Morley et al. | |
| 6,843,793 B2 | 1/2005 | Brock et al. | |
| 6,860,878 B2 | 3/2005 | Brock | |
| 6,866,671 B2 | 3/2005 | Tierney et al. | |
| 6,871,117 B2 | 3/2005 | Wang et al. | |
| 6,879,880 B2 | 4/2005 | Nowlin et al. | |
| 6,892,112 B2 | 5/2005 | Wang et al. | |
| 6,902,560 B1 | 6/2005 | Morley et al. | |
| 6,905,460 B2 | 6/2005 | Wang et al. | |
| 6,905,491 B1 | 6/2005 | Wang et al. | |
| 6,933,695 B2 | 8/2005 | Blumenkranz | |
| 6,936,042 B2 | 8/2005 | Wallace et al. | |
| 6,951,535 B2 | 10/2005 | Ghodoussi et al. | |
| 6,969,385 B2 | 11/2005 | Moreyra | |
| 6,991,627 B2 | 1/2006 | Madhani et al. | |
| 6,994,708 B2 | 2/2006 | Manzo | |
| 7,048,745 B2 | 5/2006 | Tierney et al. | |
| 7,066,926 B2 | 6/2006 | Wallace et al. | |
| 7,074,179 B2 | 7/2006 | Wang et al. | |
| 7,083,571 B2 | 8/2006 | Wang et al. | |
| 7,087,049 B2 | 8/2006 | Nowlin, Jr. | |
| 7,107,090 B2 | 9/2006 | Salisbury, Jr. | |
| 7,121,781 B2 | 10/2006 | Sanchez | |
| 7,139,418 B2 | 11/2006 | Abovitz et al. | |
| 7,155,316 B2 | 12/2006 | Sutherland et al. | |
| 7,169,141 B2 | 1/2007 | Brock et al. | |
| 7,206,627 B2 | 4/2007 | Abovitz et al. | |
| 7,237,626 B2 | 7/2007 | Gurjar et al. | |
| 7,281,447 B2 | 10/2007 | Gosselin et al. | |
| 8,170,717 B2 | 5/2012 | Sutherland et al. | |
| 2002/0040217 A1 | 4/2002 | Jinno | |
| 2003/0167061 A1 * | 9/2003 | Schlegel et al. | 606/130 |
| 2004/0049205 A1 * | 3/2004 | Lee et al. | 606/130 |
| 2004/0142803 A1 | 7/2004 | Fitzgibbon | |
| 2004/0176751 A1 | 9/2004 | Weitzner et al. | |
| 2004/0243147 A1 * | 12/2004 | Lipow | 606/130 |

(56) References Cited

U.S. PATENT DOCUMENTS

| | | |
|---|---|---|
| 2004/0266574 A1 | 12/2004 | Jinno et al. |
| 2004/0267254 A1 | 12/2004 | Manzo |
| 2005/0021050 A1 | 1/2005 | Cooper |
| 2006/0030841 A1 | 2/2006 | Madhani et al. |
| 2006/0074406 A1* | 4/2006 | Cooper et al. .............. 606/1 |
| 2006/0142657 A1 | 6/2006 | Quaid et al. |
| 2006/0156852 A1* | 7/2006 | Haniya ................. 74/490.03 |
| 2007/0032906 A1 | 2/2007 | Sutherland et al. |
| 2008/0121064 A1* | 5/2008 | Todorov ................ 74/490.04 |

FOREIGN PATENT DOCUMENTS

| | | |
|---|---|---|
| DE | 19601857 A1 | 8/1996 |
| EP | 1815950 A1 | 8/2007 |
| JP | 07509637 | 10/1995 |
| JP | 2002102248 | 4/2002 |
| WO | 94/03113 | 2/1994 |
| WO | 03/067341 | 8/2003 |
| WO | 2007/143859 | 12/2007 |

\* cited by examiner

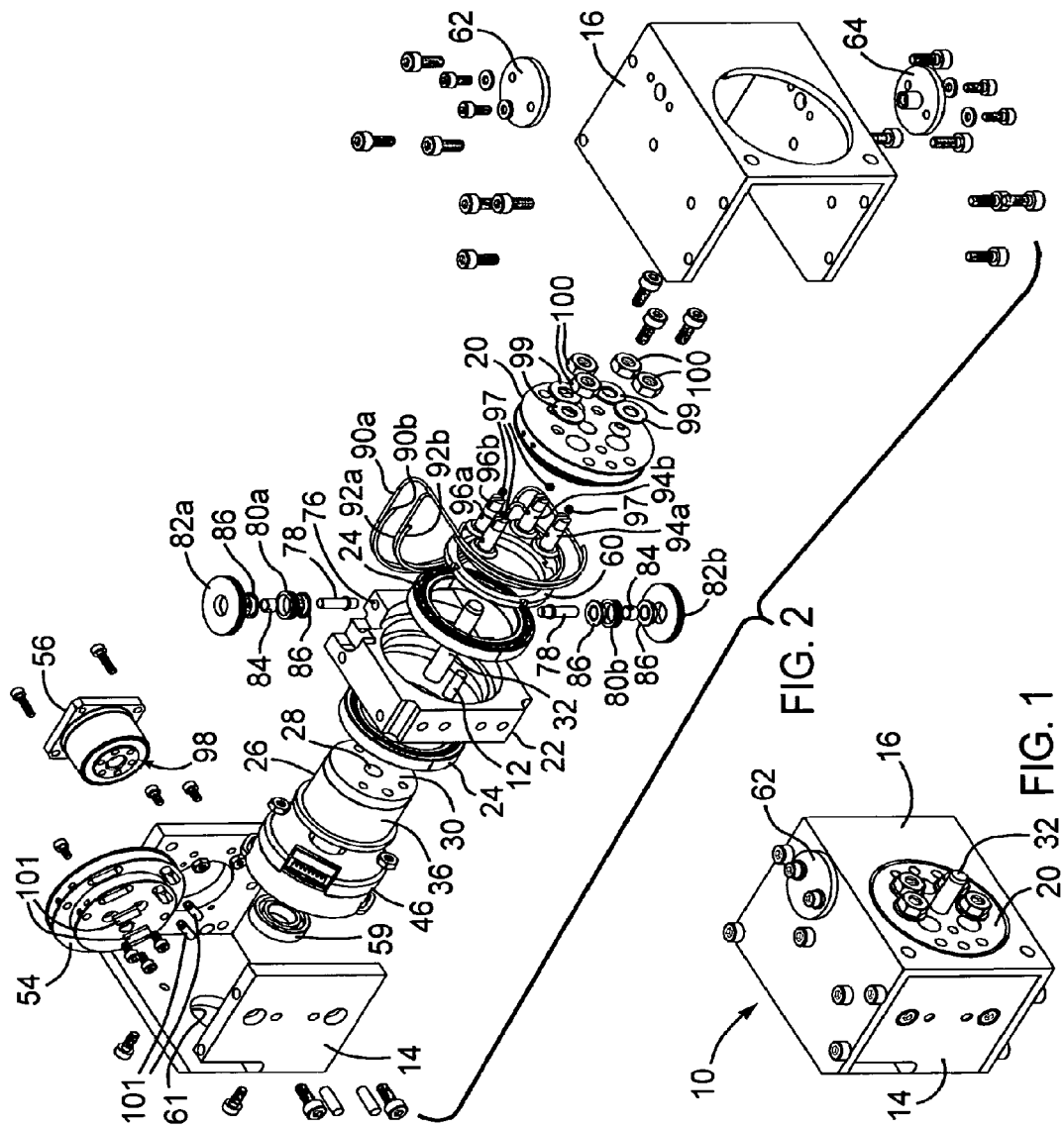

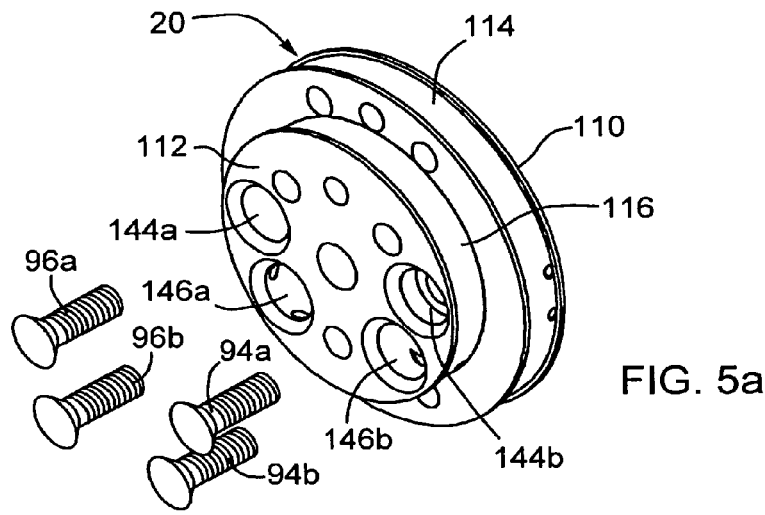
FIG. 5a
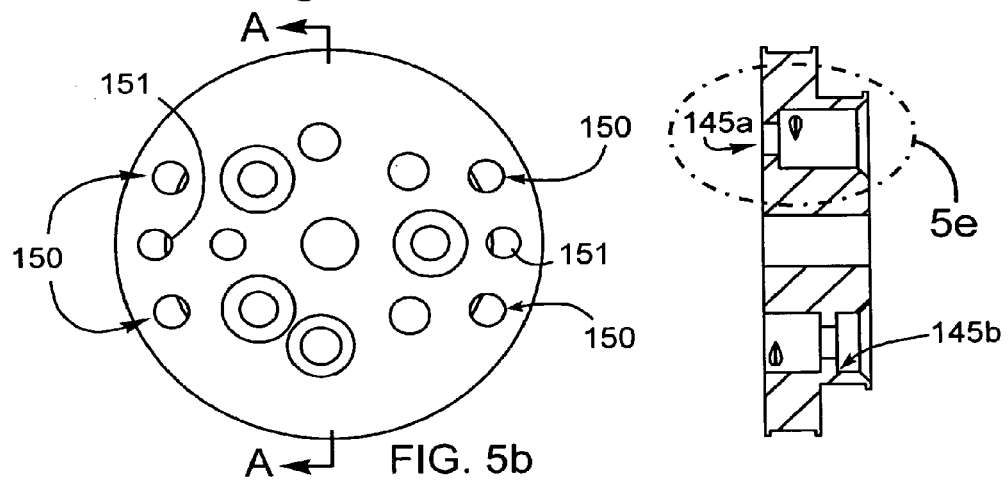
FIG. 5b
FIG. 5d
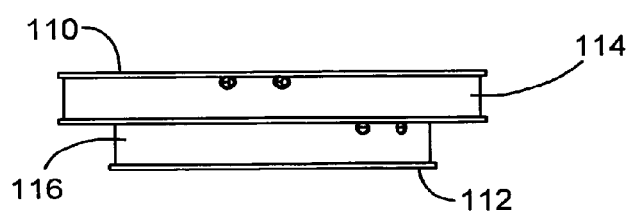
FIG. 5c

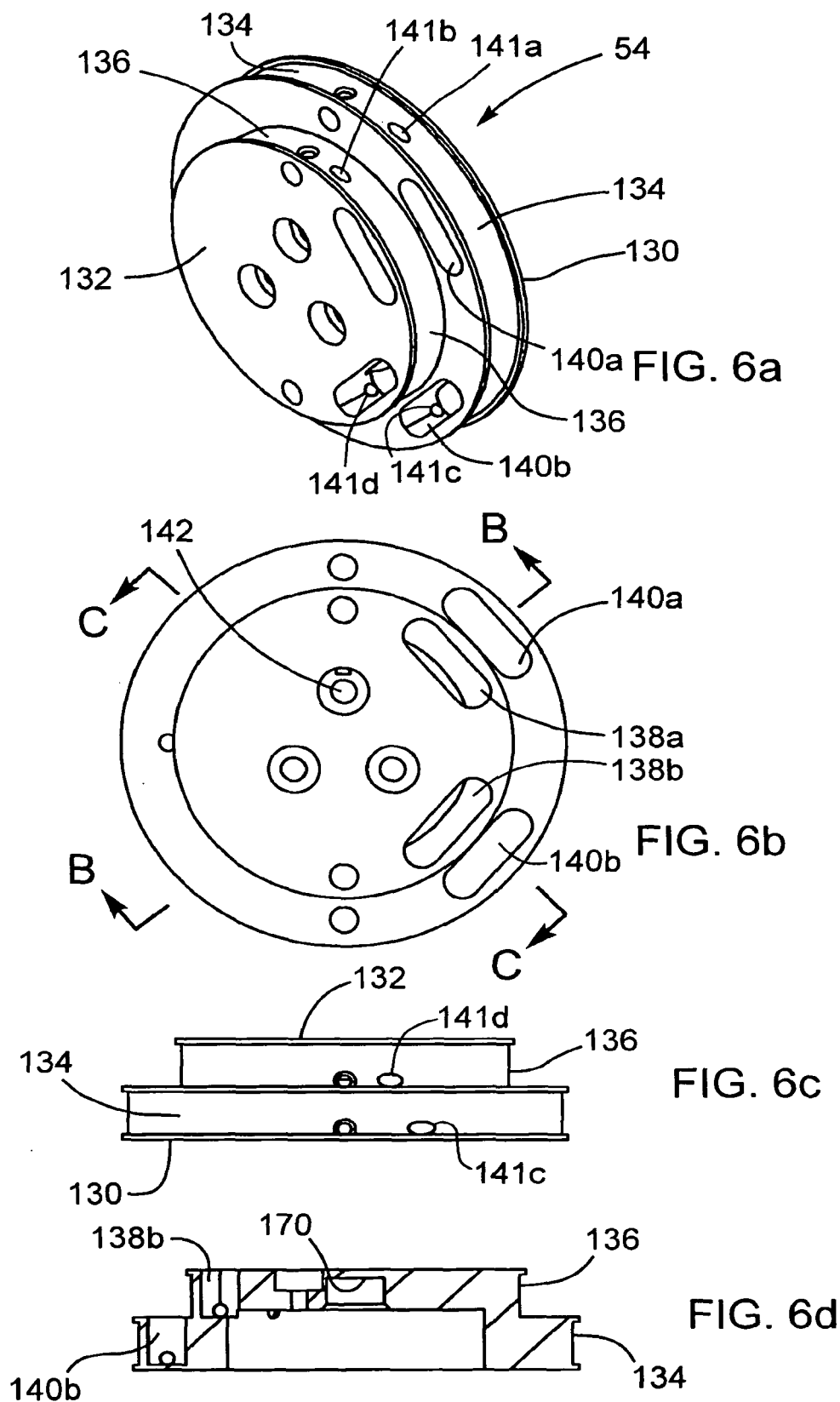

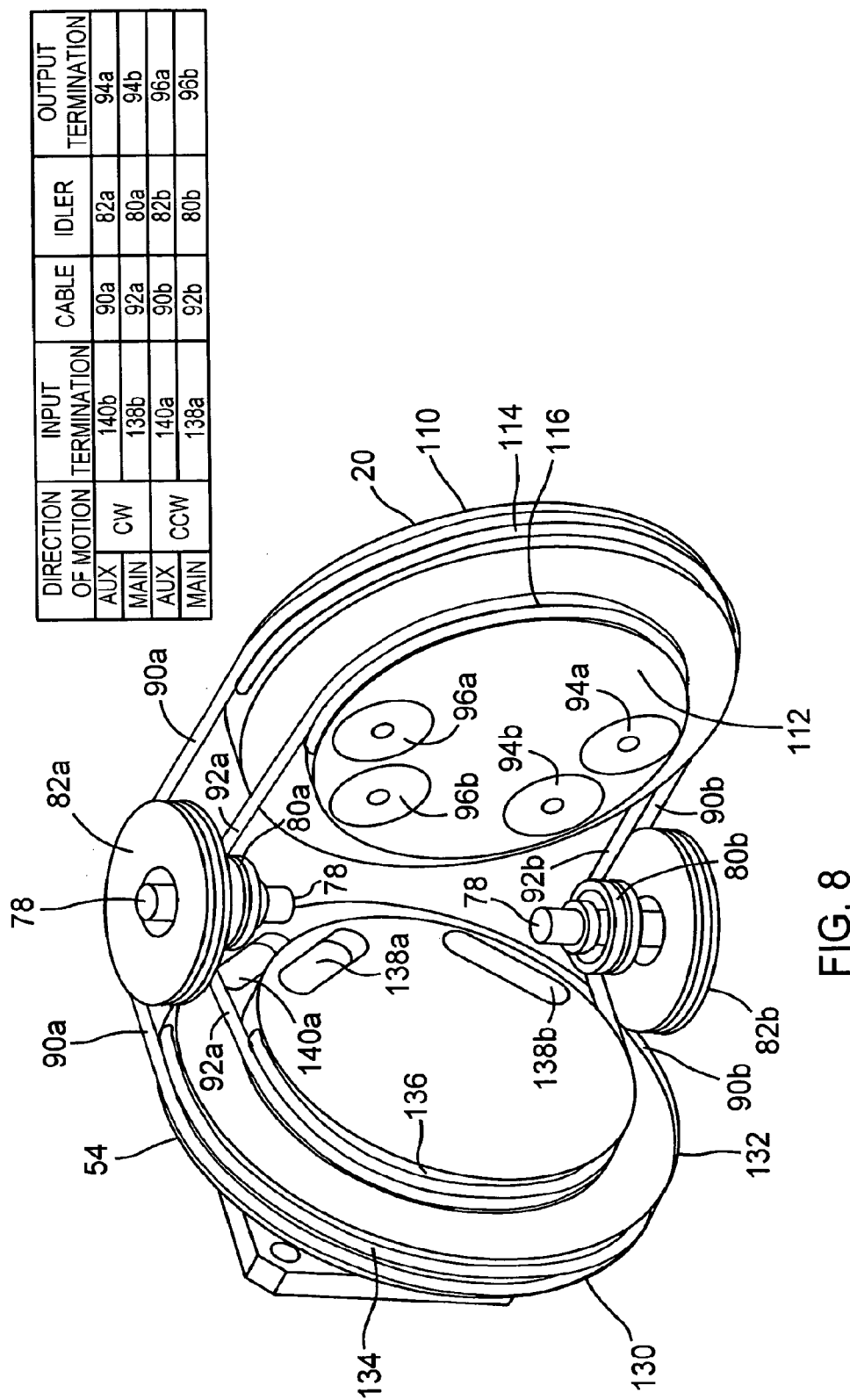

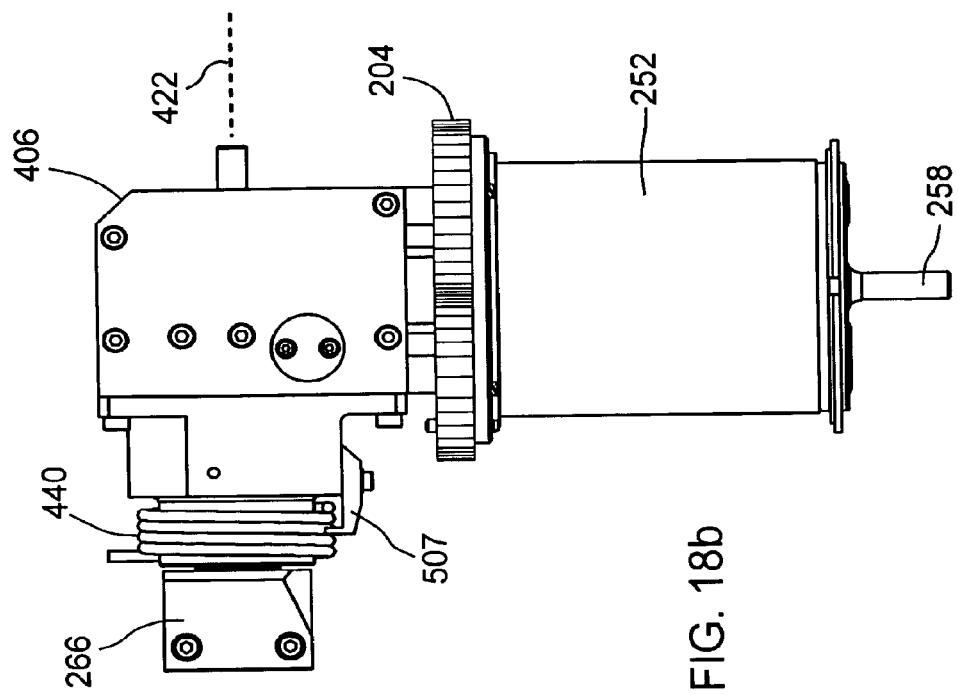
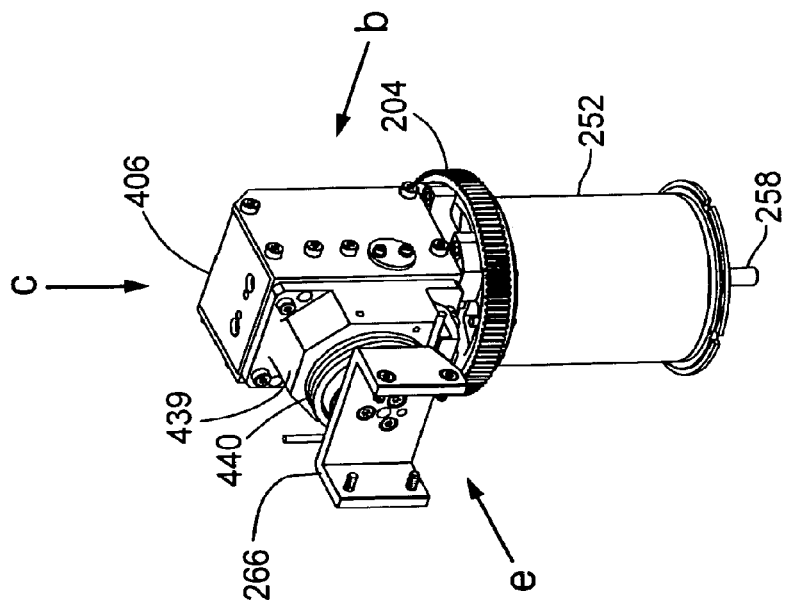
FIG. 18b
FIG. 18a

FIG. 21gb

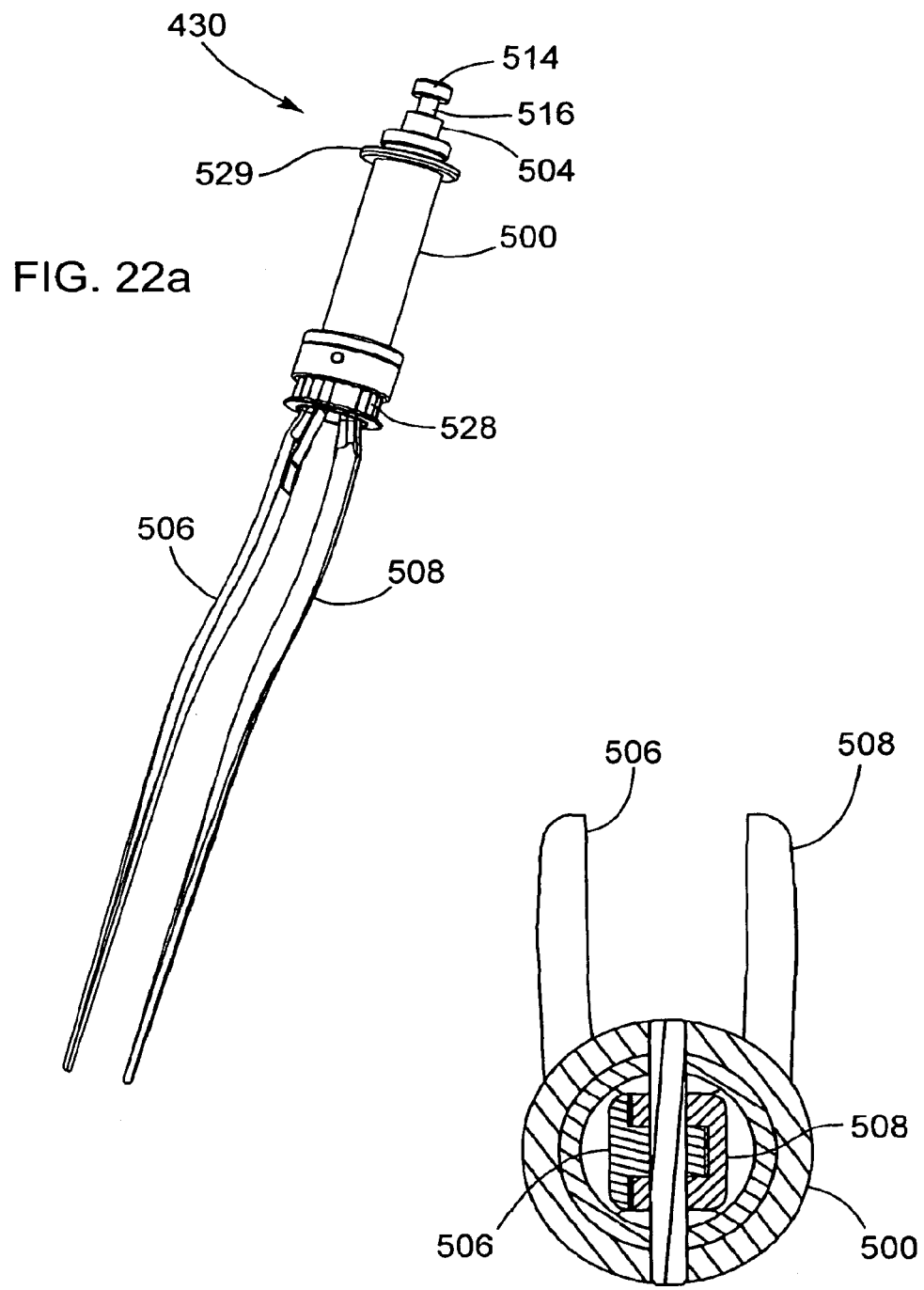

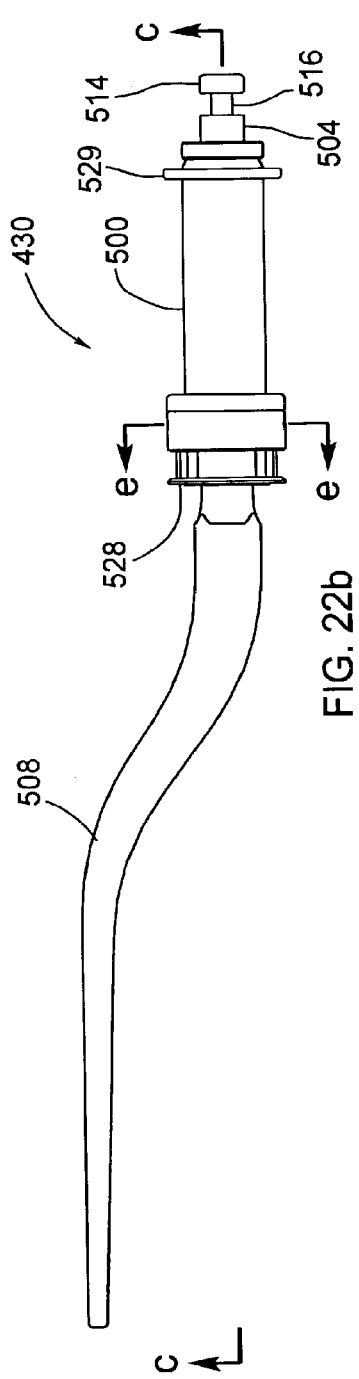
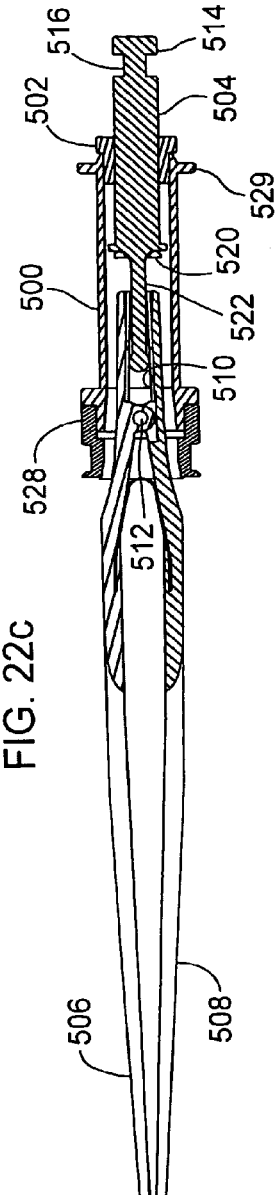
FIG. 22b
FIG. 22c
FIG. 22d

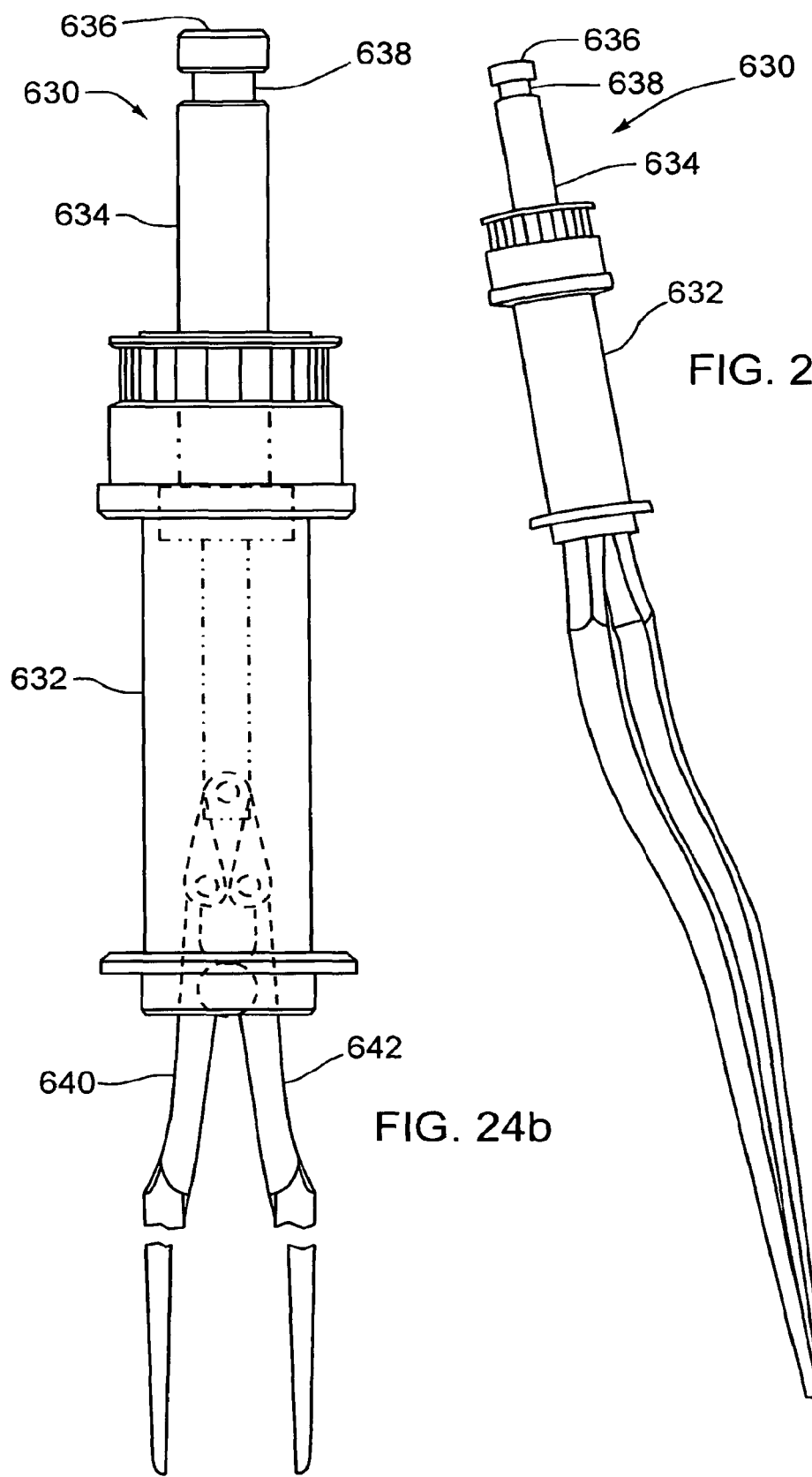

SURGICAL MANIPULATOR

CROSS REFERENCE TO RELATED U.S. PATENT APPLICATIONS

This patent application relates to, and claims the priority benefit of U.S. Provisional Application Ser. No. 61/008,574 filed Dec. 21, 2007, and this application is a continuation of U.S. utility patent application Ser. No. 12/318,151 filed on Dec. 22, 2008, which itself is a continuation-in-part (CIP) of U.S. utility patent application Ser. No. 11/812,094 filed on Jun. 14, 2007 entitled SURGICAL MANIPULATOR, filed in English, which are each incorporated herein in their entirety by reference.

FIELD OF THE INVENTION

The present invention relates to a surgical manipulator including a manipulator arm, an end-effector held by the manipulator arm, surgical tools held by the end-effector and manipulator joints, particularly right-angle drive devices for transmitting rotational motion in one axis to a perpendicular axis.

BACKGROUND OF THE INVENTION

The goal of surgical manipulator systems is to apply robotic and sensor technologies to improve the quality of patient surgical outcomes in a cost-effective manner. Surgical robotics can attain this goal through repeatable increased spatial resolution and better geometric accuracy of surgical tools positioning by the surgeon, faster operating speed, good ergonomics that can reduce the surgeon's fatigue, and the ability to provide a platform for surgeon training and education.

A number of commercial surgical robotic systems are currently in use including the NeuroArm Magnetic Resonance Imager (MRI) compatible neurosurgical robot by the University of Calgary, the da Vinci and Zeus surgical robots by Intuitive Surgical, the RAMS system by Microdexterity and the Jet Propulsion Laboratory, the Haptic Guidance System by MAKO, the SpineAssist by Mazor Surgical Technologies, as well as ROBODOC of Integrated Surgical Systems. For a list of reference to the existing patents of the above-mentioned systems, refer to the appendix.

The University of Calgary neuroArm system is designed to perform neurosurgery in an MRI environment. It has dual arms, each with 6 Degrees of Freedom in a master-slave configuration. The robot is MR compatible so no magnetic material is used for any part of the robot arm. It also has haptic feedback capability for sensing tool tip forces. Surgical tool changes are performed manually, see U.S. Pat. No. 7,155,316. The Intuitive Surgical da Vinci system is designed for laparoscopic surgery. It can have up to 5 arms controlled by the surgeon in a Master-slave control configuration. The system is large and heavy with a weight greater than 1000 lbs. There is no haptic feedback and tool changes are performed manually. The Zeus is a discontinued product that was also designed for laparoscopic surgery. Smaller and lighter than the da Vinci, the Zeus also had up to 5 arms in a Master-slave control architecture with no haptic capability and manual tool changes. (di Vinci: patents see attached list; Zeus: U.S. Pat. Nos. 5,515,478, 5,553,198, 5,645,520, 6,646,541, 6,714,841 etc)

Originally developed by JPL, the Robot-Assisted Micro-Surgery (RAMS) system is being commercialised by Micro-Dexterity. This telerobotic platform is designed for microsurgery on brain, eye, ear, nose, throat, face, and hand. Clinical tests had been performed on neurosurgery and hand surgery. The dual-arm system is very compact; the manipulator is approximately 25 mm in diameter and 250 mm long. The robot has a Master-slave architecture and exhibits high spatial resolution of 10 microns. The system has indirect pressure and texture sensing of the tool forces using joint encoder information. The surgical tools are changed manually, see U.S. Pat. No. 6,702,805.

The MAKO Haptic Guidance System targets knee replacement surgeries by means of a robotic system that assists the surgeon in arthroplasty through keyhole incisions. The FDA-approved system allows surgeon to pre-operatively optimize the size and alignment of knee, and execute surgeon-guided knee sculpturing and implant placing with CT image-guidance, see US patent Publications 20060142657, 07206627, 07139418)

Mazor Surgical Technologies developed the SpineAssist as a minimally invasive guidance systems for pedicle screw insertion as well as other spine related procedures. In the size of a soda can, the SpineAssist is a parallel-platform robot mounted onto the patient's spine or spinous process. Pre-operative planning with CT images is followed by automatic fluoroscope or CT image registration to the robot, after which the positioning device automatically directs its arm in the trajectory planned by the surgeon, with accuracy less than 1.5 mm.

In 1992, Integrated Surgical Systems introduced the ROBODOC, a large orthopedic surgical system intended for use in patients requiring primary cementless total hip replacement surgery. It has a single 6DOF arm that operates automatically using a pre-operatively defined program. It has no haptic feedback capability and tool changes are performed manually, see US Patent Publications 20040142803, 05766126, 06239874, 06349245.

The Pathfinder developed by Prosurgics is a stereotaxy tool-locator with image-guidance capabilities for intracranial neurosurgeries. The arm has six degrees-of-freedom and is passively manipulated by the surgeon without haptic feedback. The single-arm system is mounted on a mobile base. Surgical tools are changed out manually.

Laprotek is a minimally-invasive surgical robotics system. Developed by endoVia, the system is similar to Zeus. It has two four degrees-of-freedom arm teleoperated by joysticks at a console, with visual feedback also available via laparoscopic camera. It has haptic feedback using force sensors at the motors.

There are a number of aspects of the existing state of surgical robotic technology that require major improvements. The development of robot arms that are dexterous, precise and have large workspaces both in how they attain the work site location and when they are inside body cavities and organs. The overall size, weight and volume of most current systems are a major issue in that they have a major detrimental impact on operating room facility space and the support staff who set-up the equipment. Smaller, lighter weight stowable systems are needed. For example, the da Vinci surgical manipulator weighs 1200 lbs (exclusive of the operator interface) and stands approximately 8 ft. The Zeus arms are approximately 2 ft long and weigh 40 lbs. Total weight of the robot is 120 lbs. (exclusive of the user interface).

The majority of current systems do not provide Haptic feedback. Haptic feedback restores the lost sense of touch for the surgeon and may improve the surgeon's performance in terms of speed and reducing risk of collateral tissue damage.

Manual surgical tool exchange increases the surgical operating time; increasing the time the patient is required to remain under anaesthesia and increasing facility costs. The ability to automatically exchange surgical tools would therefore reduce patient risks and lower operating costs.

The high mechanical power density and small diameter of conventional dc motor servomotors are desirable traits to reduce the physical dimensions of robotic manipulators. However, the drawback of conventional servomotors presently in use in many surgical robots is their long axial length, so a right-angle transmission means is needed if excessive lateral extension of the manipulator arm joints is to be avoided.

Of all the available right-angle transmission components at present, bevel gear pairs deliver high torque and backdrivability, but backlash is typically high and they seldom come in small packages. The traditional standard bevel gear box has large backlash in transmission which is highly undesirable in applications where high precision is required in both directions of motion.

There are several manufacturers offering worm gears in a small package, and integrating with spring-loaded features the gearbox can be backlash free and achieve precise motion, but the lowered efficiency and the odd standard gear ratio increment suggest that more powerful (thus larger in size) motors will be needed. Worm gear boxes can have low-backlash configurations but its indirect proportional relationship between the efficiency versus the gear ratio leads to a bulkier and heavier overall unit, while also the lack of back-drivability is also undesirable in the event of crash recovery or calibration common to robotics applications.

Cable-pulley system provides an alternative to traditional gear-type mechanism, but introduces transmission error if any of the cable segments in the transmission chain is not tensioned properly. Researchers from Massachusetts Institute of Technology and eventually Barrett Technology developed the WAM, or the "whole-arm-manipulation", in which part of the mechanism involves a differential cable-pulley subset that allows for a two degree-of-freedom motion at the same joint driven by two independent motors. Cable within the WAM design is pretensioned at a single-point by turning two coaxial pulleys independently with cable responsible for both directions forming a U-shape turnaround at termination for auto-adjustment of cable length and tensioning automatically. Another differential pulley application can be found at the hoist and drive concept by Power Kinetics, in which cable pretension is accomplished by increasing the physical separation between pulleys. Commissariat a l'Energie Atomique, meanwhile, created a two to three degrees-of-freedom mechanism, using idle pulleys for both redirecting the direction of cable and also tensioning the cable. On the other hand, Roto-Lok mechanism developed by Sagebrush Technology is a parallel drum-drive configuration using cable and pulleys. Springs are presented at each of the cable termination to eliminate transmission slack. For a list of patents on the above-mentioned mechanisms refer to the appendix section. None of the above mentioned inventions can be adapted to a single-actuator right-angle transmission application, and their means of cable tension adjustment all require extra room for additional elements which will lead to the increase in overall size of the transmission module.

Harmonic drives, on the other hand, features zero-backlash, highly repeatable precision, back-drivability, high efficiency, compact size and lightweight. Unfortunately, the mechanism does not allow for a right-angle drive version. No commercially available right-angle transmission in the market currently has both zero-backlash and high efficiency capabilities in a compact in-line package.

Therefore, it would be very advantageous to provide a surgical robotic system employing right angle drives which avoids the above mentioned drawbacks.

SUMMARY OF THE INVENTION

The present invention provides embodiments of a surgical manipulator including a manipulator arm, an end-effector held by the manipulator arm, surgical tools held by the end-effector and manipulator joints, particularly right-angle drive devices for transmitting rotational motion in one axis to a perpendicular axis.

In one aspect of the invention there is provided surgical manipulator, comprising:

a) a base and a first right angle drive mechanism mounted on said base, a shoulder-roll drive mechanism located in said base for rotating said first right-angle drive mechanism about a shoulder-roll axis, said first right-angle drive mechanism including a first input pulley and a first output pulley mounted substantially perpendicular to said first input pulley, said first right-angle drive mechanism including a first bi-directional coupling mechanism for coupling said first input pulley and said first output pulley, a first drive mechanism coupled to said first input pulley for rotating said first input pulley about a first input axis wherein rotation of said first input pulley is translated into rotation of said first output pulley by said first bi-directional coupling mechanism about a shoulder-yaw axis which is substantially perpendicular to said first input axis;

a second right-angle drive mechanism coupled to said first output pulley of said first right angle drive mechanism, said second right-angle drive mechanism including a second input pulley and a second output pulley mounted substantially perpendicular to said second input pulley, said second right-angle drive mechanism including a second bi-directional coupling mechanism for coupling said second input pulley and said second output pulley, a second drive mechanism coupled to said second input pulley for rotating said second input pulley about a second input axis wherein rotation of said second input pulley is translated into rotation of said second output pulley by said bi-directional coupling mechanism about a shoulder-pitch axis which is substantially perpendicular to said first input axis;

b) a robotic upper arm being mounted at one end thereof to said second output pulley so that when said second output pulley is rotated, said robotic upper arm rotates about said shoulder-pitch axis, a third right-angle drive mechanism mounted in said robotic upper arm, said third right-angle drive mechanism including a third input pulley and a third output pulley mounted substantially perpendicular to said third input pulley, said third right-angle drive mechanism including a third bi-directional coupling mechanism for coupling said third input pulley and said third output pulley said third right-angle drive mechanism including a third drive mechanism coupled to said third input pulley for rotating said third input pulley about a third input axis, wherein rotation of said third input pulley about said third input axis is translated into rotation of said third output pulley by said bi-directional coupling mechanism about an elbow-pitch axis substantially perpendicular to said third input axis;

c) a robotic fore arm mounted on said third output pulley of said third right-angle drive mechanism so that when said third output pulley is rotated, said robotic fore arm rotates about said elbow-pitch axis, a fourth right-angle drive mechanism mounted in said robotic fore arm, said fourth right-angle drive mechanism including a fourth input pulley and a fourth output pulley mounted substantially perpendicular to said fourth input pulley, a fourth bi-directional coupling mechanism for coupling said fourth input pulley and said fourth output pulley, said fourth right-angle drive mechanism including a fourth drive mechanism coupled to said fourth input pulley for rotating the fourth input pulley about a fourth input axis, wherein rotation of said fourth input pulley about said fourth input axis is translated into rotation of said fourth output pulley by said bi-directional coupling mechanism about a wrist-pitch axis substantially perpendicular to said fourth input axis;

d) a robotic wrist mounted on said fourth output pulley of said fourth right-angle drive mechanism so that when said fourth output pulley is rotated, said robotic wrist rotates about said wrist-pitch axis, said robotic wrist including an actuation mechanism coupled to a wrist output shaft for rotating said robotic wrist output shaft about a wrist-roll axis; and e) an end-effector mounted to said wrist output shaft, said end-effector including gripping means for releasibly gripping a surgical tool wherein when said actuation mechanism is engaged said end-effector is rotated about said wrist-roll axis.

The present invention also provides a surgical manipulator system, comprising:

a) a base and a first right-angle drive mechanism mounted on said base, a shoulder-roll drive mechanism located in said base for rotating said first right-angle drive mechanism about a shoulder-roll axis, said first right-angle drive mechanism including a first input pulley and a first output pulley mounted substantially perpendicular to said first input pulley, said first right-angle drive mechanism including a first bi-directional coupling mechanism for coupling said first input pulley and said first output pulley, a first drive mechanism coupled to said first input pulley for rotating said first input pulley about a first input axis wherein rotation of said first input pulley is translated into rotation of said first output pulley by said first bi-directional coupling mechanism about a shoulder-pitch axis which is substantially perpendicular to said first input axis;

b) a robotic upper arm being mounted at one end thereof to said first output pulley so that when said first output pulley is rotated, said robotic upper arm rotates about said shoulder-pitch axis, a second right-angle drive mechanism mounted in said robotic upper arm, said second right-angle drive mechanism including a second input pulley and a second output pulley mounted substantially perpendicular to said second input pulley, said second right-angle drive mechanism including a second bi-directional coupling mechanism for coupling said second input pulley and said second output pulley, a second drive mechanism coupled to said second input pulley for rotating said second input pulley about a second input axis wherein rotation of said second input pulley is translated into rotation of said second output pulley by said second bi-directional coupling mechanism about a elbow-pitch axis which is substantially perpendicular to said second input axis;

c) a robotic fore arm mounted on said second output pulley of said second right-angle drive mechanism so that when said second output pulley is rotated, said robotic fore arm rotates about said elbow-pitch axis, a third right-angle drive mechanism mounted in said robotic fore arm, said third right-angle drive mechanism including a third input pulley and a third output pulley mounted substantially perpendicular to said third input pulley, said third right-angle drive mechanism including a third bi-directional coupling mechanism for coupling said third input pulley and said third output pulley, a third drive mechanism coupled to said third input pulley for rotating said third input pulley about a third input axis wherein rotation of said third input pulley is translated into rotation of said third output pulley by said third bi-directional coupling mechanism about an wrist-pitch axis substantially perpendicular to said third input axis;

d) a fourth right-angle drive mechanism mounted on said third output pulley of said third right-angle drive mechanism, said fourth right-angle drive mechanism including a fourth input pulley and a fourth output pulley mounted substantially perpendicular to said fourth input pulley, said fourth right-angle drive mechanism including a fourth bi-directional coupling mechanism for coupling said fourth input pulley and said fourth output pulley, a fourth drive mechanism coupled to said fourth input pulley for rotating said fourth input pulley about a fourth input axis and wherein rotation of said fourth input pulley is translated into rotation of said fourth output pulley by said fourth bi-directional coupling mechanism about a wrist-yaw axis substantially perpendicular to said fourth input axis;

e) a robotic wrist mounted on said fourth output pulley of said fourth right-angle drive mechanism so that when said fourth output pulley is rotated, said robotic wrist rotates about said wrist-yaw axis, said robotic wrist including an actuation mechanism coupled to a wrist output shaft for rotating said robotic wrist output shaft about a wrist-roll axis; and f) an end-effector mounted to said wrist output shaft, said end-effector including gripping means for releasibly gripping a surgical tool wherein when said actuation mechanism is engaged said end-effector is rotated about said wrist-roll axis.

The present invention also provides a surgical manipulator system, comprising:

a) at least first and second surgical manipulators as disclosed above;

b) left and right hand controllers with the right hand controller being associated with the first surgical manipulator and the left hand controller being associated with the second surgical manipulator, said at least first and second hand controllers being configured to be operated by a surgeon;

c) communication system coupling said left and right hand controllers to said at least first and second surgical manipulators for translating movement of said left and right hand controllers to scaled movement of said at least first and second surgical manipulators; and d) a vision system focused on a work area including an area of a patient to be operated on and focused on the end-effectors and associated surgical tools attached to said at least two surgical manipulators, said vision system including display means for displaying images of said work area to a surgeon.

A further understanding of the functional and advantageous aspects of the invention can be realized by reference to the following detailed description and drawings.

BRIEF DESCRIPTION OF THE DRAWINGS

Embodiments of the invention will be more fully understood from the following detailed description thereof taken in connection with the accompanying drawings, which form a part of this application, and in which:

FIG. 1 is an isometric view of an assembled right-angle drive system constructed in accordance with the present invention;

FIG. 2 is an exploded, disassembled view of the right-angle drive system of FIG. 1;

FIG. 3b is a side view of the output shaft of FIG. 3a;

FIG. 4b is a front view of the mid housing of FIG. 4a;

FIG. 4f shows a bearing mounting on the output shaft of FIG. 3a mounted in the mid-housing of FIG. 4a;

FIG. 5a is an isometric view of an output pulley forming part of the right angle drive;

FIG. 5b is a front view of the output pulley of FIG. 5a;

FIG. 5c is a bottom view of FIG. 5b;

FIG. 5d is a cross sectional view along the line A-A of FIG. 5b;

FIG. 6a is an isometric view of an input pulley forming part of the right angle drive;

FIG. 6b is a front view of the input pulley of FIG. 6a;

FIG. 6c is a top of FIG. 6a;

FIG. 6d is a cross sectional view along the line C-C of FIG. 6b;

FIG. 7a shows an isometric view of an idler shaft forming part of the right angle drive;

FIG. 7b shows a front view of the idler shaft of FIG. 7a;

FIG. 8 shows the relative positions of the input and output pulleys perpendicular to each other and the driving cables and idlers for converting rotational motion of the input pulley into rotational motion of the output shaft oriented perpendicular to the input axis;

FIG. 9c shows the side view of the tensioning screw of FIG. 9a;

FIG. 9d shows the front view of the tensioning screw of FIG. 9a;

FIG. 10b shows the cross-sectional view of FIG. 10a along the line A-A of FIG. 10a;

FIG. 13 shows the opposite assembled side view to FIG. 11a;

FIG. 16a is an isometric view of a surgical robot forming part of the present invention;

FIG. 16b is a side view looking along arrow b of FIG. 16a;

FIG. 16c is a front view looking along arrow c of FIG. 16a;

FIG. 16d is a top view looking along arrow d of FIG. 16a;

FIG. 17a is an isometric view of the manipulator base without the cover;

FIG. 17b is a top view of FIG. 17a along the arrow b;

FIG. 17c is a front cross-section view of FIG. 17b along the line c-c showing the actuation components of the shoulder-roll joint;

FIG. 17d is a side cross-section view of FIG. 17b along d-d showing the actuation components of the shoulder-roll joint;

FIG. 17e is a front cross-section view of FIG. 17b along e-e showing the actuation components of the shoulder-roll joint and showing the cover 402;

FIGS. 18a to 18e show details of the manipulator shoulder with the right angle drive mounted on top of the shoulder-roll driven shaft forming a shoulder-pitch joint assembly;

FIG. 18a is an isometric view of the manipulator shoulder;

FIG. 18b is a front view of FIG. 18a along the arrow b;

FIG. 18c is a top view of FIG. 18a along the arrow c;

FIG. 18d is a cross-section view of FIG. 18c along the line d-d;

FIG. 18e is a side view of FIG. 18a along the arrow e

FIG. 19a is an isometric view of the lower manipulator arm;

FIG. 19b is a front view of FIG. 19a along the arrow b;

FIG. 19c is a side view of FIG. 19a along the arrow c;

FIG. 19d is a top view of FIG. 19a along the arrow d;

FIG. 19e is a cross-section view of FIG. 19c along the line e-e;

FIGS. 20a to 20f show details of the manipulator upper arm and the right angle drive mounted at the front of the manipulator upper arm forming a wrist-pitch joint assembly;

FIG. 20a is an isometric view the manipulator fore arm;

FIG. 20b is a side view of FIG. 20a along the arrow b;

FIG. 20c is a bottom cross-section view of FIG. 20b along line c-c;

FIG. 20d is a top view of FIG. 20a along the arrow d;

FIG. 20e is a back cross-section view of FIG. 20b along e-e;

FIG. 21a is an isometric view of the wrist;

FIG. 21b is a top view of FIG. 21a along the arrow b;

FIG. 21c is a front cross-section view of FIG. 21b along line c-c;

FIG. 21d is a front view of FIG. 21a along the arrow d;

FIG. 21e is a side cross-section view of FIG. 21b along line e-e;

FIGS. 21fa and 21fb show two isometric views of the original six degrees-of-freedom manipulator configuration shown in FIGS. 16a to 16e;

FIGS. 21ga and 21gb show two isometric views of the one seven degrees-of-freedom manipulator configuration with a shoulder-yaw joint introduced to that of the configuration shown in FIG. 21f;

FIGS. 21ha and 21hb show two isometric views of the one seven degrees-of-freedom manipulator configuration with a wrist-yaw joint introduced to that of the configuration shown in FIG. 21f;

FIG. 21i shows an isometric view of the exploded joint units of the original six degrees-of-freedom manipulator configuration shown in FIG. 21f in which the modular components include quick connectors/disconnectors for rapid assembling and disassembling;

FIGS. 22a to 25b show details of the surgical forcep tools;

FIG. 22a is an isometric view of a first embodiment of a surgical tool;

FIG. 22b is a side view of the surgical tool of FIG. 22a;

FIG. 22c is a bottom cross-sectional view along the line c-c of FIG. 22b with the surgical tool in the open position;

FIG. 22d is a bottom cross-sectional view along the line c-c of FIG. 22b with the surgical tool in the closed position;

FIG. 22e is a back cross-sectional view along the line e-e of FIG. 22a;

FIG. 23a is an isometric view of an alternative embodiment of a surgical tool in the opened position;

FIG. 23b is an elevational view of the surgical tool of FIG. 23a;

FIG. 24a is an isometric view of an alternative embodiment of a surgical tool in the closed position;

FIG. 24b is an elevational view of the surgical tool of FIG. 24a;

FIG. 25a is an isometric view of another alternative embodiment of a surgical tool; and FIG. 25b is an elevational view of the surgical tool of FIG. 25a.

FIG. 26c is a front view of FIG. 26a;

FIG. 28b is a cross-sectional view of the tool actuator along the line b-b of FIG. 28a;

FIG. 29b is a cross-sectional view of the tool holder along line b-b in FIG. 29a;

DETAILED DESCRIPTION OF THE INVENTION

Figure 3A:
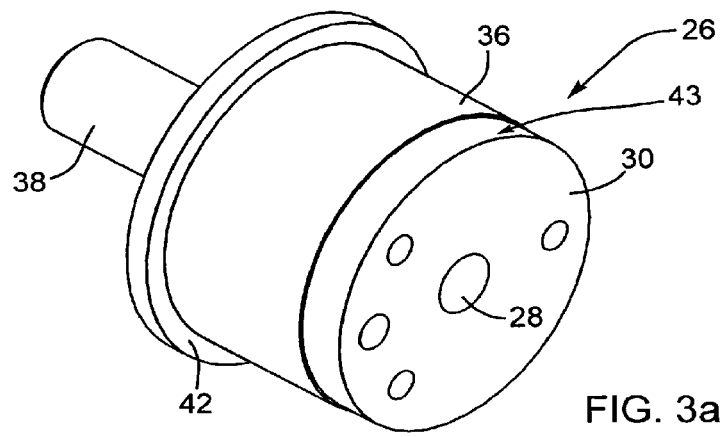
FIG. 3a is an isometric view of the output shaft forming part of the right angle drive.

Generally speaking, the systems described herein are directed to a surgical manipulator apparatus. As required, embodiments of the present invention are disclosed herein. However, the disclosed embodiments are merely exemplary, and it should be understood that the invention may be embodied in many various and alternative forms. The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to a surgical manipulator apparatus.

The surgical manipulator apparatus comprises a multi-jointed robotic arm, with the different booms connected to right angle drive units, and surgical end-effectors connected to a robotic wrist unit. Each of these components will now be described in detail.

1) Right Angle Drive Unit

Referring first to FIG. 1, an isometric view of an assembled right-angle drive system is shown generally at 10 which includes a housing comprised of a chassis 14 and a cover 16. Referring particularly to FIG. 2, the right angle drive system 10 includes an output pulley 20, an output shaft 26 on top of which the output pulley 20 is mounted to, a mid housing 22, a pair of idler units 78, 86, 84, 80a/b, 82a/b, an optical encoder 46, and an input pulley 54 mounted on a drive mechanism which preferably comprises a harmonic-drive 56.

Figure 3B:
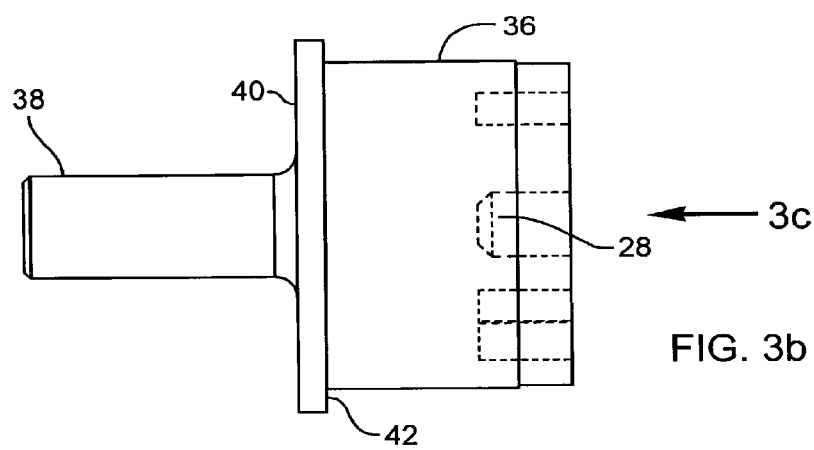

Referring to FIG. 2 and FIGS. 3a and 3b, the optical encoder 46 is mounted on shaft section 38 of output shaft 26 for measuring rotational displacement of the output shaft 26. The typical optical encoder 46 measuring system includes a light source, a code disk rotating about an internal or external precision ball bearing and an optical light sensor. The code disk has a series of opaque and transparent markings which spatially encode the angular position of the shaft section 38 that may be configured to provide the absolute or relative angular position of the shaft. A light source shines through the code disk and onto the optical light sensor. Every angular position has coded dark spots and light spots on the code disk which interrupt the light beam on the optical light sensor, from which electronic signals are generated. The electronic signals are amplified and converted into angular position/speed data which can be used by a control system.

For an incremental encoder embodiment, all the markings on the code disc are identical, and electronic signals are generated in the form of pulses which are counted by the controller to determine the relative positioning or differentiated against time to obtain speed. For an embodiment which uses an absolute encoder, each marking on the code disc is distinctively formed by a series of lines, and the resulting electronic signal from the light detection of the optical sensor will be a unique binary code which makes absolute position sensing possible.

The harmonic-drive 56 is mounted to the chassis 14, and on the output flange 98 of the harmonic-drive 56 an input pulley 54 is mounted and has an axis of rotation perpendicular to that of the output pulley 20. The harmonic-drive 56 is used to introduce high reduction ratio to the overall right-angle drive 10. The cable-pulley system thus is only responsible for the angled transmission of motion from the input to the output side and thus forms a bi-directional coupling mechanism since rotation of the input shaft about its axis in one direction causes rotation of the output shaft about its axis in one direction, and rotation of the input shaft by the drive mechanism in the other direction causes rotation of the output shaft about its axis in the other direction.

FIGS. 6*a* to 6*e*, and FIG. 12 show details of the input pulley 54. Input pulley 54 includes two sections, an auxiliary section 130 and a main section 132 with the auxiliary section 130 having a larger diameter than the main section 132 to accommodate for the vertical locations of the main idlers 80*a*, 80*b* and auxiliary idlers 82*a*, 82*b* (FIG. 1). Sections 130 and 132 have circular grooved circumferences 134 and 136 with spiral continuous grooves 160 (FIG. 6*g*) on the surfaces to provide friction between the cable and the input pulley 54 such that the driving torque for the pulley by the cable is distributed evenly about the pulley and not completely relying on the termination at the looped crimped fittings 101 (FIG. 6*f*) located inside the pockets 138 and 140. The cables are terminated at the input pulley 54 by threading into the corresponding lateral access holes 141*a*, 141*b*, 141*c*, 141*d* and through the pockets 140*a*, 138*a*, 140*b*, 138*b* respectively.

Figure 6E:
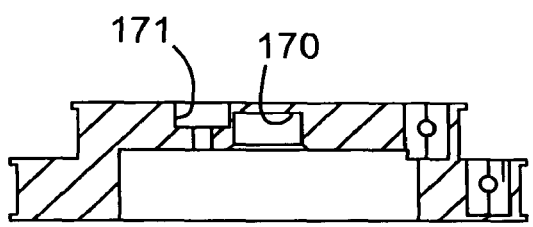
FIG. 6e is a cross sectional view along the line B-B of FIG. 6b.
Figure 6F:
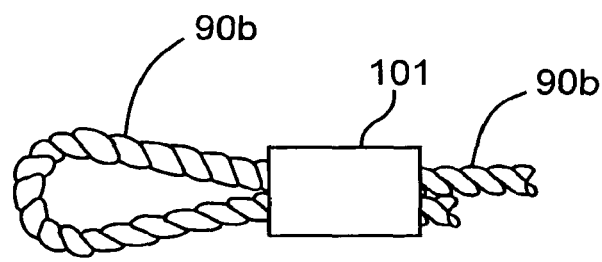
FIG. 6f is a view of the cable termination subassembly with a loop sleeve crimped fitting.

The loop crimp fittings 101 provided by the cable manufacturer are crimped onto the tip of the cables with each forming a loop at the other end of the fitting as shown in FIG. 6*f*. Each fitting together with the loop hides inside the pockets 138*a*, 138*b*, 140*a*, 140*b*, in which when each cable is under tension its fitting will ride up against the internal wall of the pocket and maintain the cable tension.

Referring to FIGS. 6*a*, 6*g*, 8 and 11*c*, cable 92*b* (FIG. 8) is wrapped around the main section 132 (FIG. 6*a*) of the input pulley 54 along the circular groove section 160 (FIG. 6*g*) which is machined on the circumferential surface 136 in a spiral helical path along the center of rotation of the pulley. The direction of which cable 92*b* winds around the surface 136 (FIG. 6*a*) is counter-clockwise starting from the lateral access hole above the loop sleeve termination pocket 138*a* and looking into the input pulley 54 in the view direction of FIG. 6*b*. When the cable 92*b* is inside the groove 160, the surface friction in between the two assists in the input pulley 54 driving the cable 92*b* with tension which in turn drives the output pulley 20, thus relieving some of the stress concentrated at the loop sleeve fitting 101 (FIG. 11*c*) where the cable is terminated. The adjacent groove section 161 (FIG. 6*g*), which is wound around by cable 92*a* (FIG. 8) clockwise, may or may not be continuous with section 160 depends on the axial length of the main cable section 132. The identical relationship applies to the auxiliary cable section 130 as groove section 162 (FIG. 6*g*) is for cable 90*b* (FIG. 8) winding counter-clockwise and groove section 163 (FIG. 6*g*) is for cable 90*a* (FIG. 8) winding clockwise.

Figure 3C:
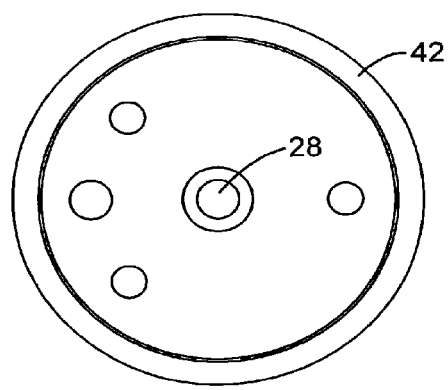
FIG. 3c is a view of the output shaft along the arrow 3c in FIG. 3b.
Figure 4A:
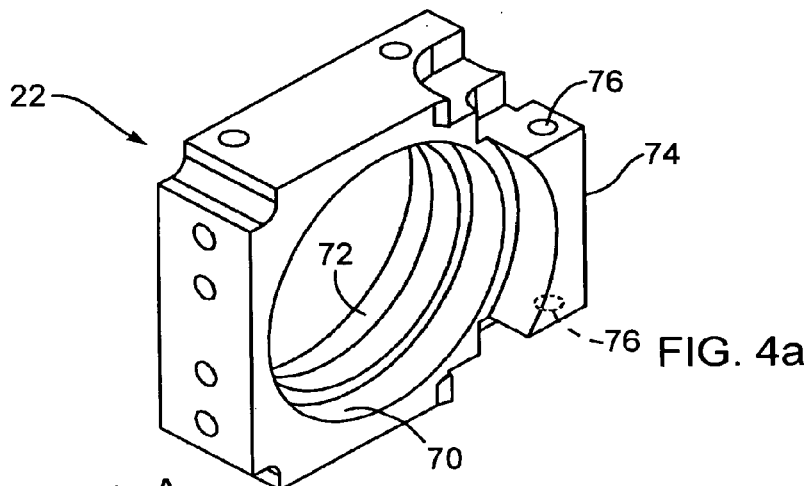
FIG. 4a is an isometric view of a mid-housing forming part of the right angle drive.
Figure 4B:
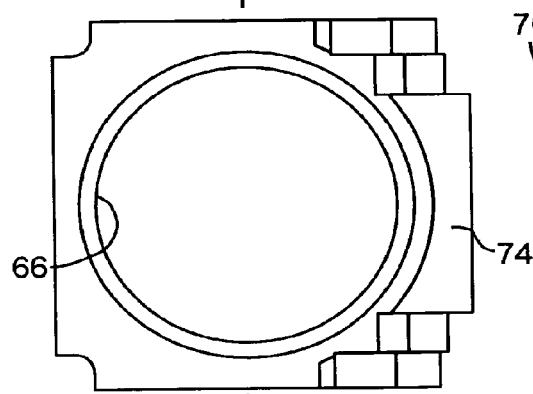
Figure 4C:
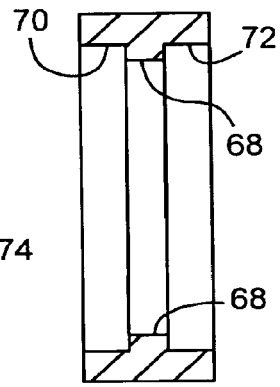
FIG. 4c is a cross sectional view along the line A-A of FIG. 4b.
Figure 4D:
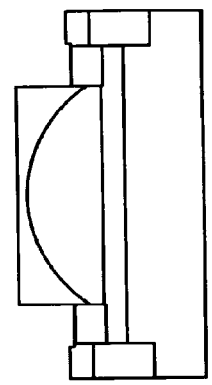
FIG. 4d is equivalent to the view direction of FIG. 4c but showing all surface features of the mid housing.
Figure 4E:
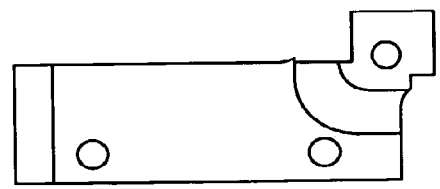
FIG. 4e is a bottom view of FIG. 4b along the arrow 4e.
Figure 4F:
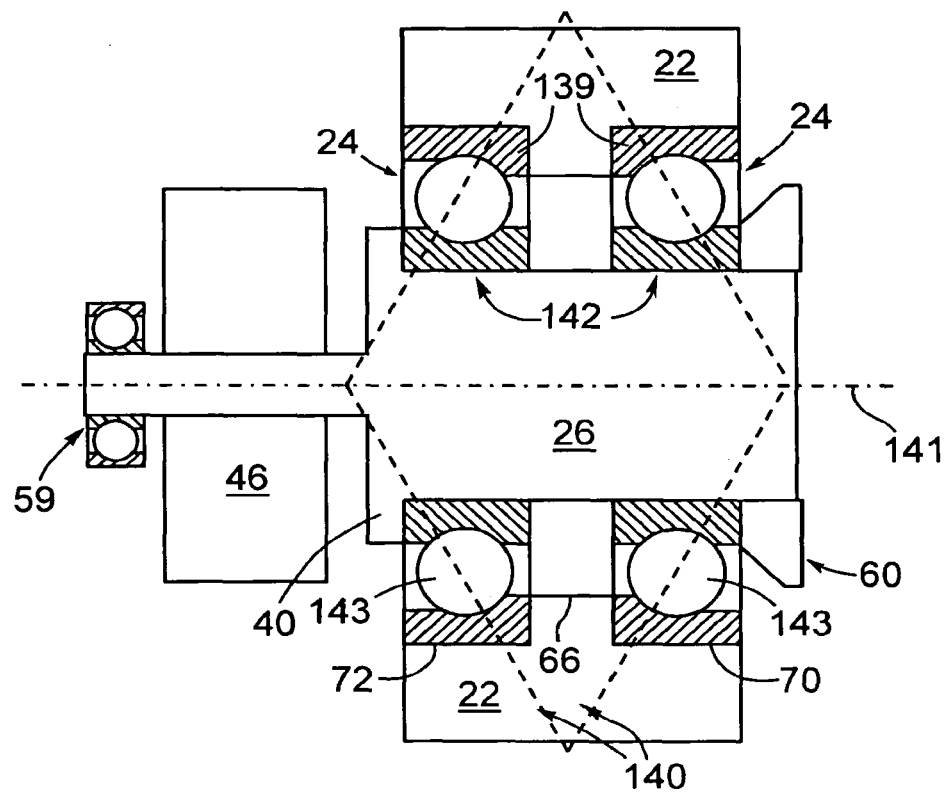

Referring to FIGS. 3*a*, 3*b* and 3*c*, the output shaft 26 includes a cylindrical housing 36 and a shaft 38 extending from the rear face 40 of output shaft 26 and the rear face 40 includes a circumferential shoulder 42 of a larger diameter than the diameter of cylindrical housing 36. There is a centered hole 28 located on a front face 30 to receive therein a centering dowel 32 which forms the rotating output seen in FIG. 1 protruding from the center of output pulley 20. Referring to FIG. 4*f*, a radial ball-bearing 59 is mounted on shaft 38 between which the shoulder 42 of the output shaft 40 the encoder 46 is sandwiched.

Referring to FIGS. 4*a* to 4*f*, the mid-housing 22 includes a pair of circular bores 70 and 72 which are match-machined to be perfectly concentric to each other for the angular-contact ball-bearings 24 shown in FIG. 1. The diameter 68 which is smaller than that of 70 and 72 is sized according to the recommended outer ring shoulder landing diameter specified by the bearing manufacturer. Details of the mounting and preloading of the angular-contact ball-bearing pair 24 inside mid-housing 22 will be described later. Mid-housing 22 includes an idler support section 74 (FIG. 4*a*) having two holes 76, one on the top surface and the other on the bottom surface for receiving idler shafts 78 which are part of the main idler mechanisms, shown in FIG. 2.

Figure 11A:
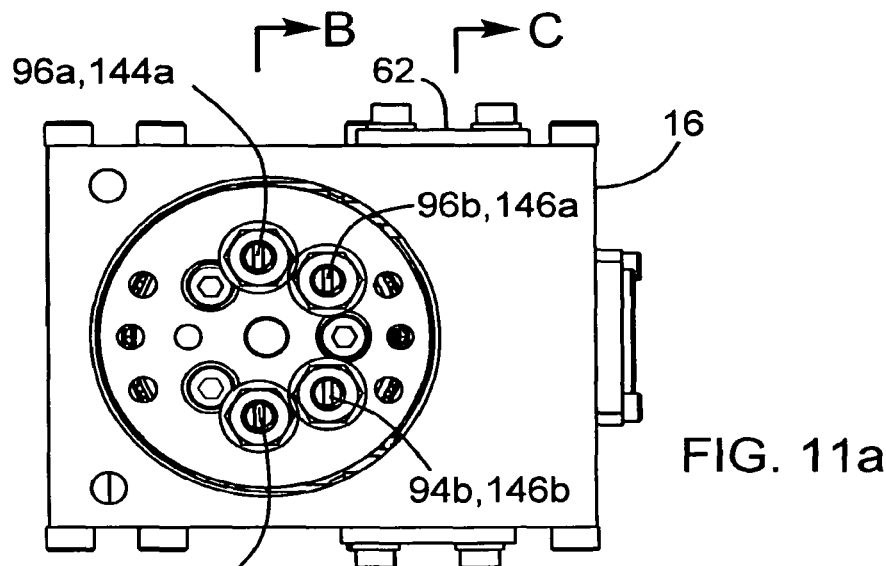
FIG. 11a shows the assembled side view of the right-angle drive with the output pulley front face.
Figure 11B:
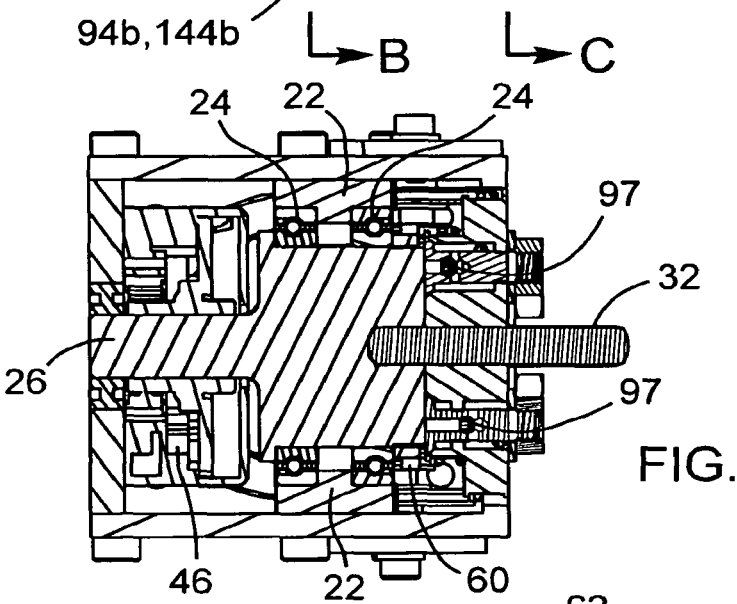
FIG. 11b shows a cross-sectional view of FIG. 11a along line B-B of FIG. 11a for the output elements.
Figure 11C:
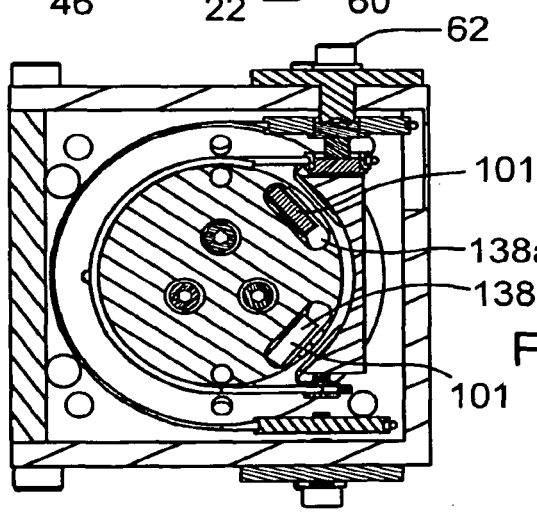
FIG. 11c shows a cross-sectional view of FIG. 11a along line C-C of FIG. 11a for the input elements and the top idler subassembly.
Figure 12:
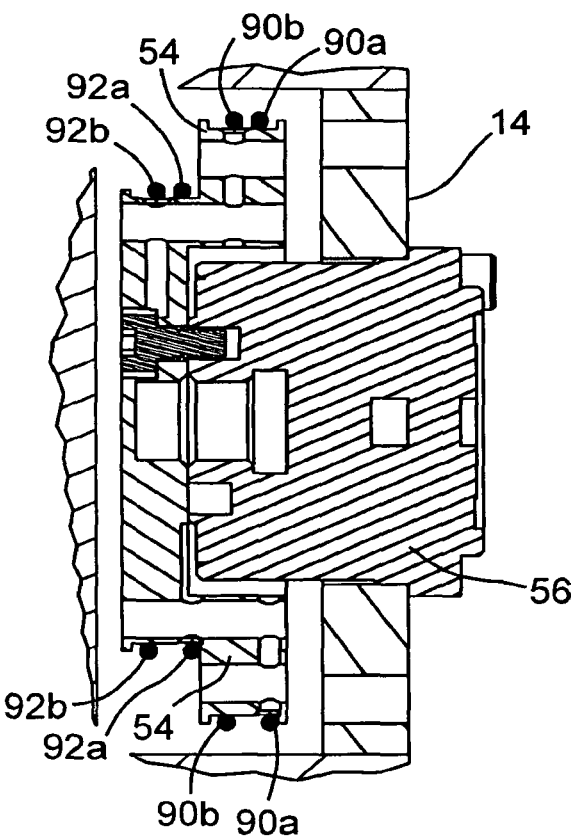
FIG. 12 shows a side cross-sectional view of the input elements.

Referring to FIGS. 4*f* and 11*b*, the two angular-contact ball-bearings 24 are mounted inside the bearing seats 70, 72 in a back-to-back configuration (best seen in FIG. 4*f*). The bearings 24 are seated with their respective outer ring 139 inside the concentric bore 72 and 70. The locknut 60 is turned on the output shaft 26 via a threaded section 43 (FIG. 3*a*), which provides loading from the locknut 60 via the output shaft 26 to the inner ring 142 of the bearing adjacent to the locknut 60 (see FIG. 4*f*). The loading will be transmitted from the inner ring 142 through the balls 143 and to the outer ring 139 of that bearing, following the load path outlined along 140 shown in dotted lines, and end up back at the output shaft 26 again at the flange 40 (FIG. 3*b*). The preload is completed when the inner gap inside the raceway of the bearings 24 between the balls 143 and the inner ring 142 and outer ring 139 is eliminated by the motion of the locknut 60 towards the bearing pairs along the output shaft 26 as a result of the turning of the locknut 60. This procedure is carried out by means of the use of a torque wrench to tighten the locknut 60 on output shaft 26, using a torque level recommended by the bearing manufacturer for installation.

FIGS. 5*a* to 5*f* inclusive show details of the output pulley 20. Output pulley 20 includes two sections 110 and 112 with the auxiliary section 110 having a larger diameter than the main section 112 to accommodate for the vertical locations of the main 80*a*, 80*b* and auxiliary idlers 82*a*, 82*b*. Sections 110 and 112 have circumferences 114 and 116 respectively with continuous spiral grooves 160 (of FIG. 6*g*) on the surfaces to provide friction between the cable and the output pulley 20 in order to distribute the driving torque evenly about the pulley 20 and relieve stress on the termination at the tensioning screws 94*a*, 94*b* and 96*a*, 96*b* thereby reducing the possibility of detachment. FIG. 11*a* shows the front view of the drive unit showing the positioning of the tensioning screws in the holes 144*a*, 144*b*, 146*a* and 146*b*.

Figure 5E:
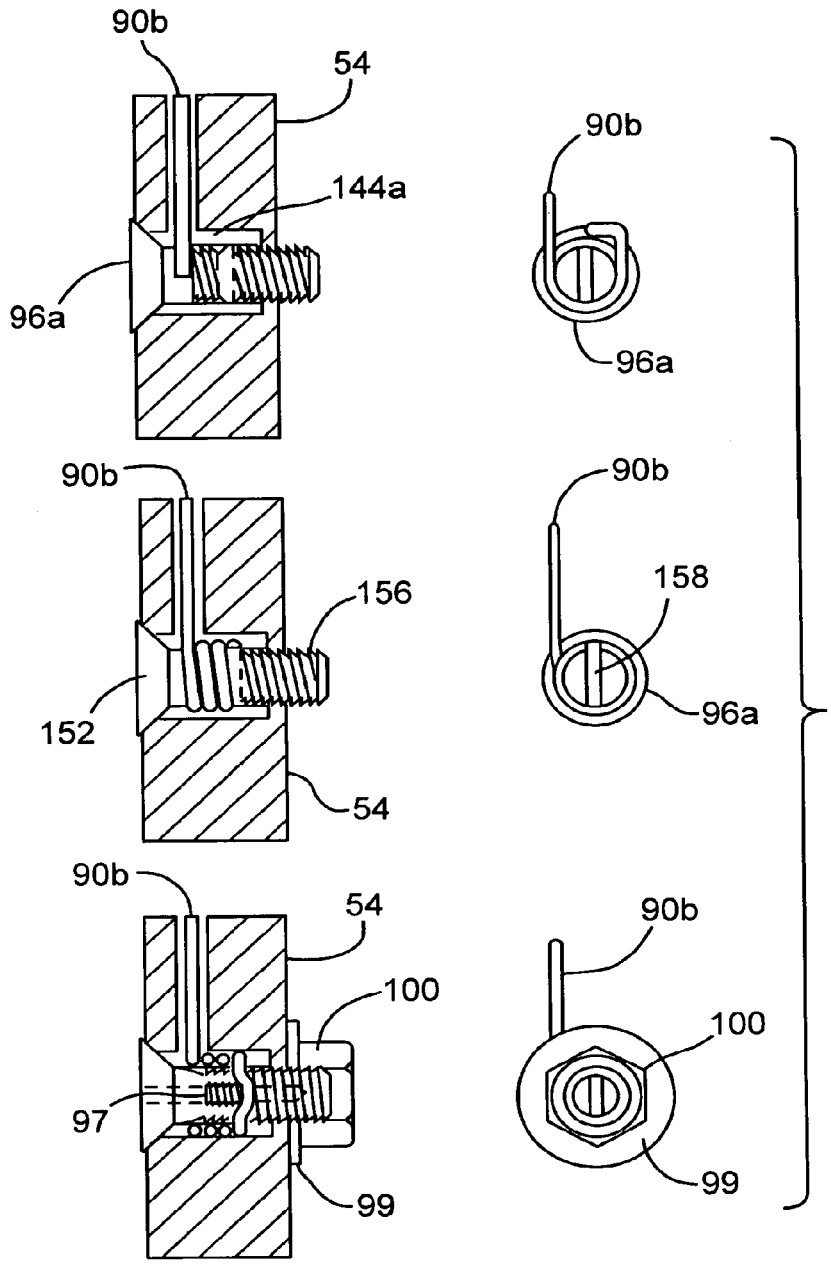
FIG. 5e is a detail view of FIG. 5d showing the details of the tensioning mechanism.
Figure 5F:
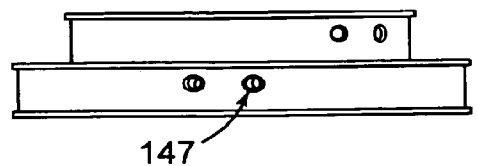
FIG. 5f is a top view of FIG. 5b.
Figure 6G:
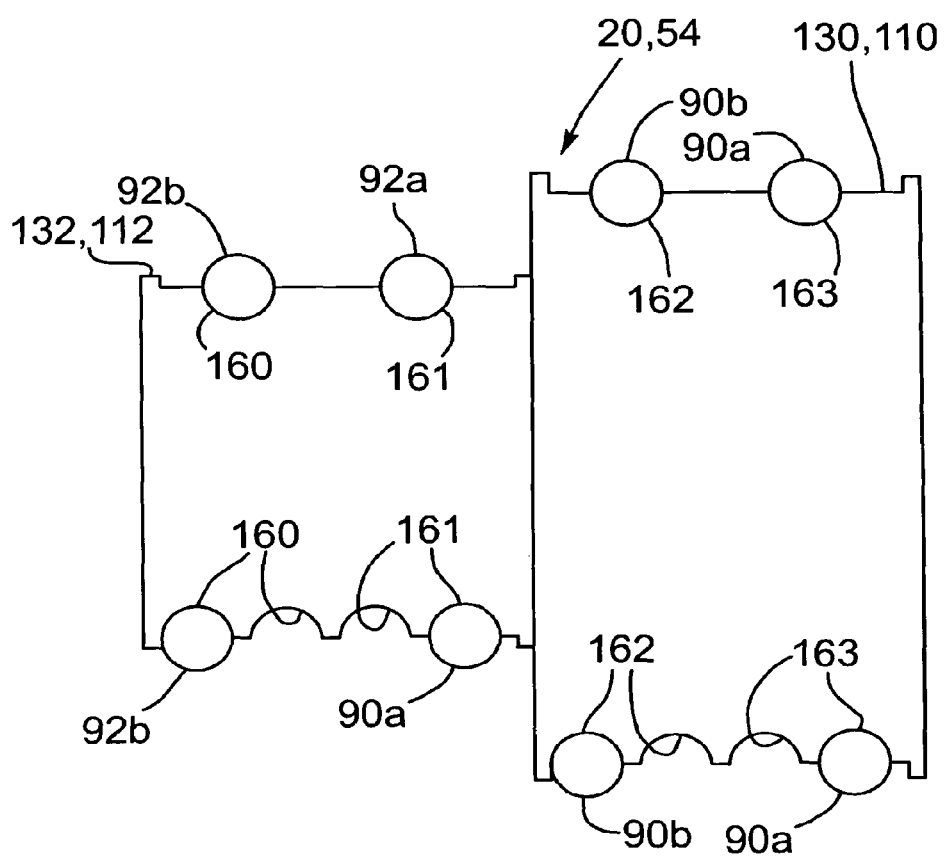
FIG. 6g is a cross-section view of the input and output pulleys of FIGS. 5a and 6a illustrating the grooved circumference on both the input and output pulley for the cable wrapping.

Referring to FIGS. 5*a*, 6*g* and 8, cable 92*b* (FIG. 8) is wrapped around the main section 112 (FIGS. 5*a* and 8) of the output pulley 20 along the circular groove 160 (FIG. 6*g*) which is machined on the circumferential surface 116 (FIG. 5*a*) in a spiral helical path along the center of rotation of the pulley 20. The direction of which cable 92*b* winds around the surface 116 is counter-clockwise starting from the lateral access hole above the tensioning screw hole 146*a* and looking into the output pulley 20 at the output load interface surface. When the cable 92*b* is inside the groove 160, the surface friction in between the two assists in driving the output pulley 20 to rotate counter-clockwise when the cable 92*b* is under tension, thus relieving some of the stress concentrated at the tensioning screw 96b inside the tensioning screw hole 146a where the cable is terminated. The adjacent groove section 161 (FIG. 6g), which is wound around by cable 92a (FIG. 8) clockwise, may or may not be continuous with groove 160 depending on the axial length of the main section 112. The identical relationship applies to the auxiliary section 110 as groove section 162 (FIG. 6g) is for cable 90b (FIG. 8) winding counter-clockwise and groove section 163 (FIG. 6g) is for cable 90a (FIG. 8) winding clockwise.

Figure 9A:
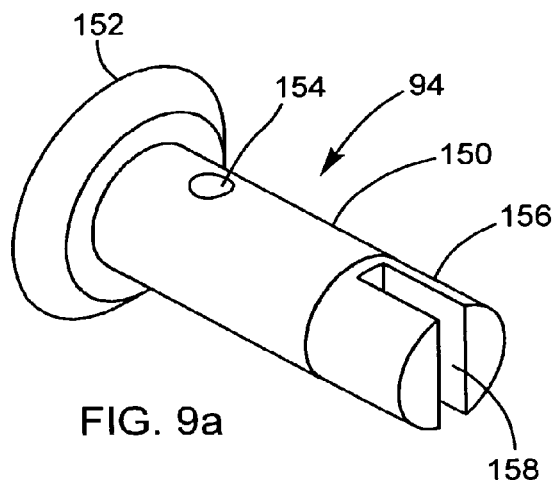
FIG. 9a shows an isometric view of a tensioning screw forming part of the right angle drive.
Figure 9C:
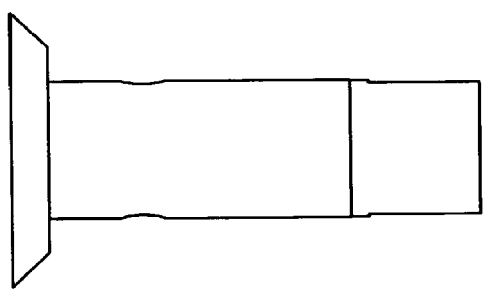
Figure 9D:
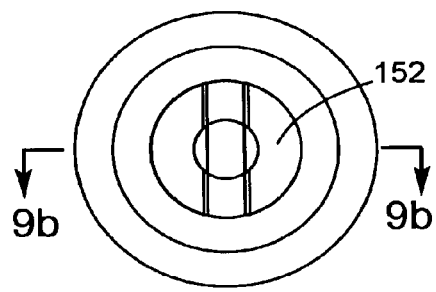

The tensioning screw 96a inserts into hole 144a of output pulley 20, which sits on the shoulder 145a (FIG. 5d) that supports the tensioning screw 96a under loading from the counter-clockwise auxiliary cable 90b. The cable 90b accesses the output pulley 20 through the lateral hole 147 (FIG. 5f), wraps around the tensioning screw 96a for up to three windings, and passes through the hole 154 (FIG. 9a) of the tensioning screw 94a. It is noted that the only difference among screws 94a, 94b, 96a and 96b is the axial location of hole 154. There are two lateral holes 147 on the output pulley 20 for each of the tensioning screws, the choice between the pair will determine the direction of cable winding on the tensioning screws and thus the direction of rotation of the tensioning screws for tightening their respective cable. Turning setscrew 97 (FIG. 11b) in tapped hole 159 (FIG. 9b) of the tensioning screw pinches the cable 90b and deforms the tip of the cable 90b until it is jammed inside the hole 154 and secured by the setscrew 97. To allow room for maneuvering the cable 90b, the entire subassembly of tensioning screw 96a and the setscrew 97 is taken outside of the output pulley 20 after threading the cable through the lateral access hole 147 to complete the cable windings and setscrew securing before being put back to the hole 144a.

Figure 9B:
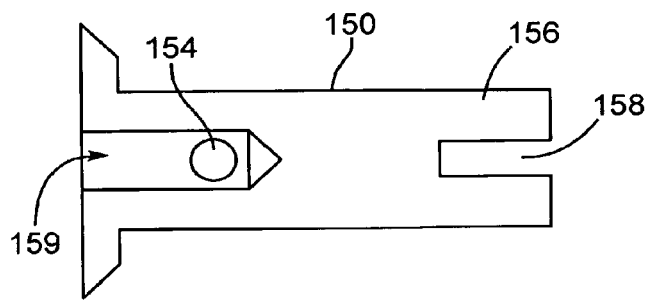
FIG. 9b shows a cross-sectional view along line 9b of FIG. 9d.

Once the cable 90b and the tensioning screw 96a are inside hole 144a, the cable tension can be adjusted by turning the tensioning screw 96a clockwise by means of a screwdriver engaging at the slot 158 of the tensioning screw (FIG. 9b). After the desired cable tension is reached a washer 99 (FIG. 1) and hex nut 100 (FIG. 1) are placed onto the threaded section 156 (FIG. 9b) of the tensioning screw 96a to fix the rotary position of the tensioning screw 96a with respect to the output pulley 20. The cable tension can be guaranteed if the tensioning screw cannot be turned counter-clockwise without loosening up the hex nut. This is accomplished by selecting the lateral access hole 147 from the pair for each tensioning screws on the output pulley 20 such that the tensioning screw will always need to be turned clockwise to tighten the cable tension.

Specifically, if the tensioning screw attempts to turn counter-clockwise due to the cable tension, the washer and hex nut will attempt to rotate as a unit with respect to the output pulley but friction against the front face of the output pulley will resist the rotation and thus any rotation of the tensioning screw 96a will be done with the washer 99 and hex nut 100 remaining static to the output pulley 20, resulting in the hex nut compressing against the output pulley via the tensioning screw and consequently resisting any further counter-clockwise rotation of the tensioning screw 96a. Provided the friction against between the output pulley front face and the washer 99 and the hex nut 100 is greater than that between the internal thread of hex nut 100 and the external thread section 156 of tensioning screw 96a (of FIG. 9a), the cable tension will not loosen up on its own. This can be ensured by the large surface area of the flat washer 99, with which the tensioning screw 96a, the washer 99 and the hex nut 100 will not rotate counter-clockwise as a unit, thereby guaranteeing the tensioning of that particular cable section. The load carried by the right-angle drive is mounted to the front face of the output pulley 20, via the bolt holes 150 and the timing dowel holes 151, shown in FIGS. 5a and 5b. To locate the center-of-rotation of the output pulley 20, the load can use the center dowel 32 of FIG. 1. FIG. 5e shows details of the tensioning mechanism at output pulley 20.

The flexible cables 90b and 92b may be low-stretch/pre-tensioned cables, which may or may not be metallic, to minimize transmission loss due to elastic stretching of the cables.

Figures 7A, 7B:
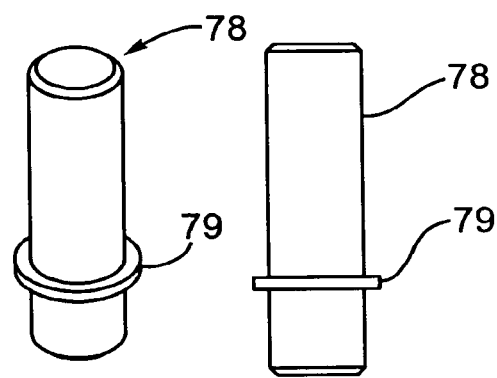
Figure 10A:
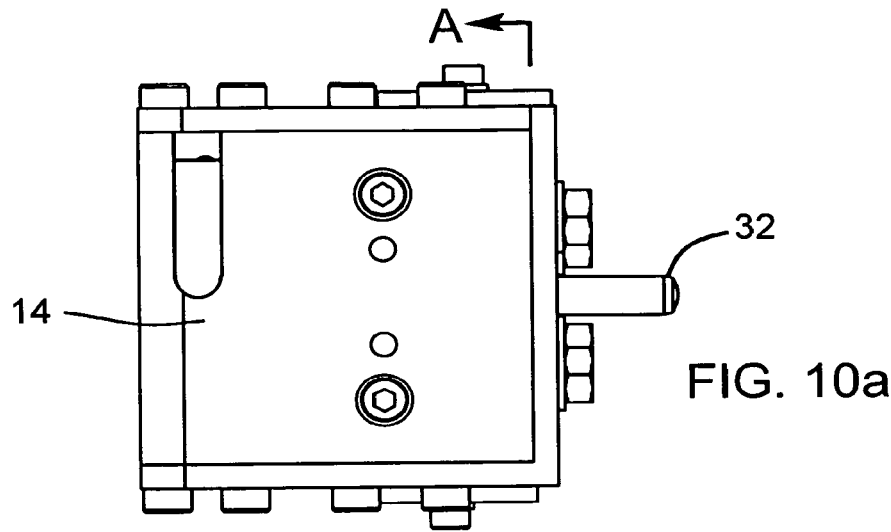
FIG. 10a shows the front view of the assembled right-angle drive.
Figure 10B:
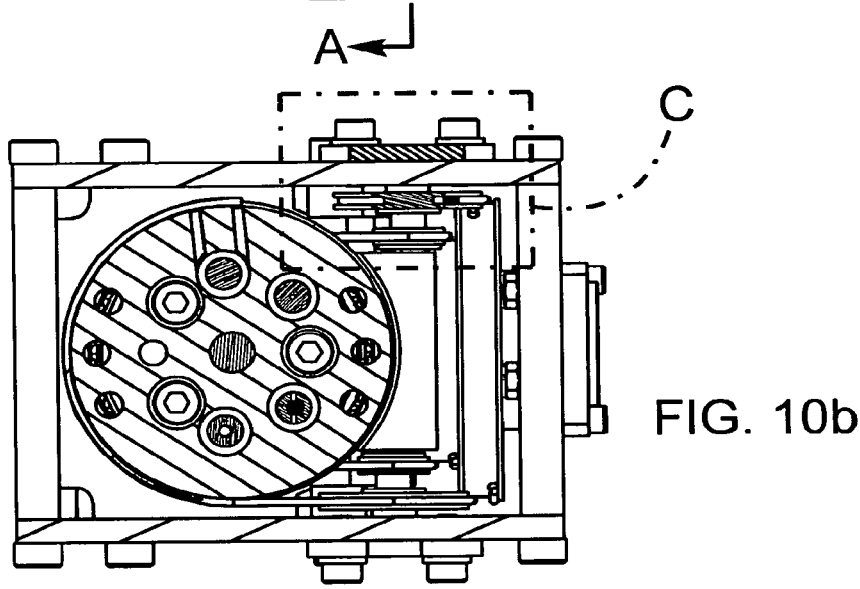
Figure 10C:
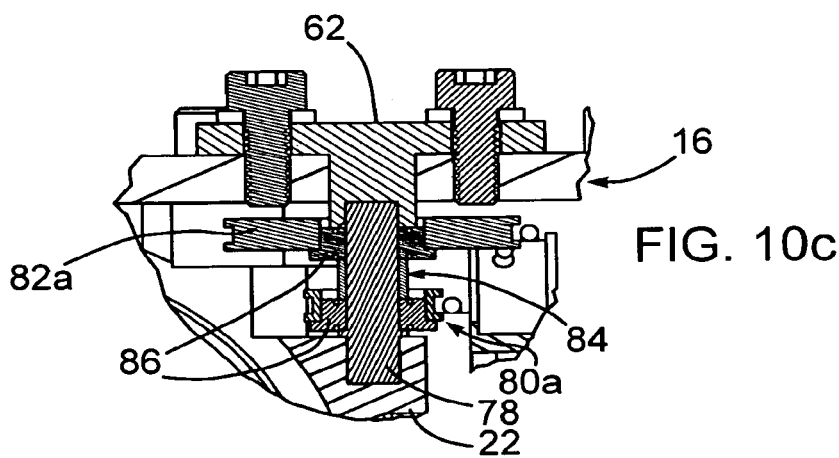
FIG. 10c shows the detailed view of section C in FIG. 10b for the idler subassembly.

Referring again to FIG. 2, the idler mechanisms each include main idlers 80a and 80b, and auxiliary idlers 82a and 82b, and it is noted that main idlers 80a and 80b and auxiliary idlers 82a and 82b may or may not be identical depending on the relative position of the idler shaft 78 with respect to both the input pulley 54 and output pulley 20, and auxiliary idler spacer 84 that separates the main idlers 80a, 80b and auxiliary idlers 82a, 82b, and two flange radial ball-bearings 86 to allow free rotation of both the main idlers 80a, 80b and auxiliary idlers 82a, 82b independent of each other. FIGS. 7a and 7b show the idler shafts 78 which include a circumferential ridge 79 located near one of the ends of the shaft 78 so that the two shafts are inserted into holes 76 a distance equal to the distance from that particular end to the ridge 79, best seen in FIG. 10c. A lock nut 60 is located between the output pulley 20 and the angular-contact ball-bearing 24 located closest to the output pulley 20 for retaining that particular bearing in mid-housing 22, see FIG. 4f.

FIG. 8 shows the relative positions of the input pulley 54 and the output pulley 20. The idler shafts 78 are located in holes 76 of section 74 of mid housing 22, best seen in FIGS. 2 and 4a. In the cable-driven right-angle drive, the input axis 58 defined by the harmonic-drive 56 (see FIG. 15) and output axis 180 defined by the output shaft 26 (FIG. 11b) are aligned perpendicular to each other. The transmission between the input and output pulleys 54 and 20 respectively is carried out by the cable-pulley system including input pulley 54 and output pulley 20, main idlers 80a, 80b and auxiliary idlers 82a, 82b and cables 90a, 90b and 92a, 92b, in which these two sets of cables correspond to the two directions of rotation.

Referring to FIG. 8, (and FIG. 11a for the tensioning screws referred to below) there are a total of four independent cable sets including: 1) auxiliary cable 90a responsible for clockwise rotation of the output pulley 20 which is associated with auxiliary idler 82a and auxiliary tensioning screw 94a; 2) auxiliary cable 90b which is responsible for counter-clockwise rotation of the output pulley 20 which is associated with auxiliary idler 82b and auxiliary tensioning screw 96a; 3) main cable 92a which is responsible for clockwise rotation of the output pulley 20 which is associated with main idler 80a and main tensioning screw 94b; and 4) main cable 92b responsible for counter-clockwise rotation of the output pulley 20 which is associated with main idler 80b and main tensioning screw 96b. Each cable can be independently tensioned, but when used to transmit rotational motion between the input and output shafts the main and auxiliary cable pairs work together for each direction to reduce tension in each cable set. The two sets of cables reduce the cable tension to improve cable reliability and provide redundancy to improve safety should one cable break.

Referring again to FIG. 8, when the input pulley 54, driven by the output flange 98 of the harmonic-drive 56, rotates counter-clockwise (when looking at the back of the harmonic-drive 56), the counter-clockwise main cables 92b and auxiliary cable 90b are under tension from the end through the lateral access holes 141b, 141a (FIG. 6a) respectively with the terminations at the crimped fittings 101 situated inside the pockets 138a, 140a respectively on the input pulley 54, being diverted into a right-angle change of direction by the main idlers 80b and auxiliary idlers 82b, and pulls on other end of the cables at the setscrew 97 termination (FIG. 5e) on the main tensioning screws 96b and auxiliary tensioning screws 96a and hence cause the output pulley 20 and dowel 32 connected to output shaft 26 to rotate counter-clockwise looking at the front face of the output pulley 20. Whereas the other set of cables unwind in the opposite direction since clockwise main cable 92a and auxiliary cable 90a, beginning at the input pulley 54 at the crimped fittings terminations 101 through the lateral access holes 141d and 141c (FIG. 6a) respectively, are diverted into a right-angle change of direction by the main idler 80a and auxiliary idler 82a, and are terminated on the output pulley 20 at the setscrew 97 on the main tensioning screws 94b and auxiliary tensioning screws 94a.

Cables 90a, 90b and 92a, 92b are preferably low-stretch/pre-tensioned cables to minimize motion loss due to elastic deformation of the cables under tension. Referring to FIGS. 1, 2, 10b and 10c, when assembled, idler caps 62 and 64 are bolted to the top and bottom of housing cover 16 which support the idler shafts 78 on their free ends opposite to those at the holes 76 on the mid-housing 22. The Idlers 80a, 80b and 82a, 82b mounted on the idler shafts thus can maintain their radial positions with respect to the input pulley 54 and output pulley 20 even when the cables are under tension.

Figure 13:
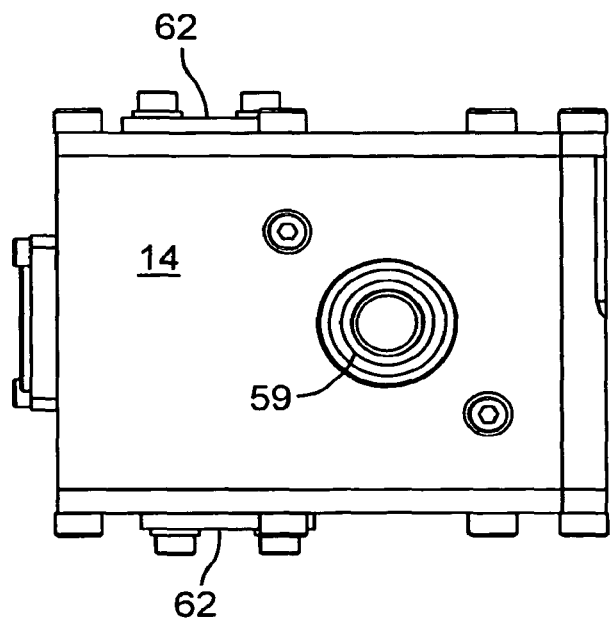

FIG. 13 shows a view from the back of the drive unit opposite to the output face from which dowel 32 projects. As can be seen, bearing 59 rotates in hole 61 (of FIG. 2) located in the back wall of chassis 14.

Figure 14:
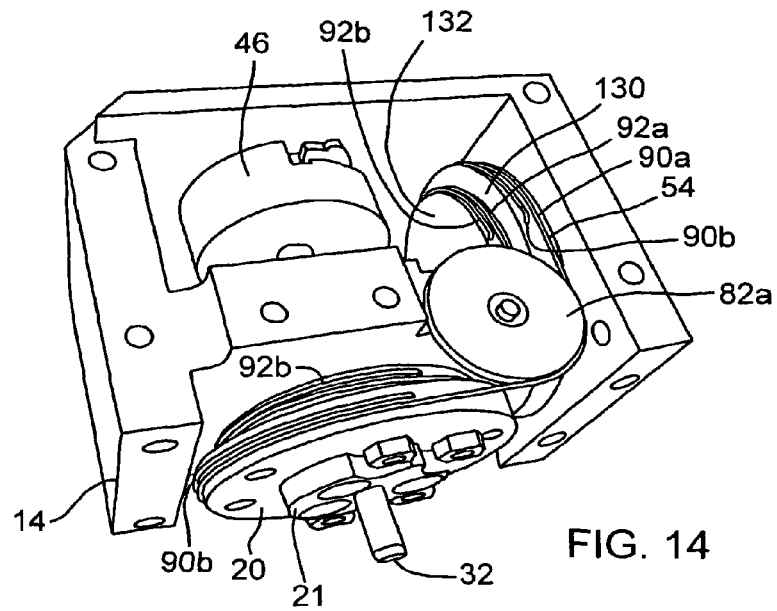
FIG. 14 shows a perspective view from a top-front angle of the assembled right-angle drive of FIGS. 1 and 2 without the cover and idler caps.
Figure 15:
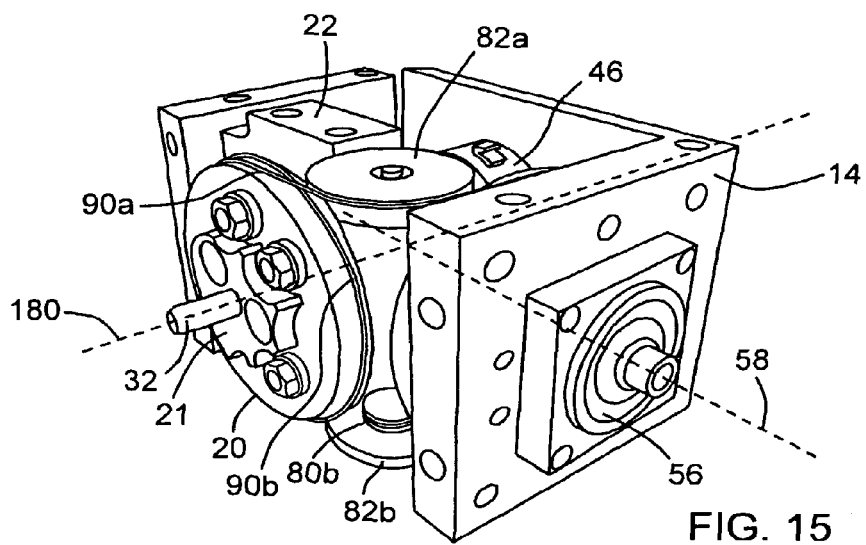
FIG. 15 shows a perspective view from a top-rear angle of the assembled right-angle drive without the cover and idler caps.

FIGS. 14 and 15 show isometric views of the drive unit without the cover 16 thereby showing the placement of the cable drive system, shown in FIG. 8, now placed in the chassis 14. There is a slight difference in structure of the output pulley 20 of the right-angle drive in FIGS. 14 and 15 compared to right-angle drive 10 in FIG. 1. In FIGS. 14 and 15, the output pulley 20 includes a raised guide 21 integrally formed on the outer surface of pulley 20. The right-angle drive shown in FIGS. 14 and 15 is larger than the right-angle drive 10 in FIG. 1 because it is used in both the shoulder-pitch joint as the right-angle drive 406 and the elbow-pitch joint as the right-angle drive 410.

Figure 18C:
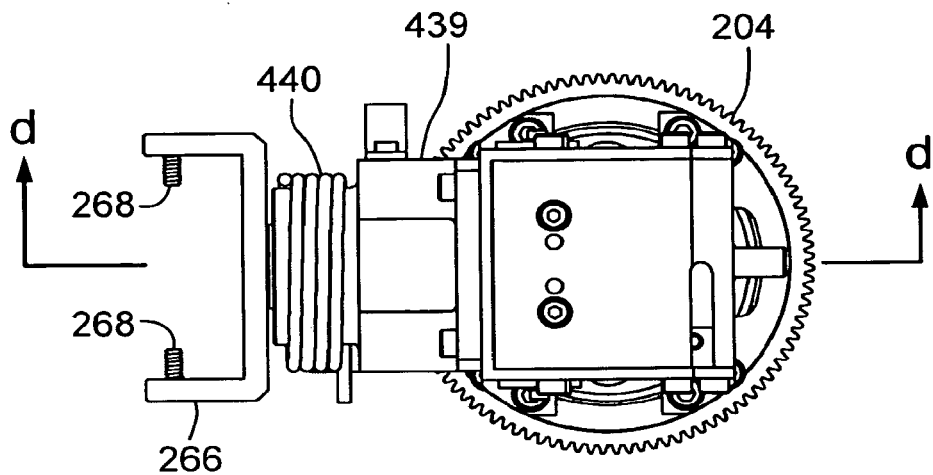
Figure 18D:
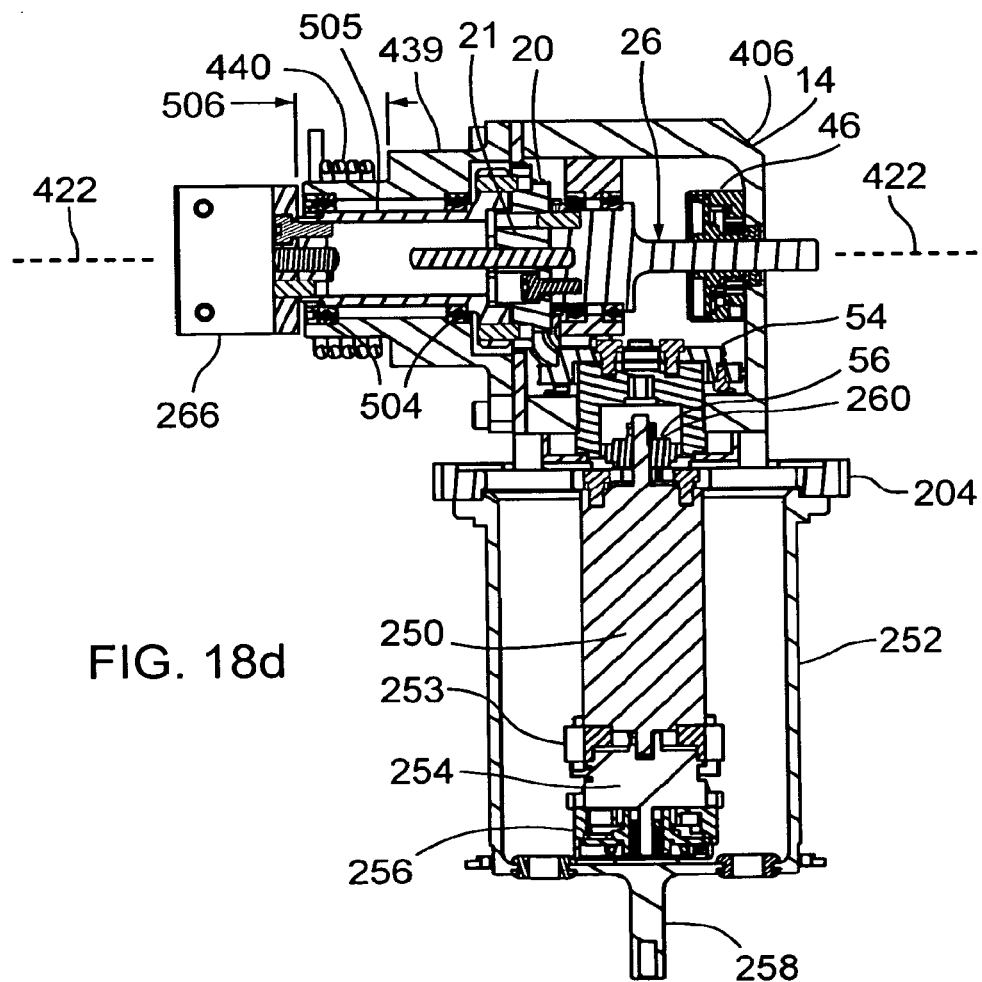
Figure 19A:
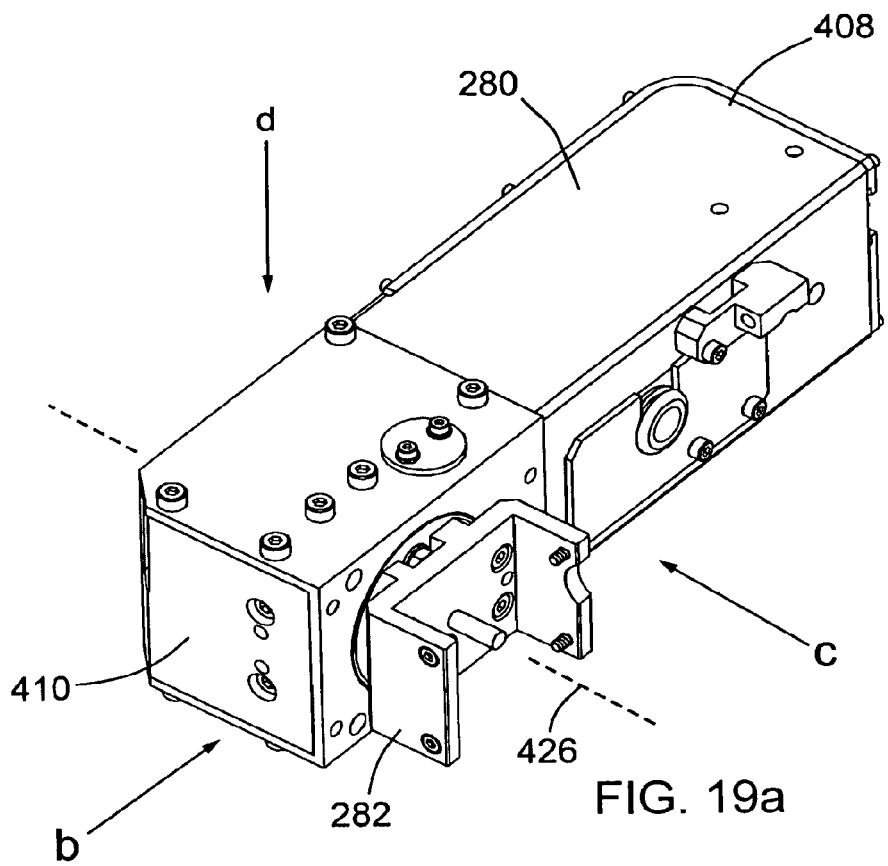
FIGS. 19a to 19e show details of the manipulator lower arm and the right angle drive mounted at the front of the manipulator lower arm forming an elbow-pitch joint assembly.
Figure 19B:
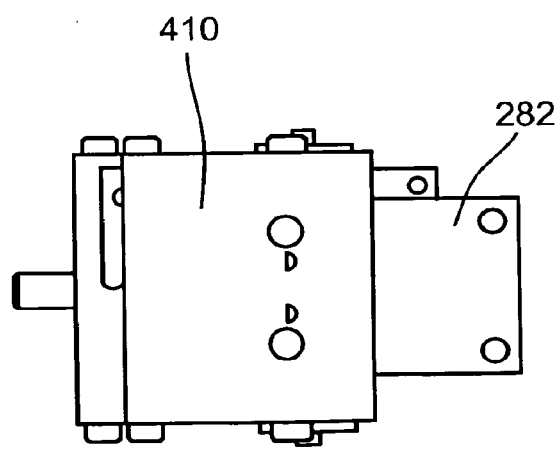
Figure 19C:
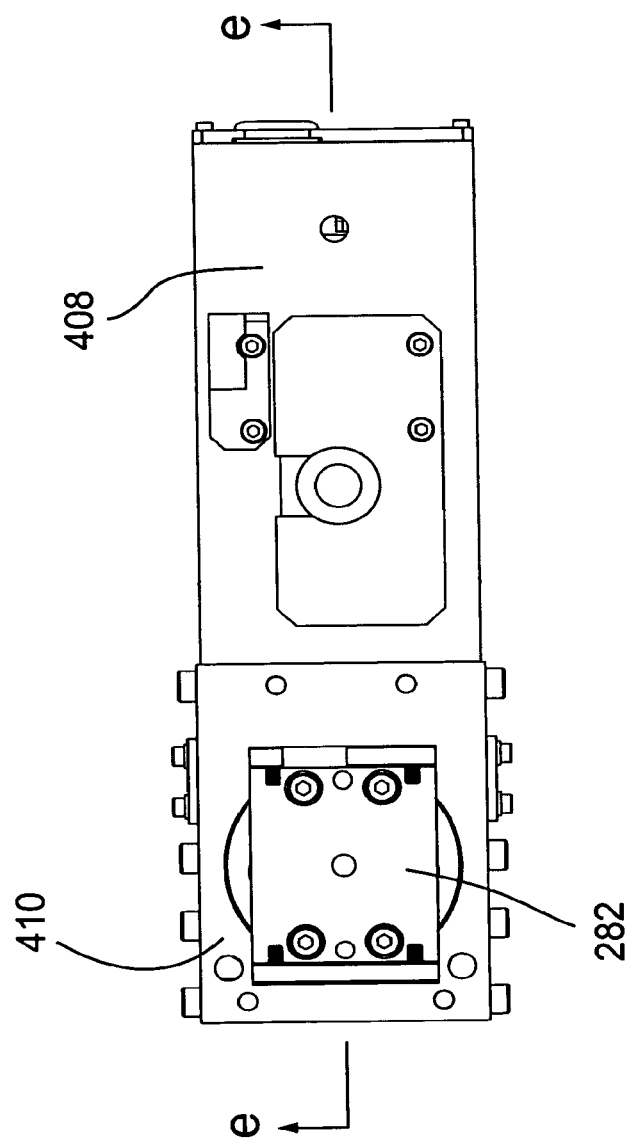
Figure 19D:
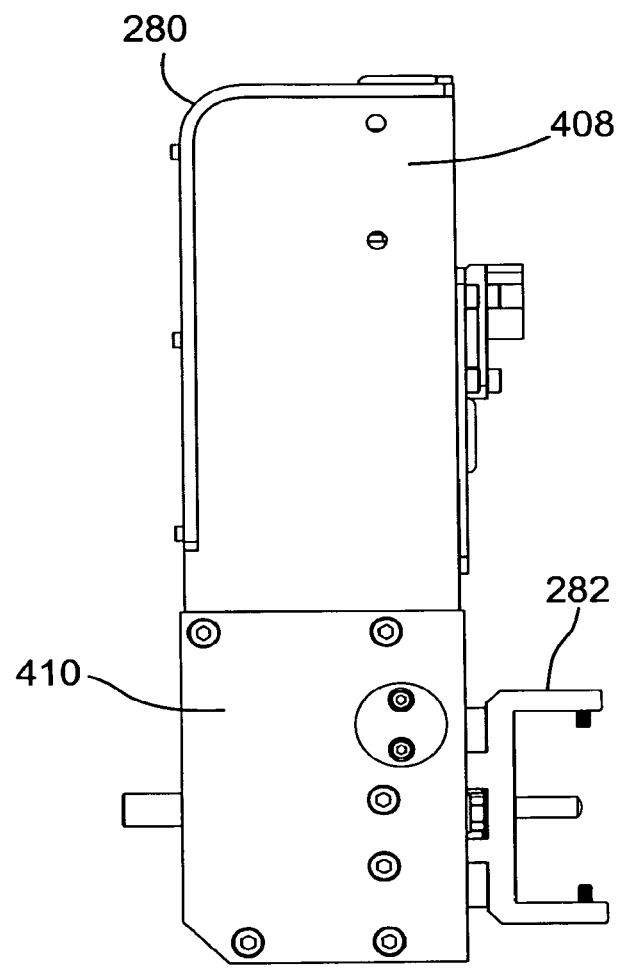
Figure 19E:
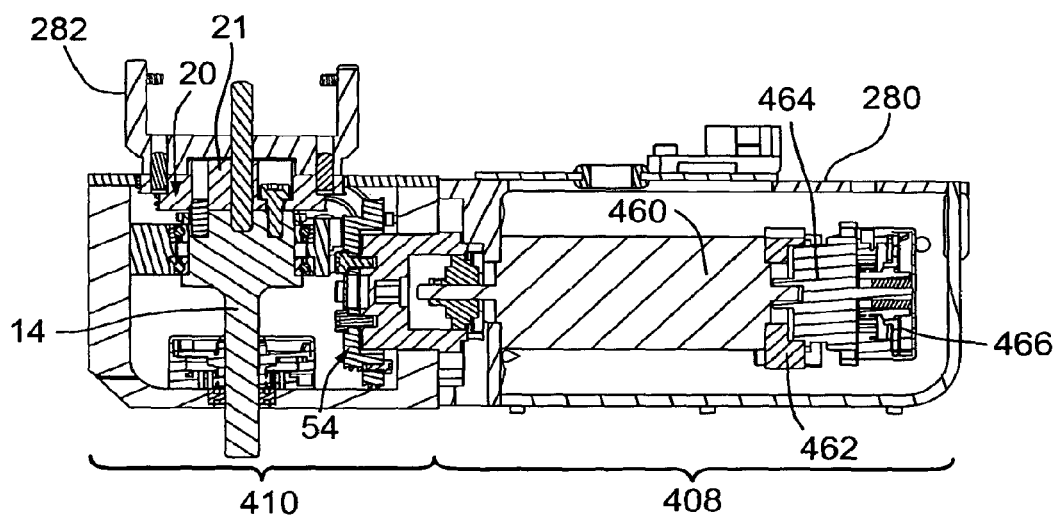
Figure 20A:
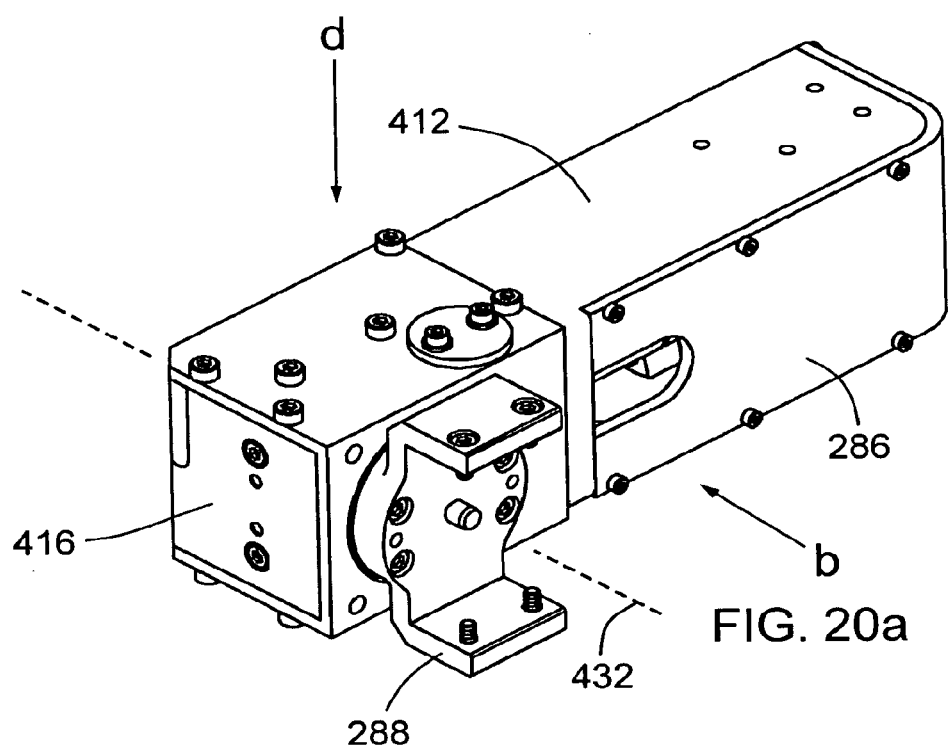
Figure 20B:
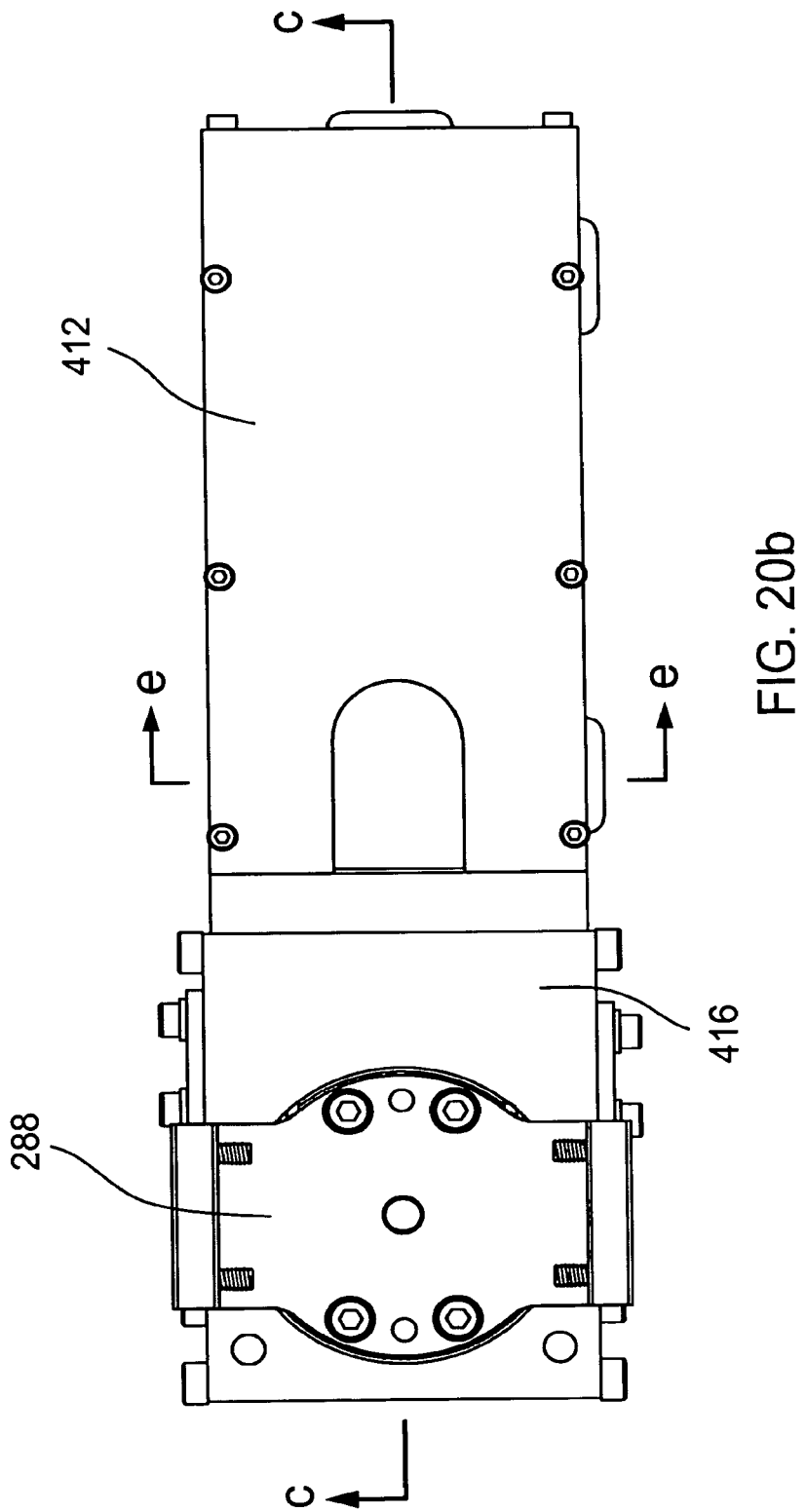
Figure 20C:
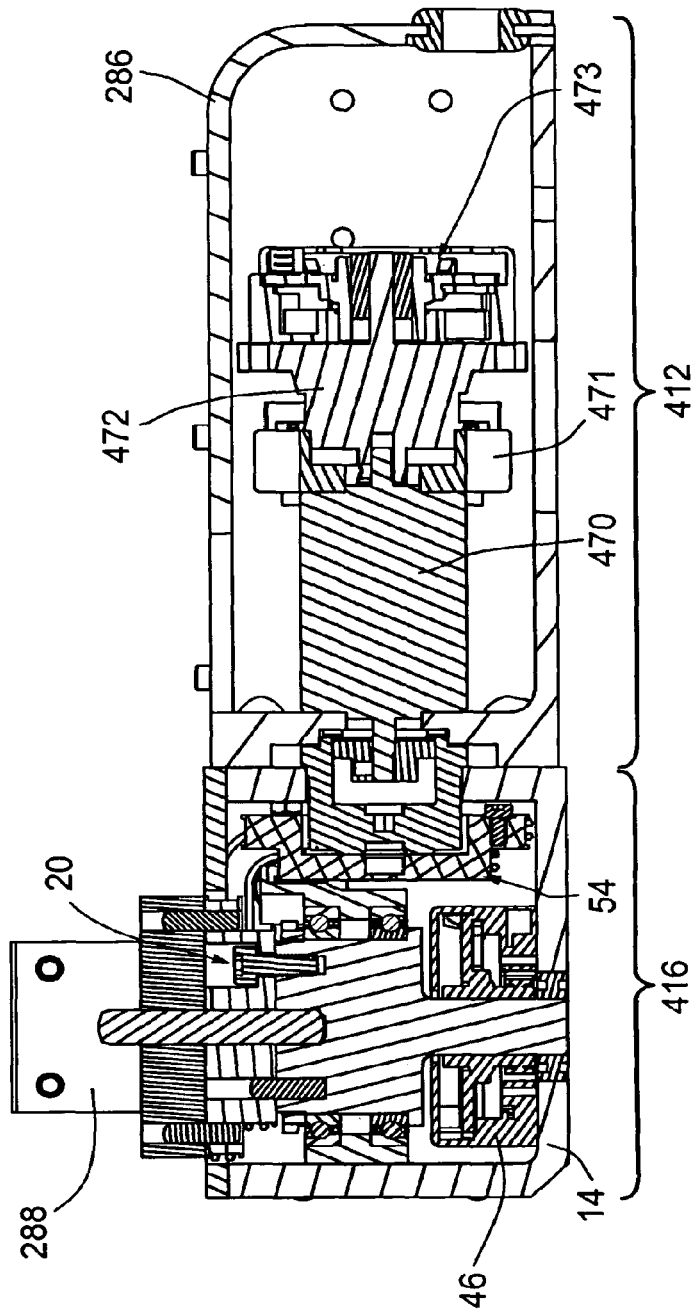
Figure 20D:
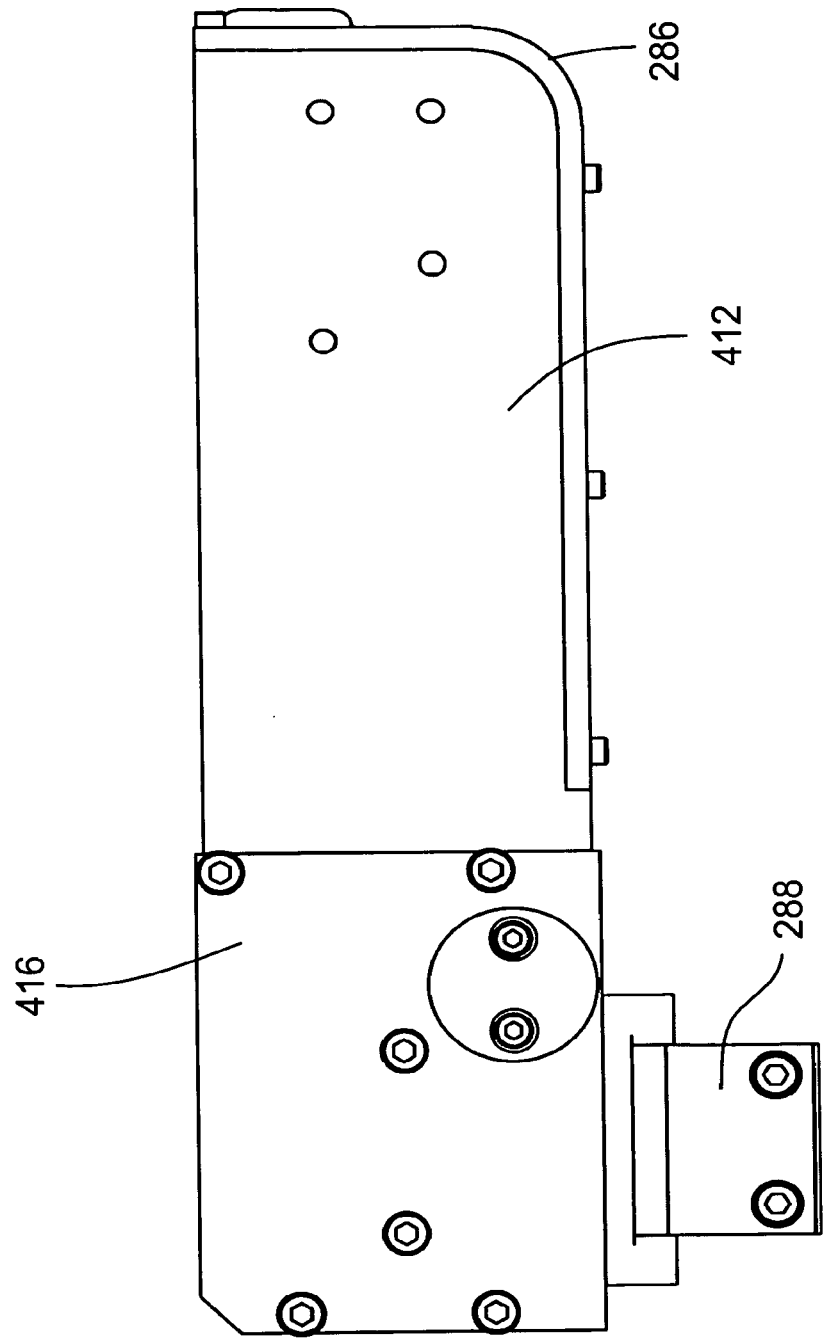
Figure 20E:
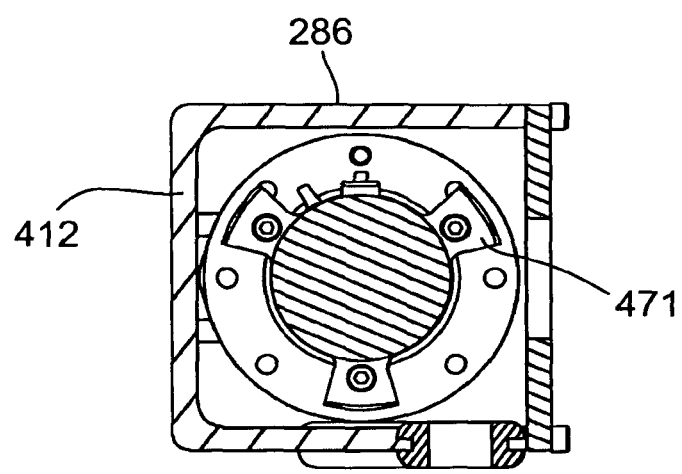

The load at the elbow-pitch and shoulder-pitch joints are substantially higher than that at the wrist-pitch joint due to the difference in component weight each joint is carrying, hence the pulleys 20 and 54 need to be enlarged to compensate for the higher torque so the stress in the driving cable sets 90a, 90b, 92a, 92b can be reduced. Thus the overall size of the right-angle drive 10 in FIG. 1, while applicable to the wrist-pitch joint, is required to be increased as a result for the elbow-pitch and shoulder-pitch joints to become the variation shown in FIGS. 14 and 15. The excessive loading at the shoulder-pitch joint compared to that at the elbow-pitch joint is partially compensated for by the counterbalance torsion spring 440 as shown in FIG. 18d. Referring to FIG. 18d, the raised guide 21 on output pulley 20 of right-angle drive unit 406 is used for guiding the internal axle 505 of the shoulder support 439 to be coupled with the output pulley 20, forming a combined drive shaft to rotate the output bracket 266. The raised guide 21 on the output pulley 20 of the right-angle drive unit 410 for the elbow-pitch joint is not used (FIG. 19e).

The cable driven right-angle drive 10 disclosed herein has several advantageous features. Specifically, it is a low-to-medium load, lightweight unit which may be retrofitted into the joints of existing modular robotic arm systems. The use of the drive cables 90a, 90b and 92a, 92b provide a backlash-free bidirectional rotation. The drive, by incorporating harmonic-drive 56, provides a back-lash free motor input. The drive unit is compact and lightweight, and has an in-line or offset input/output configuration. In an in-line configuration the input and output axes are coplanar whereas in an offset configuration the planes of the input and output axes are parallel but offset in direction normal to the planes. The relative alignment error between the input and output axis can be compensated by the tensioning of the cables. The unit uses redundant cables for safety, uses a simple cable tensioning mechanism and is highly cost-effective since it is of simple construction and does not require expensive gearing and alignment.

In another embodiment of the pulleys 20 and 54, both the input and output pulleys can have any number of differential diametrical sections other than the two shown for this design. Provided there would be a pair of idler pulley subassembly to go with each section of cable transmission, more sections of cable transmission can be introduced to the input and output pulleys as long as the other physical constraints are satisfied. Additional sections of cable will provide more security to the overall integrity of the transmission, but the size of the module will inevitably be increased.

A gear ratio may be introduced using a miniature harmonic gear located at the input pulley, and the load is mounted directly on the front face of the output pulley. Additional devices such as angular motion sensors and motor brakes may be fitted onto the output pulley drive shaft to make a compact module. The module can be sized to the targeted load capacity using off-the-shelf components readily available in various sizes from multiple vendors.

Thus, the present invention provides a compact yet highly efficient module for right-angle transmission by combining cable-pulley systems and harmonic drive technology. The cable-pulley drive system provides high fidelity while the harmonic drive contributes to the high power density and back-drivability. In light to medium duty load applications, this module will enable miniature actuators and sensors while outperforming conventional bevel or worm gearing. The mechanism itself is simple yet robust, highly modular and flexible in interfacing. Redundant cables add safety to the design and the accessibility of the input and output transmission axes facilitate integration of auxiliary devices into a compact integrated unit. The design has simple components and does not need expensive gear cutting technology. No other existing technology can compete in terms of positional accuracy, size and weight, efficiency, modularity, ease of reconfiguration, integration and maintenance.

Thus, the present invention provides a right-angle drive which exhibits little or no backlash, simple and robust design, highly repeatable precision, high efficiency, back-driveability, a high gear ratio, compact size and lightweight for a right-angle drive.

While a preferred embodiment of the present invention is the right-angle drive where the input pulley 54 and output pulley 20 rotate in planes that are perpendicular to each other so that the rotational motion of the input shaft is converted to rotational motion about an axis perpendicular to the input rotational axis, it will be understood that other angles are possible. Particularly, the housing chassis 14, cover 16, mid-housing 22 and the other components can be made to accommodate any fixed angle between the input and output axis as long as the cable routing is not compromised. Thus, while the preferred nominal angle between input and output is 90 degrees, it will be appreciated that other angles are possible. In addition, because flexible cables are being used in which the tension can be adjusted, it will be appreciated that the user can reconfigure the housing to adjust the input and output axis at the preferred angle so that as the input and output pulleys are locked in position to give the desired angle, the cable tension of each cable is adjusted accordingly to either take up the slack in the cables caused by repositioning the input and output pulleys with respect to each other.

For example, one method to facilitate tensioning of the screws for different angles is to have the tensioning screws continuously torqued by a built-in spring. The screw may also have a ratchet to prevent counter-rotation of the tension screw making the rotation unidirectional. Therefore any "slack" in the cable may be removed by the spring and the ratchet prevents further, slackening. The spring is selected to have sufficient torque to tension the cable adequately. The spring or a ratchet can both provide cable tensioning, regardless of whether the input and output pulleys are configured for right-angle transmission or some other angle. With a spring, the cable is constantly under tension without any manual adjustment, but a very strong spring is preferred for tensioning. A ratchet mechanism also gives unidirectional rotation, that is, the direction to further tighten the cable tension, such that it is guaranteed no cable loosening will happen under normal circumstances.

A difference between a ratchet tensioning mechanism and the cable tension mechanism shown in FIG. 5e, is that the ratchet mechanism is a discrete system, meaning that the number of "locking" rotary positions the screw can sit at depends on the number of teeth on the ratchet, whereas the screw/nut tensioning mechanism illustrated in FIG. 5e has an infinite number of positions possible for "locking" purpose once the cable tension is set. The screw/nut tensioning requires manual adjustment, whereas automatic tension adjustment is possible using a ratcheting mechanism. Thus spring or ratchet or screw/nut mechanisms are all possible embodiments of the cable tensioning device.

2) Surgical Manipulator

Figures 16A, 16B:
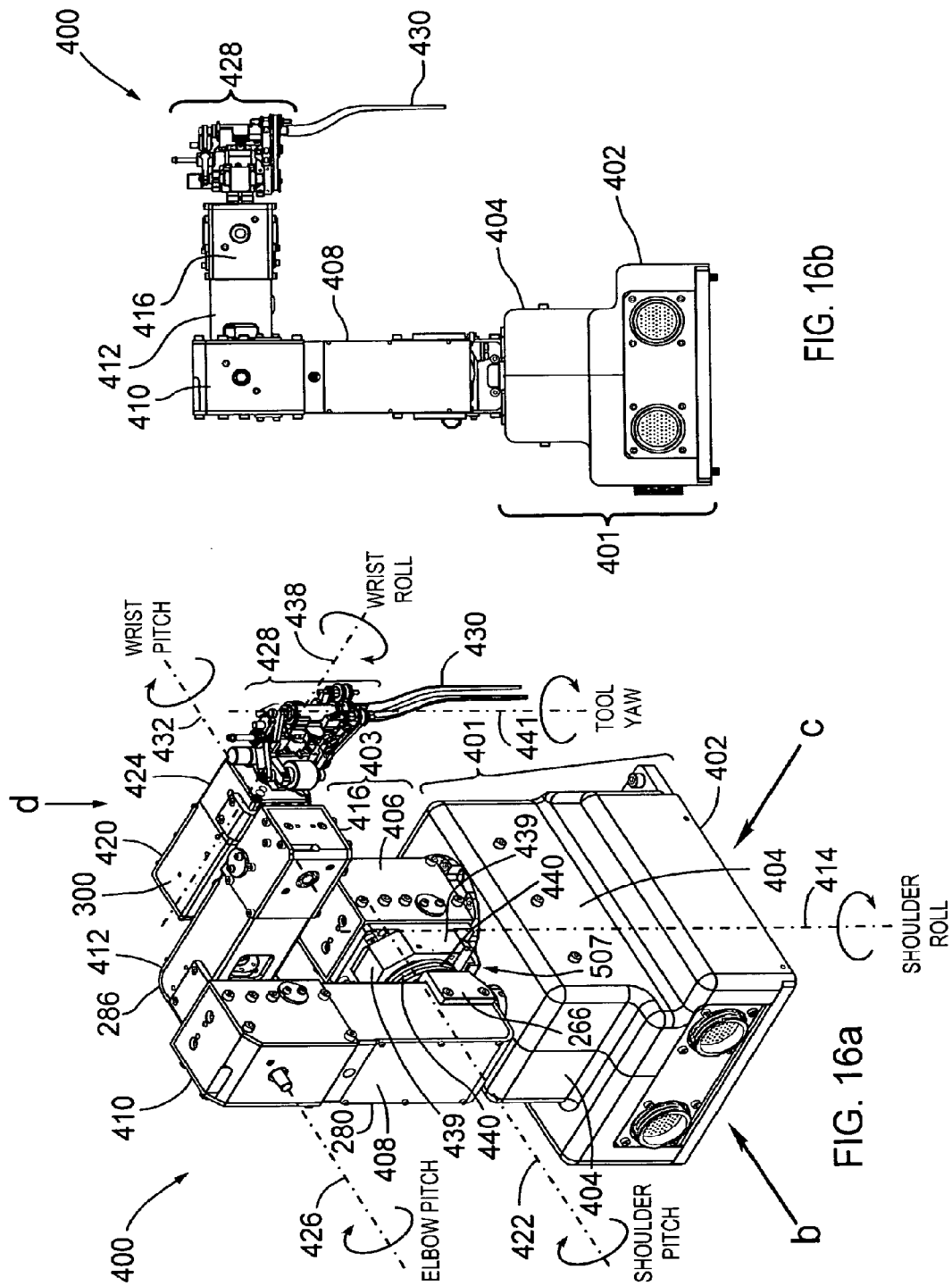
Figure 16C:
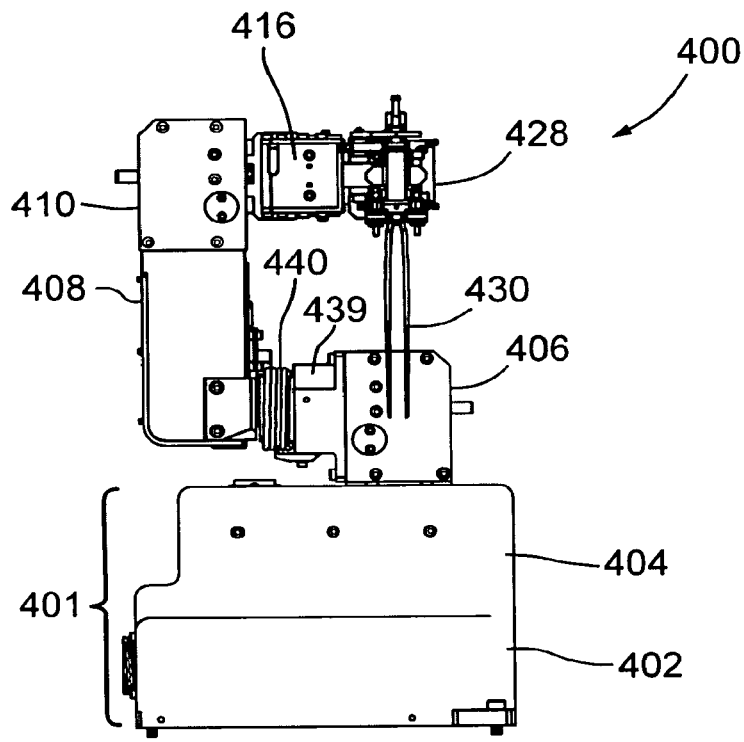
Figure 16D:
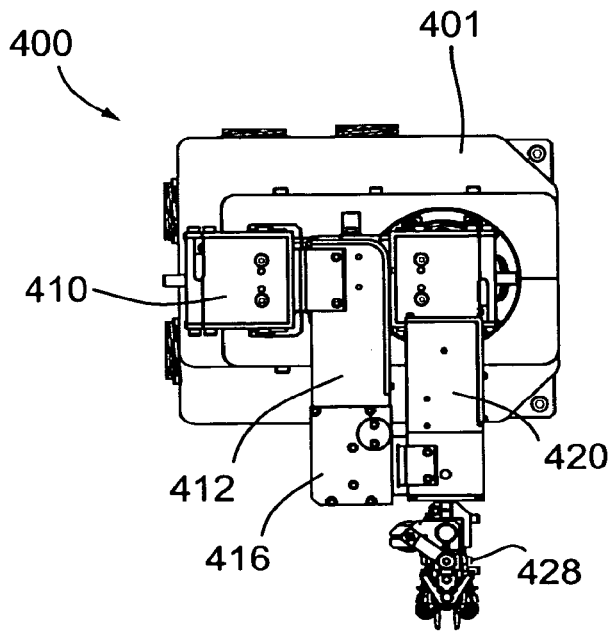
Figure 16E:
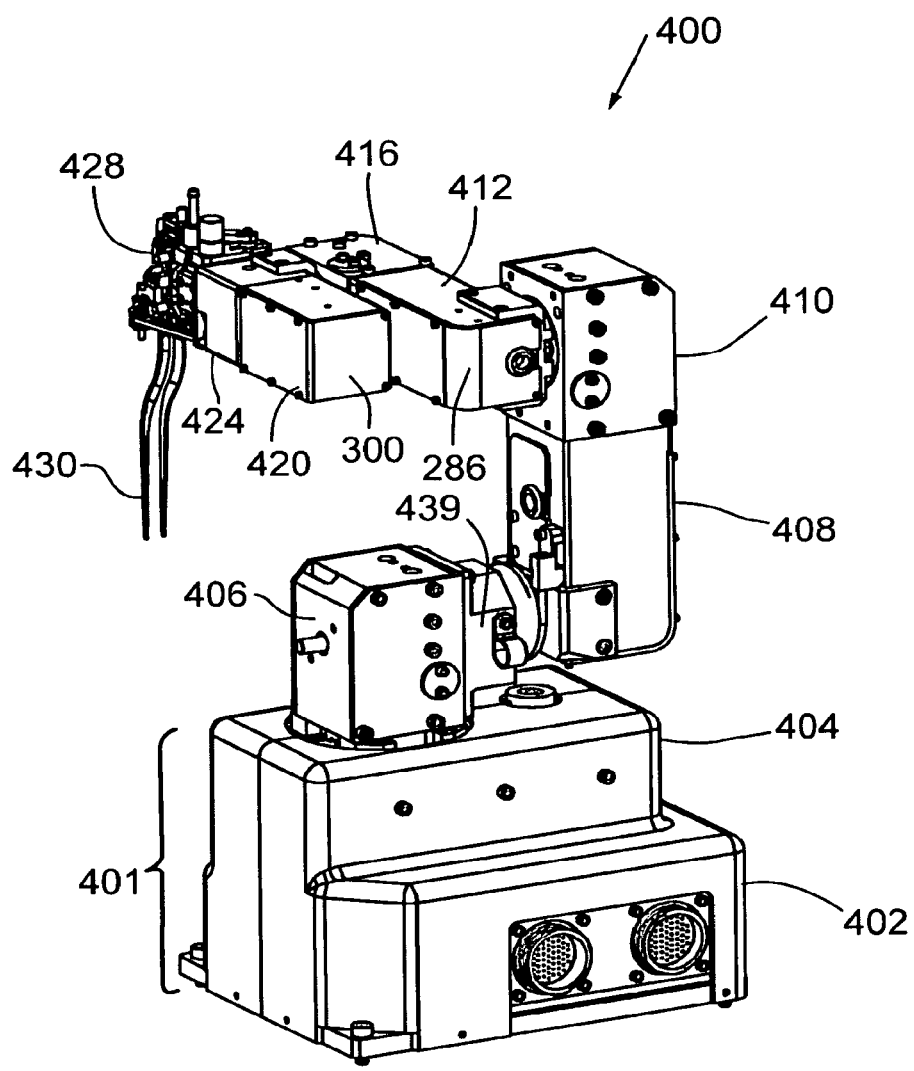
FIG. 16e is another an isometric view of the surgical manipulator similar to FIG. 16a but looking from the opposite direction.

FIGS. 16a to 21e show the surgical manipulator arm 400 in its entirety and all the various components making up the arm. FIG. 16a shows an isometric view of a six degrees-of-freedom surgical robot shown generally at 400 forming part of the present invention. FIGS. 16a and 16e show two different isometric views of manipulator 400 while FIGS. 16b, 16c and 16d show back, side and top views respectively of manipulator 400. The basic exterior structure of manipulator 400 will be discussed with respect to FIGS. 16a to 16e and details of the internal structure of each of these components will be discussed with respect to FIGS. 17a to 21e.

Referring to FIG. 16a, the base 401 of the surgical robot 400 contains the shoulder-roll joint with axis 414 and part of the shoulder-pitch joint with axis 422. Referring to FIGS. 17a to 17e, manipulator shoulder base 401 includes a mounting plate 200 for table-top installation, a support housing 202 mounted on base plate 200 for both the shoulder-roll and shoulder-pitch joints, and a driven spur gear 204 for rotation about axis 414 (also shown in FIG. 16a) which together with shoulder-pitch housing 252 (FIG. 17c) form part of the shoulder-pitch joint (refer to description in the next paragraph). The shoulder-pitch housing 252 is mounted inside support housing 202 by a pair of angular-contact ball bearings 500, with an optical encoder 503 coupled to the extension 258 of the housing 252 to measure the shoulder-roll joint output position. Straight-tooth spur gear 204 is rotationally driven by a smaller-sized pinion 206 with which it is meshed. The pinion 206 is an anti-backlash gear with springs 216 that eliminates gaps between mating gear teeth when meshing with the driven gear 204. Via the hub 214 and subsequently the shoulder-roll drive shaft 220, pinion 206 is mounted to, and driven by, a motor 212 mounted below gear 206 and secured to housing 202. A gear ratio exists between the gear 204 and pinion 206 which depends on the difference in their respective diameters. The motor 212 is a combination of harmonic-drive, an optical incremental encoder (measuring input motor position) and a DC brushless motor. The harmonic-drive 56 supplies additional gear ratio between the motor 212 input to the resulting output motion at the drive shaft 220 to further reduce the speed of the gear 204.

Figure 17A:
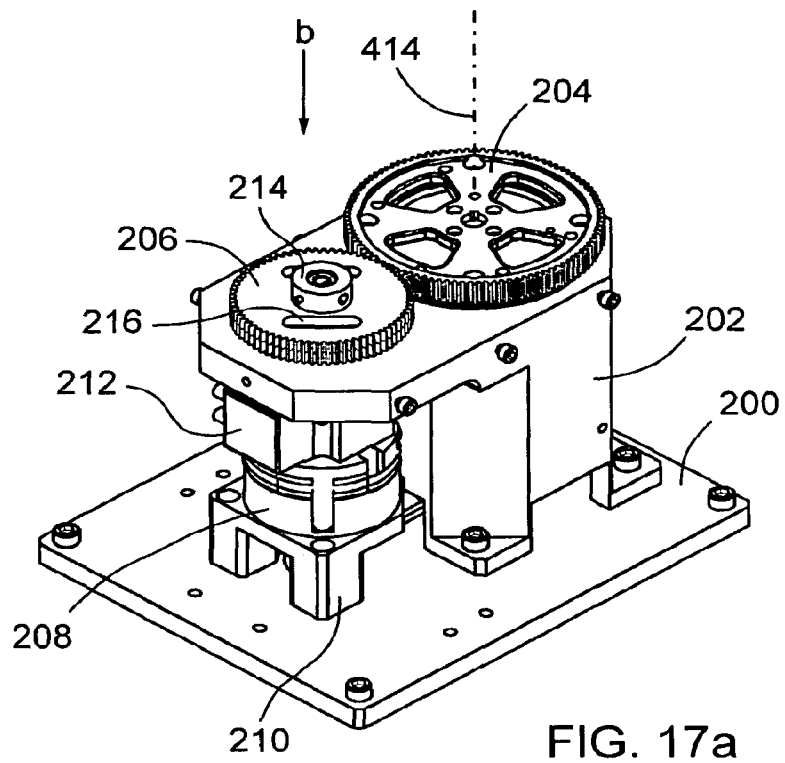
FIGS. 17a to 17e show details of the manipulator base forming a shoulder-roll joint assembly.
Figure 17B:
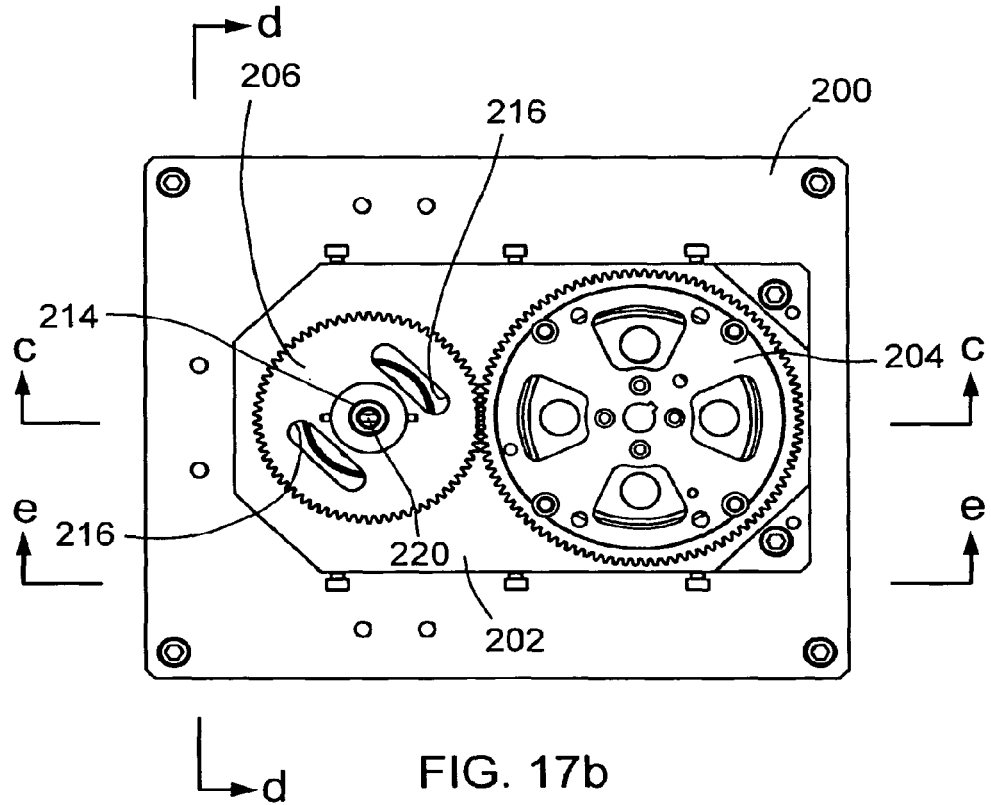
Figure 17C:
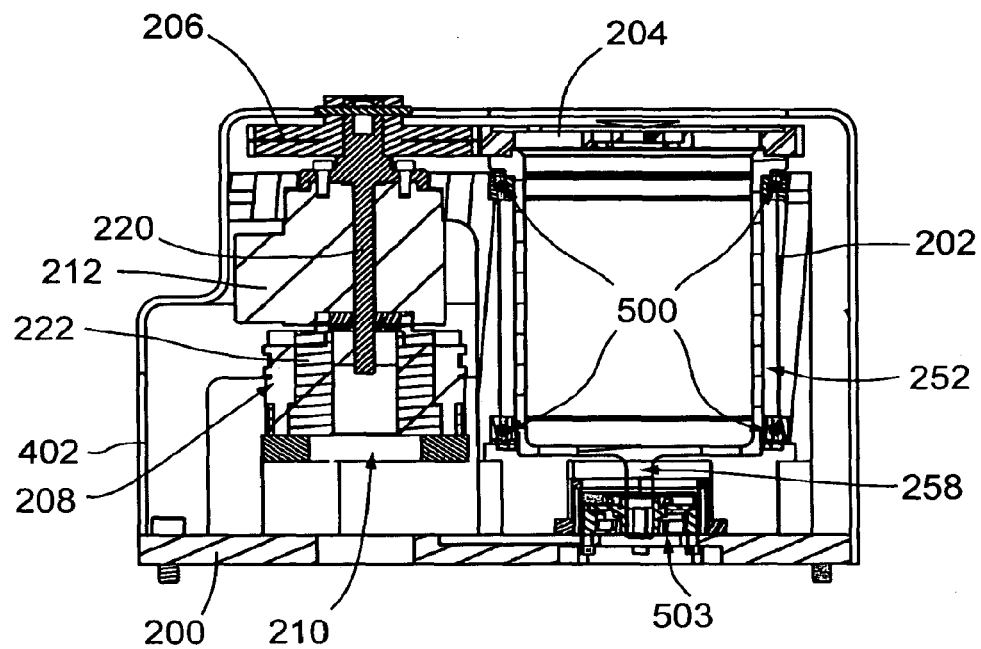
Figure 17D:
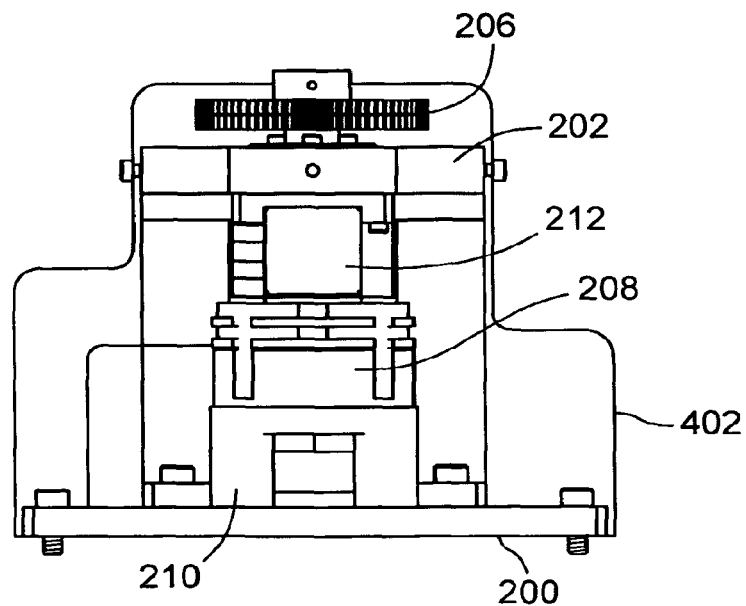
Figure 17E:
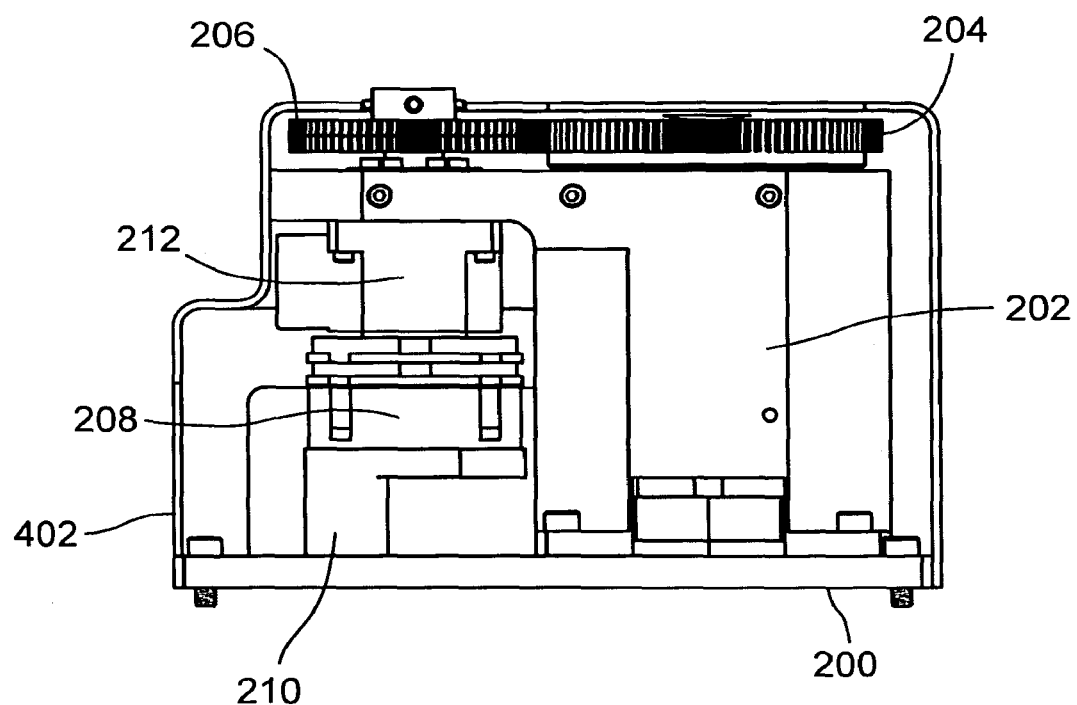

Referring to FIG. 17c in particular, to provide fail-safe braking, a power-off brake 208 is coupled to the motor 212, at which the armature of the brake 222 is connected to the shoulder-roll drive shaft 220 just below the motor 212. The brake 222 is mounted onto the brake support 210, which is then secured on the mounting plate 200. Upon braking or emergency stop situation, power supplied to the brake 208 will be cut, the armature 222 of the brake 208 will stop rotating by the magnetic field generated inside the brake 208, and thus the drive shaft 220 will cease all motion and the entire shoulder-roll joint can be stopped as a result.

Motor 212 may include a servo motor integrated with a harmonic gear and an angular encoder for measuring rotational displacement of the motor shaft 220 coupled to said pinion gear.

Referring to FIGS. 18a to 18e, the shoulder-pitch joint includes a right-angle drive 406 which is mounted on top of upper base 404 (FIG. 16a). The structure and operation of the right angle drive shoulder-pitch joint 406 has been described above in the section entitled Right-Angle Drive. The spur gear 204 and the shoulder-pitch housing 252 form part of the shoulder-roll structure, as described in the previous paragraph. Referring to FIG. 18d, the spur gear 204 acts as the interface between the right-angle drive 406 and the input actuating components, which include a DC brushless motor 250, with an interface plate 253 at the rear at which a power-off electro-magnetic brake 254 is attached, and an incremental optical encoder 256 mounted to the brake 254 directly which measures the motor input position.

Upon braking, the power-off brake 254 will act in a similar fashion as its counterpart in the shoulder-roll joint in that the motor 250 rotation will be stopped via the connected rear end of the motor output shaft. The front end of the output shaft of the motor 250 is connected to the harmonic-drive 56 of the right-angle drive 406, which rotates the input pulley 54 and drives the output pulley 20, as described in the Right-Angle Drive section. At the output side of the right-angle drive 406, the shoulder support 439 is mounted to the chassis 14 of the drive 406, which has an internal axle 505 supported by a pair of angular-contact ball bearings 504 and coupled with the output pulley 20 of the right-angle drive 406. At the outside end of the axle 505, a mounting bracket 266 is mounted, at which the lower arm of the manipulator 408 is attached to, resulting in the lower arm 408 (FIG. 16a) rotating about the shoulder-pitch axis 422.

Figure 18E:
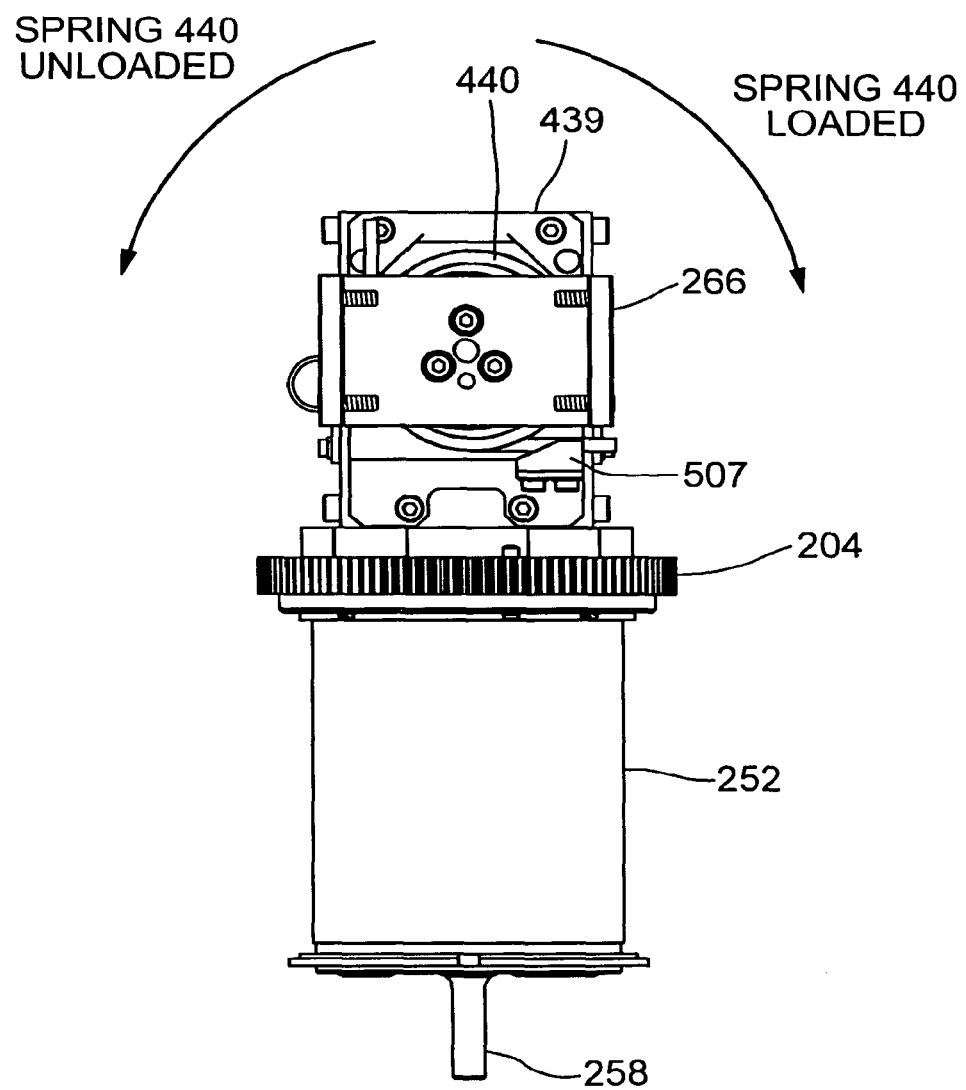

To assist the motor 250 in moving the lower arm 408 and the remaining components attached above it about the shoulder-pitch joint against gravity, a torsion spring 440 (FIGS. 16a, 18b and 18e) is mounted on the shoulder support 439 and the lower arm 408 which serves as a counterbalance as the lower arm 408 rotates in the indicated direction about the shoulder-pitch axis 422. Referring to FIGS. 18b, and 18e in particular, the counterbalance spring 440 has one leg supported by a bracket 507, while the other leg rotates together with the lower arm 408 (seen in FIG. 16a). The spring 440 will be loaded only when the lower arm 408 is rotating forward, as illustrated along the direction of the arrow in FIG. 18e. All components attach to bracket 266 rotates as a unit about axis 414 (seen in FIG. 16a) for the shoulder-roll joint.

Referring to FIGS. 16a, 16e, 19a to 19e, attached to the upper end of the lower manipulator arm 408 is an elbow-pitch right-angle drive 410 of the same structure and operation as that of the shoulder-pitch joint as described in the previous paragraph. An upper arm 412 is mounted to the bracket 282 on top of the output pulley 20 (FIG. 19e) of the elbow-pitch joint right-angle drive 410 so that the rotational motion of the input pulley 54 (FIG. 19e) to the drive unit 410 is translated into rotational motion of the upper arm 412 about the elbow-pitch axis 426. As seen in FIG. 19e, a DC brushless motor 460, an interface plate 462 with the power-off brake 464, and the incremental optical encoder 466 residing inside housing 280 are identical to their counterparts in the shoulder-pitch joint 250, 253, 254 and 256 respectively (FIG. 18d) both in configuration and operation.

Referring to FIGS. 16a, 16e, 20a to 20e, attached to the upper end of the manipulator fore arm 412 is a wrist-pitch right-angle drive 416 of similar structure and operation as that of the elbow and shoulder-pitch joints but smaller in size. A wrist 420 (FIGS. 16a) is mounted to the bracket 288 on top of the output pulley 20 (FIG. 20c) of the wrist-pitch joint right-angle drive 416 so that the rotational motion of the input pulley 54 (FIG. 20c) to the drive unit 416 is translated into rotational motion of the wrist 420 about the wrist-pitch axis 432. The internal configuration of the fore arm 412 is similar to that of the lower arm 408, in which the DC brushless motor 470, interface plate 471 with the power-off brake 471 residing inside housing 286 are similar to their counterparts 460, 462 and 464 of the lower arm 408 but smaller in size and having the same operating principle. The incremental encoder 473 is identical to the encoder 466 of the lower arm 408.

Figure 21A:
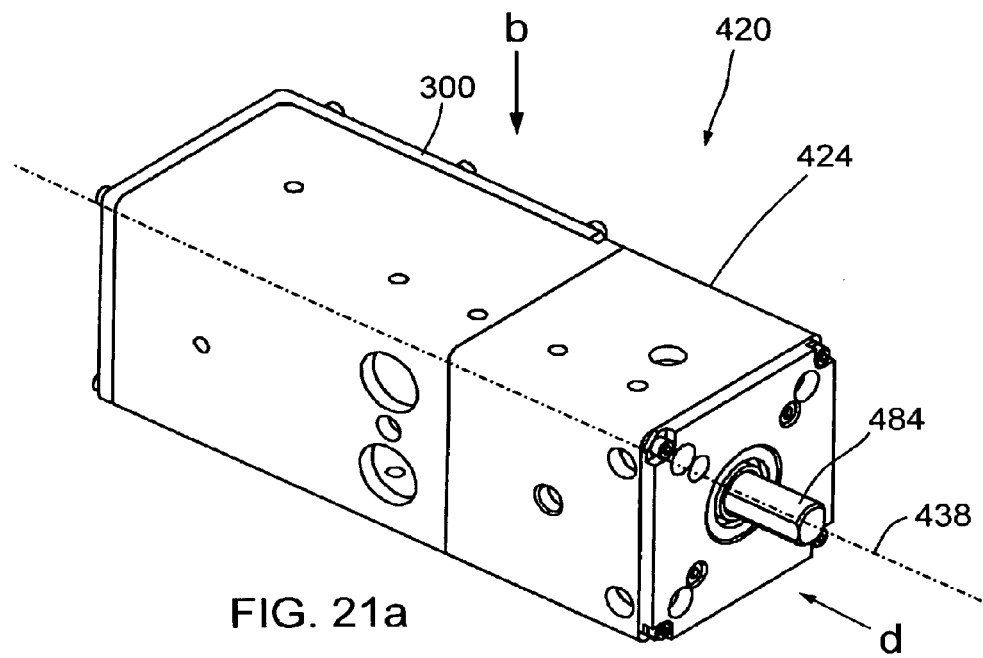
FIGS. 21a to 21e show details of the manipulator wrist forming a wrist-roll joint assembly.
Figure 21C:
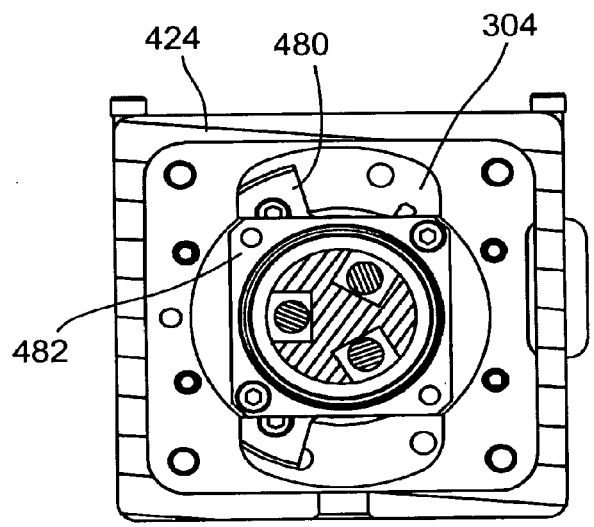
Figure 21B:
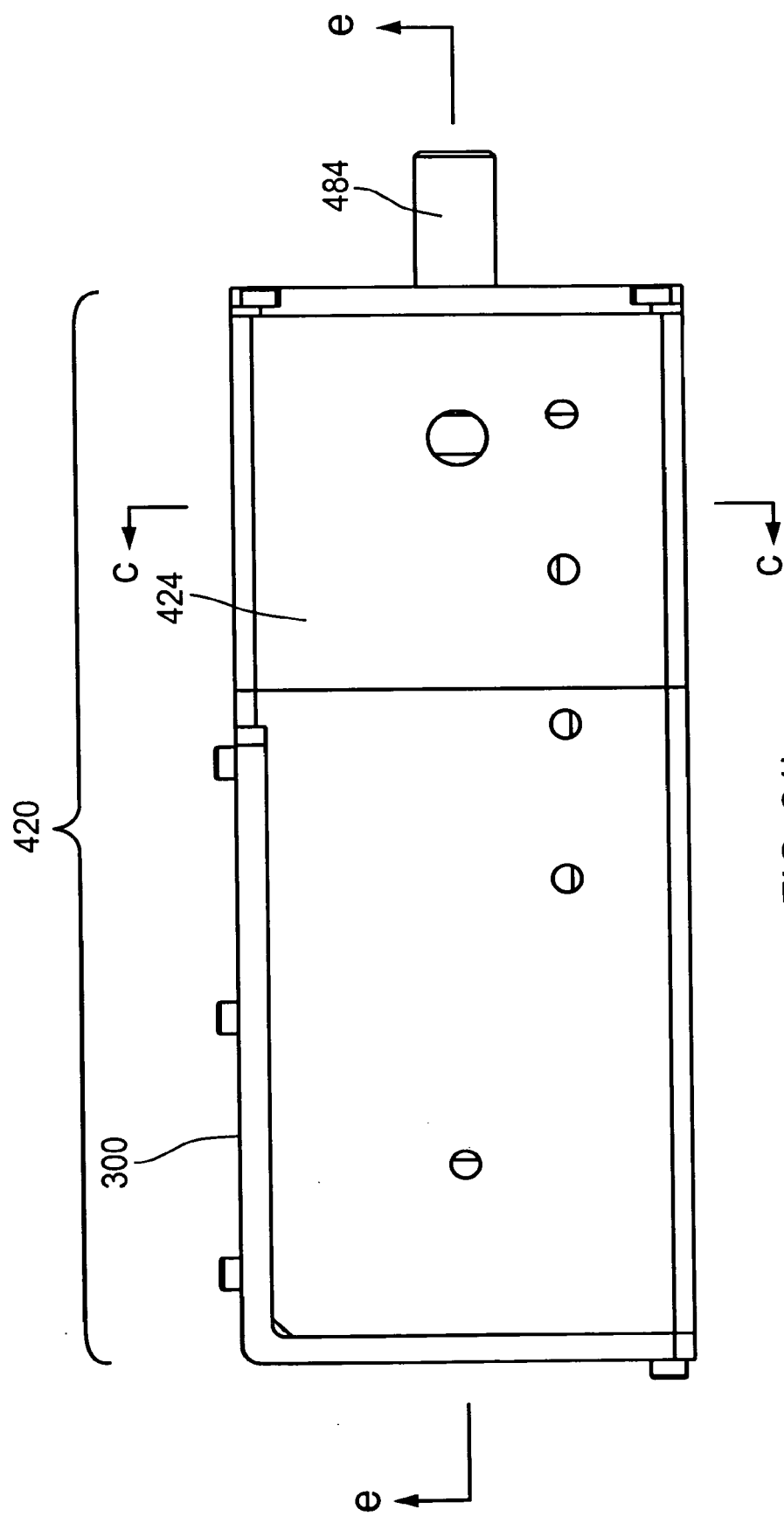
Figure 21D:
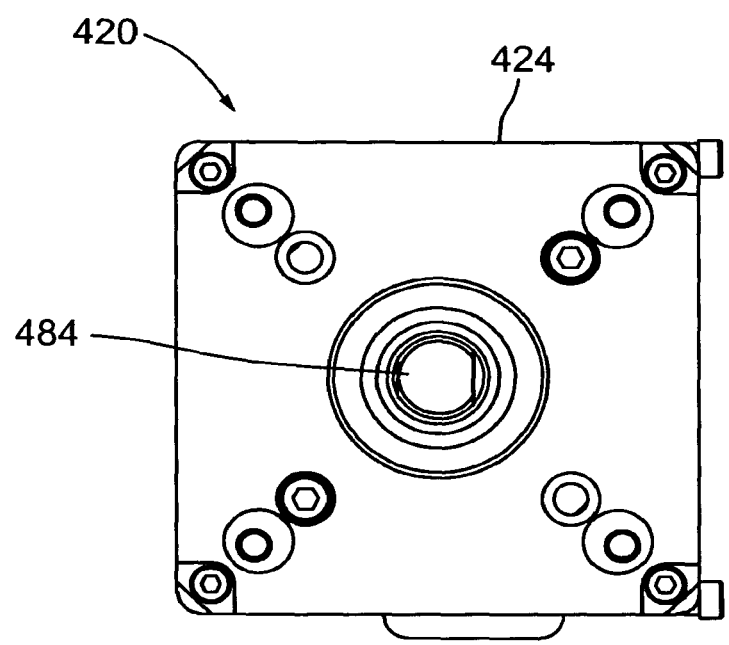
Figure 21E:
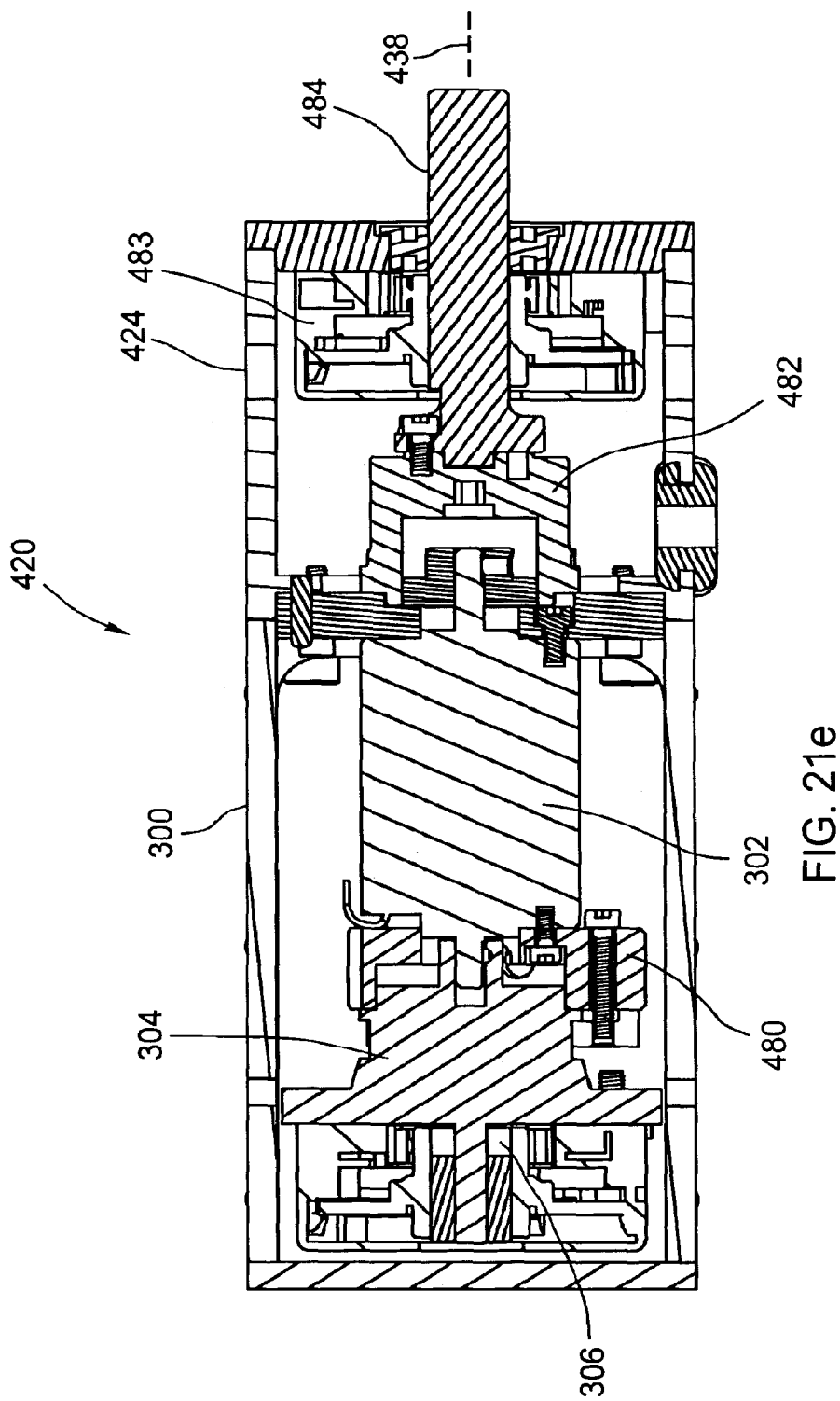

Referring now to FIGS. 21a to 21e and particularly FIG. 21e, wrist unit 420 includes a housing 300 containing an actuation mechanism which includes a motor 302, interface plate 480, brake 304, encoder 306 being configured to operate in the same way as their counterparts 470, 471, 472 and 473 in the wrist-pitch joint assembly described in the previous paragraph. The actuation mechanism within wrist 420 also includes the wrist output shaft housing 424 which encloses a harmonic-drive 482 identical to that of the wrist-pitch right-angle drive 416, an output shaft 484 at the outside end of which the end-effector 428 is connected, and an incremental encoder 483 which is identical to encoder 46 in FIG. 20c being used in the wrist-pitch right-angle drive 416. The end-effector 428 is driven by the actuation mechanism, specifically motor 302 to rotate about the wrist-roll axis 438 via the gear-reduction by the harmonic-drive 482.

Thus the six degrees-of-freedom of the manipulator are all accounted for: shoulder-roll axis 414, shoulder-pitch axis 422, elbow-pitch axis 426, wrist-pitch axis 432, wrist-roll axis 438 and tool-yaw axis 441 (which will be discussed in detail in the Surgical End-Effector Section hereinafter). The linkages of the manipulator 400 are arranged in an offset configuration in which the lower arm 408 and the fore arm 412 are both cascaded along the shoulder-pitch 422 and elbow-pitch 426 axis with respect to the shoulder-roll axis 414 and wrist-roll 438 axis. This configuration allows for a wider range of travel for all the pitch joints when accommodating for the minimum length of the manipulator arm (formed by 408, 412, 424 and 428) required to enclose the entire actuation unit for each joint given a certain desired linkage length from joint-to-joint.

The exact amount of offset of both the lower arm 408 and upper arm 412 is adjusted by the length of the section 506 (FIG. 18d) of the shoulder support 439 along the direction of shoulder-pitch axis 422, and the resulting offset locates the wrist 420 such that the wrist-roll axis 438 is aligned with that of shoulder-roll axis 414. The reason for this lies in the kinematic consideration which calls for an in-line kinematic chain for more intuitive control and also for simplified kinematics computation. By aligning the wrist-roll 438 and shoulder-roll 414 axes, the in-line kinematic configuration is achieved even though the physical manipulator is in an offset arrangement.

Figure 21F:
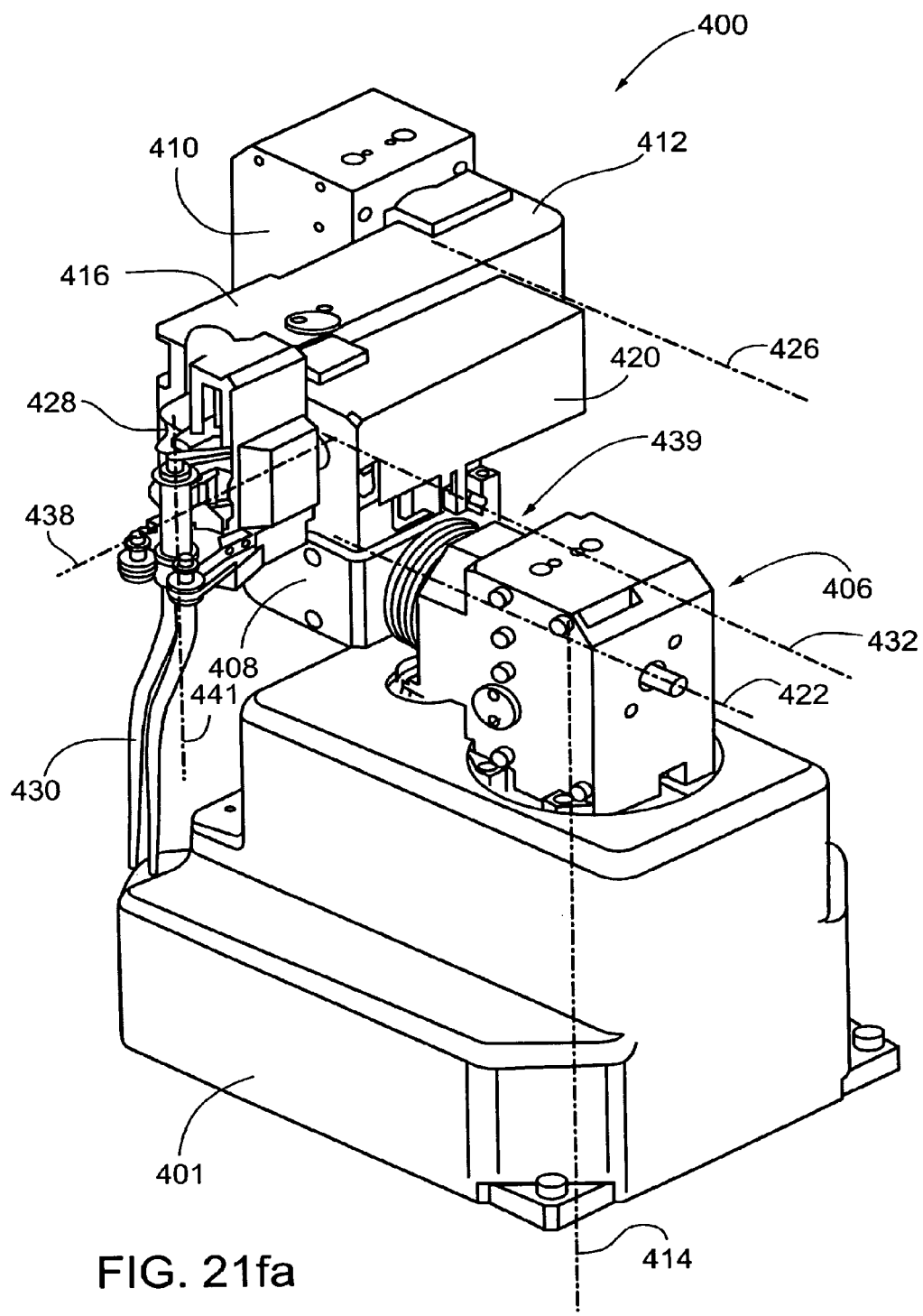
FIGS. 21f to 21i show the concept of different configurations with a seventh degree-of-freedom and the modularity of joint units making up the manipulator arm.
Figure 21F:
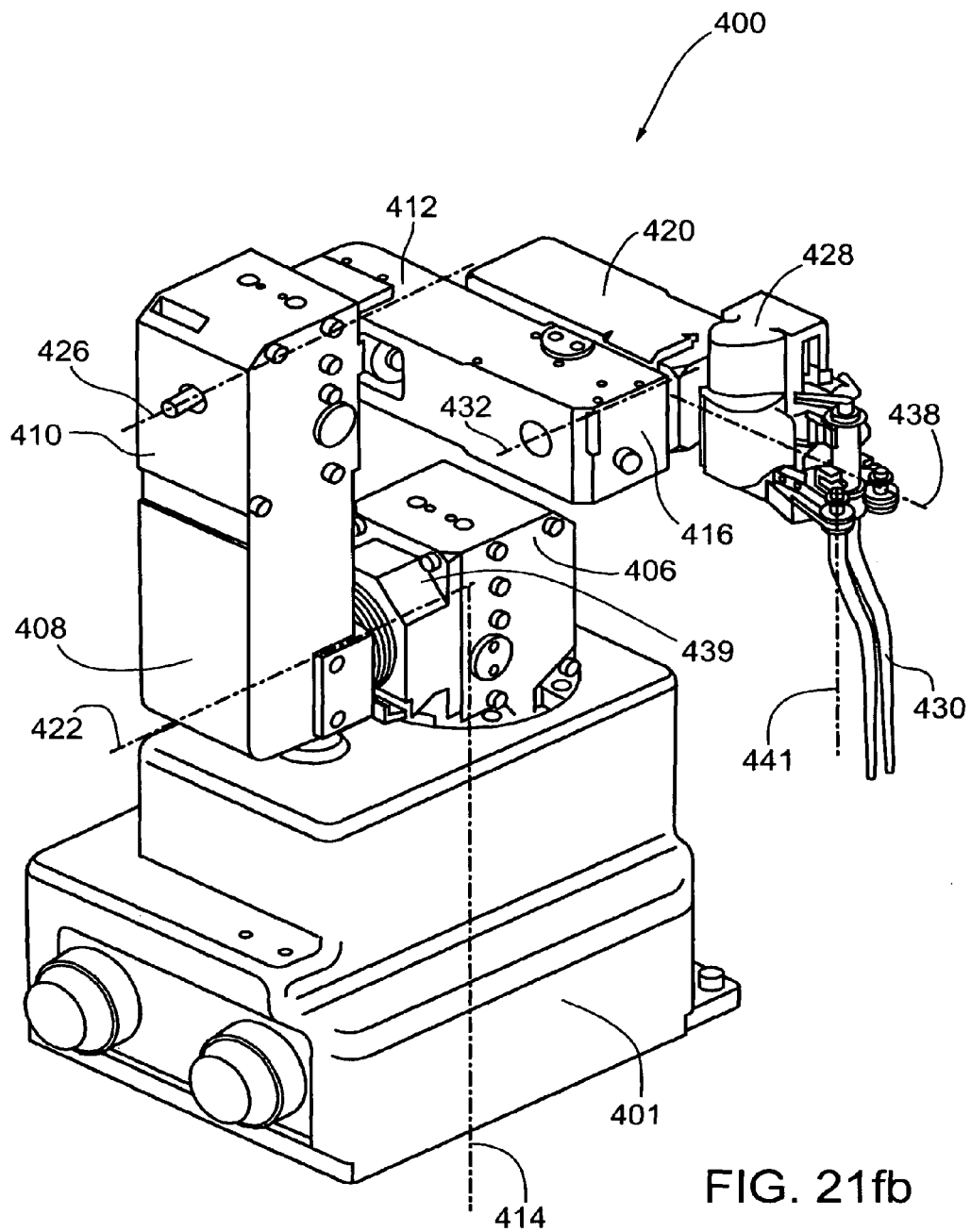
Figure 21G:
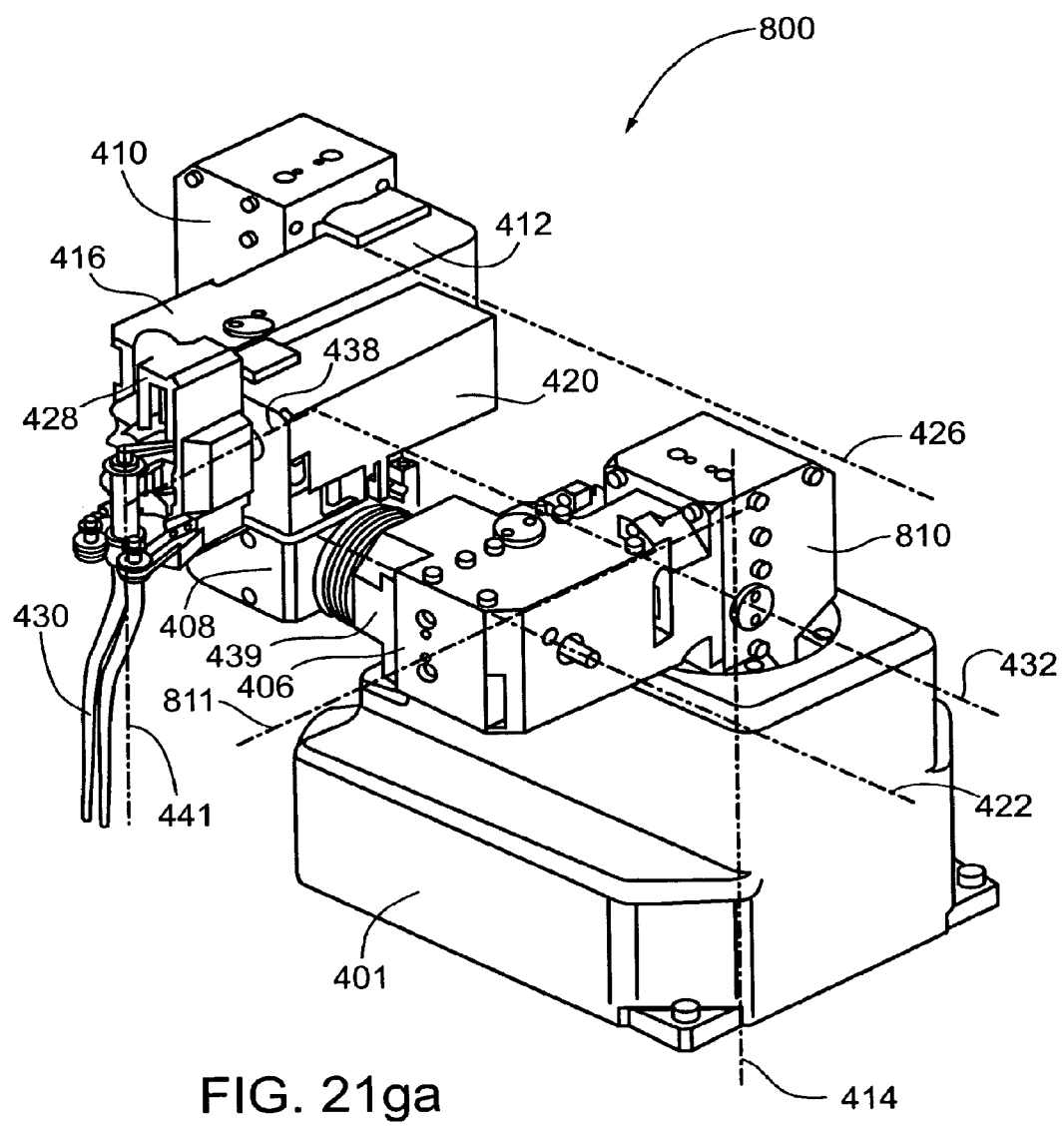

FIGS. 21fa and 21fb show a block diagram presentation of manipulator 400 of FIG. 16a, with all the original labeling in two different viewing angles, with the exception of the end-effector 428 which is shown in FIGS. 21fa and 21fb to have a cover that is not shown in FIG. 16a. FIGS. 21ga and 21gb illustrate another embodiment of a surgical manipulator 800 which uses the same components as manipulator 400 in FIGS. 21fa and 21fb but includes a seventh joint 810 which can be added in between the shoulder-roll joint and the shoulder-pitch joint. The new joint 810, which includes a right-angle drive mechanism, has a shoulder-yaw joint axis 811 significantly perpendicular to both the said shoulder-roll axis 414 and the shoulder-pitch axis 422 as shown in FIGS. 21ga and 21gb. The output pulley of this new right-angle drive mechanism 810 is oriented in the plane perpendicular to the output pulley plane of the shoulder-pitch right-angle drive mechanism 406 and is coupled to the right-angle drive 406 responsible for the shoulder-pitch. This additional joint 810 allows the robotic arm to orient the direction of the elbow retraction formed by the junction between the lower arm 408 and fore-arm 412 in any desired plane with respect to the base 401. Such a capability allows the manipulator 800 to access patients in a particularly constrained or low volume situation and allows the overall configuration of the manipulator to be adjusted to the task at hand—operating in a primarily vertical plane for minimally invasive neurosurgery, operating in a horizontal plane for stereotaxy or in combination with other equipment and sensors.

Figure 21H:
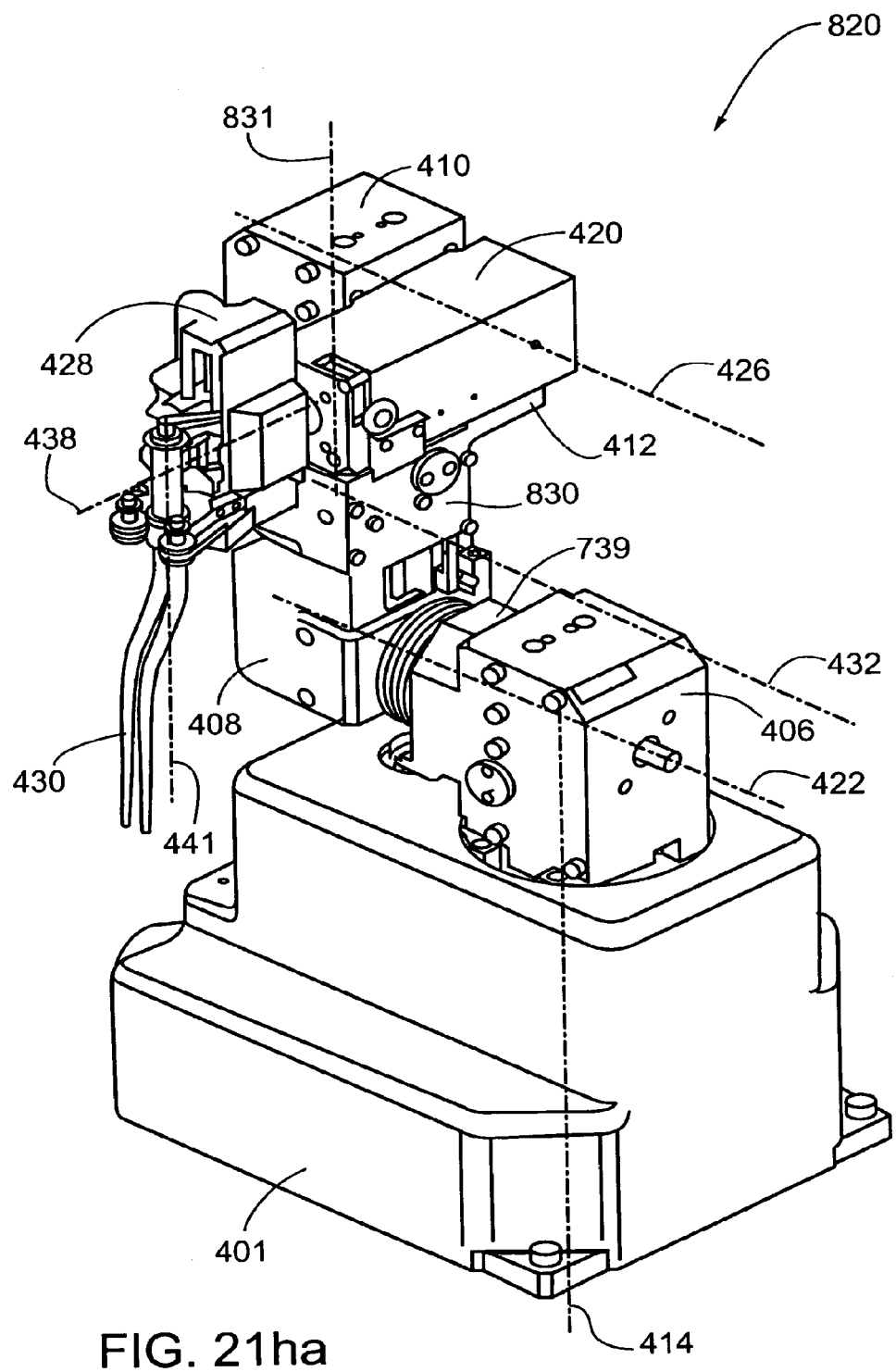
Figure 21H:
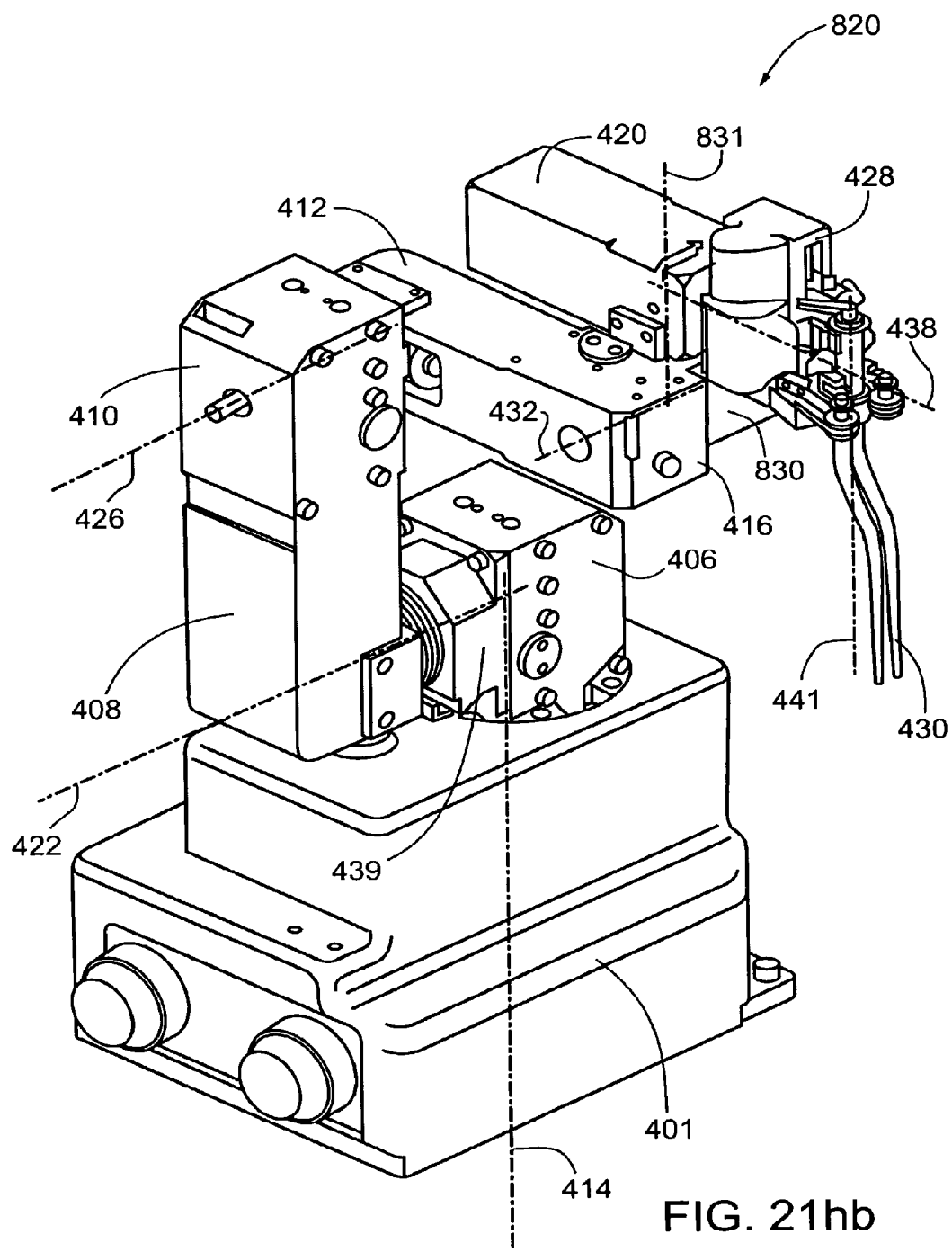

FIGS. 21ha and 21hb show two different views of another embodiment of a surgical manipulator 820 wherein a seventh joint 830 can be added in between the wrist-pitch joint and the wrist-roll joint. The new joint 830, which includes a right-angle drive mechanism as described above, has a joint axis wrist-yaw 831 significantly perpendicular to both the wrist-roll axis 438 and the wrist-pitch axis 432 as shown in FIG. 21ha. The output pulley of this new right-angle drive mechanism 830 is oriented in the plane perpendicular to the output pulley plane of the wrist-pitch right-angle drive mechanism 416 and is coupled to the supporting structure of the said wrist body 420. This additional joint 830 allows the manipulator wrist 420 to have an additional degree-of-freedom in the yaw direction when an application requires minimal or no movement of the rest of the manipulator other than the wrist 420, for instance minimally invasive surgery, or situations where lateral movement of the surgical instrument is desired without rotation.

It will be understood by those skilled in the art that the surgical manipulator 800 may be further configured such that the sequence of joints may be different, including more or less joints than shown in FIG. 21f. For some tasks, fewer than six (6) joints may be desirable for volume or access reasons, or the order of the joints within the shoulder, elbow and wrist may be reversed for better reach and access in a particular environment.

Figure 21I:
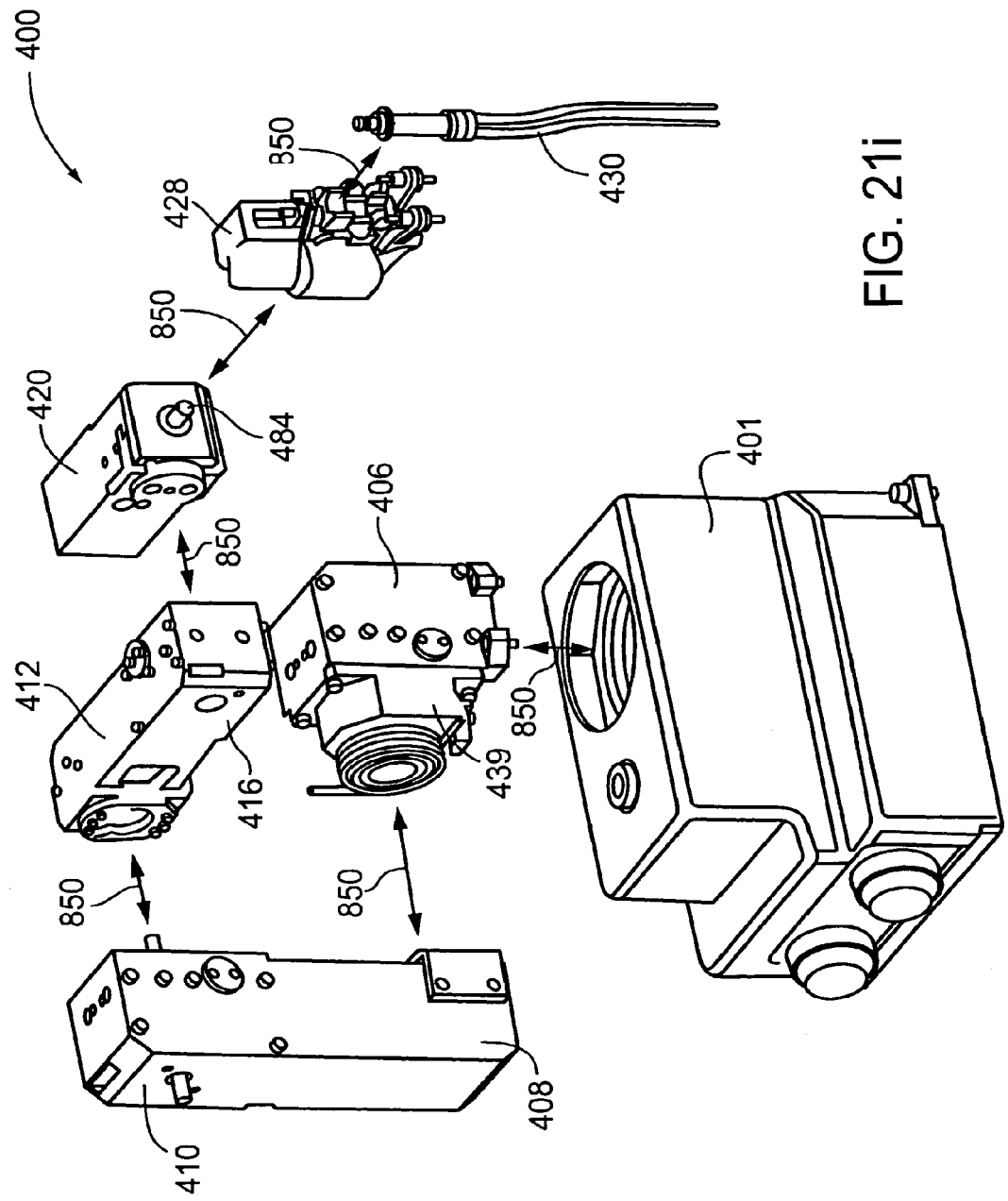

Referring to FIG. 21i, surgical manipulator 400 may be configured to be rapidly reconfigurable modular wherein modules of the manipulator can be quickly removed and replaced with a different but similar modules containing a different size, shape, orientation or sequence of joints and end effectors. This permits the manipulator 400 to be reconfigured for the task at hand while at the same time utilizing a common base 401 and controller (not shown). The quick disconnect allows for a mechanical, electrical, video interface between the remaining segment of the manipulator and the segment that is replaced. The various modules including the robotic arm components (upper arm, fore-arm and wrist), all the right angle drives and end effectors may be configured to include mating interfaces 850 comprising quick release mechanical/electrical couplings allowing them to be quickly assembled and disassembled using a minimal number of mechanical hardware parts (bolts, nuts etc.). The electrical wiring is similarly configured so that when two components are assembled the electrical plugs/sockets match to complete the different circuits.

Such interfaces 850 will exist between the base 401 and shoulder cluster 406, between the shoulder cluster 406 and lower arm cluster 408, between the lower arm cluster 408 and fore arm cluster 412, between the fore arm cluster 412 and wrist cluster 420, and between the wrist cluster 420 and end effector 428. Each of these interfaces 850 may or may not be different from each other among the different joints, but will be identical among the replacements at the same joint. To assembly or disassembly any of these joints, minimal mechanical hardware parts are required, and all electrical connections will be connected or disconnected automatically upon coupling or decoupling of the interface 850. Software settings will be adjusted at the controller upon reconnection of all clusters forming the manipulator 400 to update the appropriate control parameters reflecting the current configuration of the manipulator 400, which can be carried out manually or automatically by detecting all components recognized by the controller.

Figure 21J:
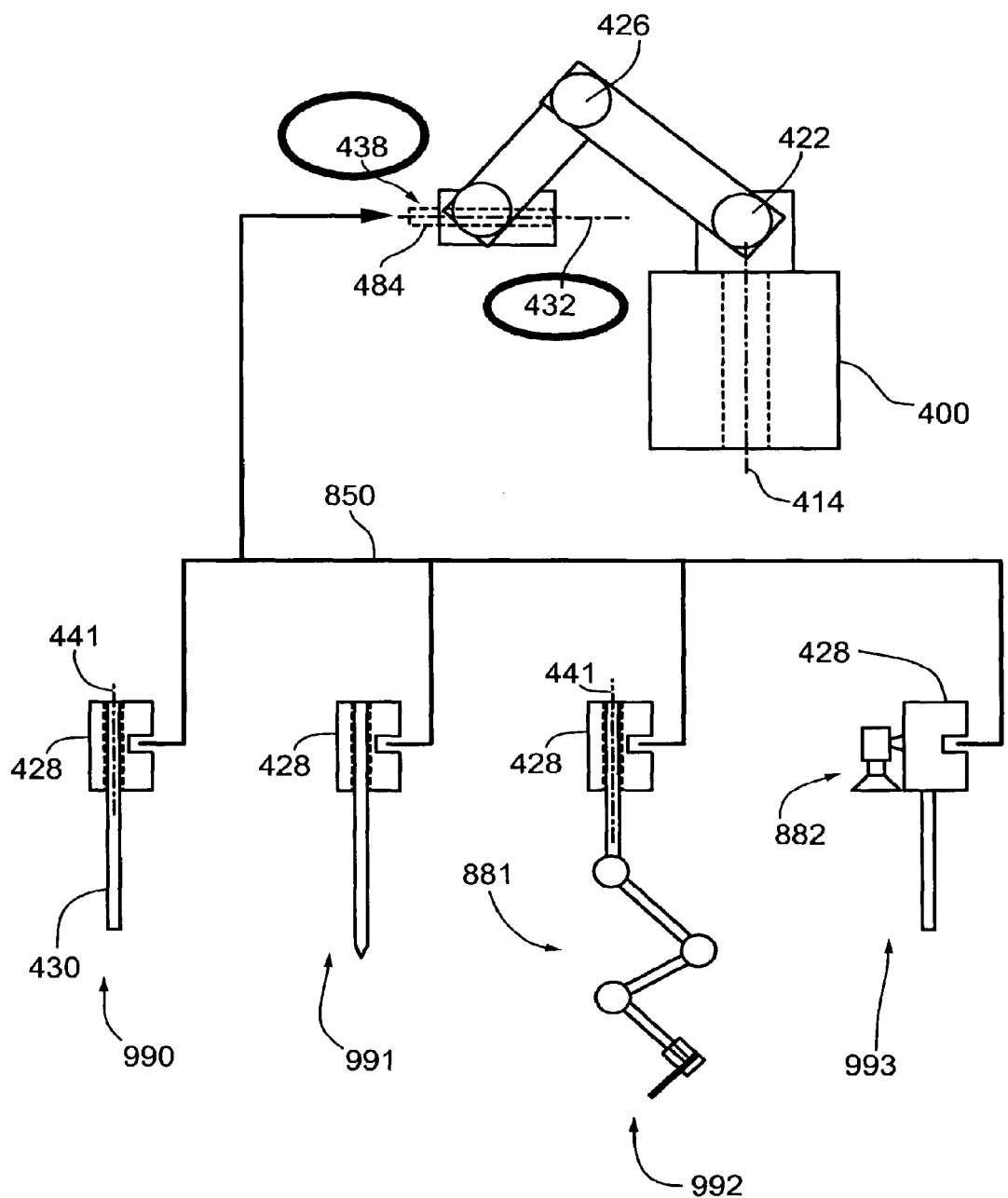
FIG. 21j shows the concept of modular end-effector with various functions attaching to the same manipulator arm.

Referring to FIG. 21*j*, the modularity of the manipulator joints, in particular that at the wrist shaft 484 between the end-effector 428 and the wrist 420, can be used to attach various purpose-specific end-effectors to adapt to different target applications. In the embodiment with the default design of the manipulator 400 shown in FIG. 16*a*, all axes 414, 422, 426, 432 and 438 are included and are the same as described earlier. Using the modular quick-disconnect interface 850 described in the previous paragraph, end-effectors 428 with different functions can be attached to the arm to carry out different tasks. In the default embodiment 990, the end-effector 428 contains the tool-yaw joint 441 as the default design configuration. However, another embodiment 991 demonstrates an end-effector 428 without the sixth degree-of-freedom but instead just a straight instrument (such as a hand-drill). Embodiment 992 illustrates that another much smaller manipulator arm 881 can be attached as the instrument of an end-effector 428, such that the manipulator arm 400 is responsible for gross motion, whereas fine motion can be carried out by the smaller manipulator arm 881, such as an endoscope. Additional sensing device 882 can be attached to the end-effector 428 as shown in embodiment 993, such as a viewing camera or tracking target, as in the case of image-guided surgery.

It will be understood that a manipulator may be constructed in which there is not tool yaw axis 441, so that the entire system has less than six degrees of freedom. For example, if the end-effector is gripping a probe, no rotational axis (rotational degree of freedom) is required by the end-effector.

3) Surgical Tools

The end effecter 428 (FIG. 16*a*) connected to the end of the robotic wrist unit 424 holds a surgical tool 430 which can be detached from the end-effector 428 in a manner to be discussed after the discussion of the tools. FIGS. 22*a* to 22*e* show a first embodiment of a surgical tool 430 which can be detachably mounted to end effecter 428 attached to the manipulator 400 (FIG. 16*a*). Referring to FIGS. 22*c* and 22*d*, tool 430 includes a main housing 500, a Teflon bushing 502 seated in the end of housing 500, a piston 504 sliding in housing 500 through Teflon bushing 502, a right hand forcep blade 506, a left hand forcep blade 508, and a forcep insert 510. The two forcep blades have a hole through them and a dowel 512 is inserted through the holes and the two blades pivot about this dowel 512 as the piston 504 moves in and out of main housing 500. Piston 504 includes a head portion 514 located at the outer end of the piston and a narrower neck 516 located between the head portion 514 and the rest of the body of the piston 504. Piston 504 includes a smaller diameter extension 522 which slides up and down between the end sections of the two forcep blades 506 and 508 which are located inside main housing 500 above the dowel 512. An O-ring 520 is seated at the end of the larger diameter section of the piston 504. Tool 430 includes a timing pulley 528.

Figures 23A, 23B:
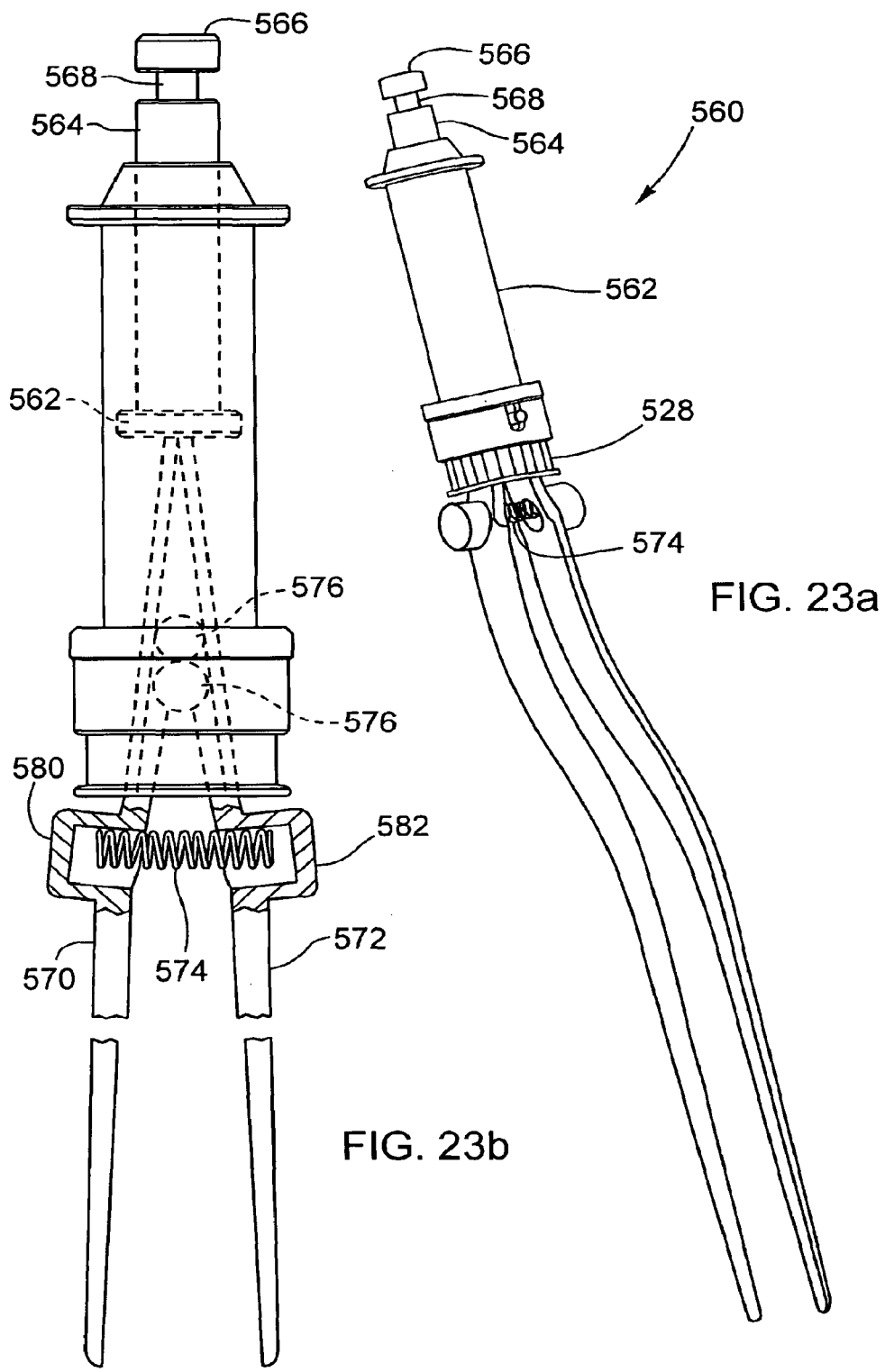

FIGS. 23*a* and 23*b* show another embodiment of a surgical tool shown generally at 560 which includes a main body 562, a piston 564 having a piston head 566 separated from the body of the piston by a neck 568. The two forcep blades 570 and 572 pivot about a common pivot point located inside housing 562 and use a spring 574 to return the blades 570 and 572 to its open position. The spring 574 is contained in housing sections 580 and 582 associated with blades 570 and 572 respectively. The tool uses an internal wedge action to close the blades 570 and 572. The driving piston 564 uses a roller 576 (FIG. 23*b*) to separate the upper proximate portion of the blades above the pivot point, which in turn squeezes the distal blade tips together which engage tissue during surgery.

FIGS. 24*a* and 24*b* show another embodiment of a surgical tool which includes a main body 632, a central piston 634 having a piston head 636 separated from the body portion by neck 638. Surgical tool 632 uses a 4-bar linkage, creating a scissor motion, to actuate the forcep blades 640 and 642.

Figures 25A, 25B:
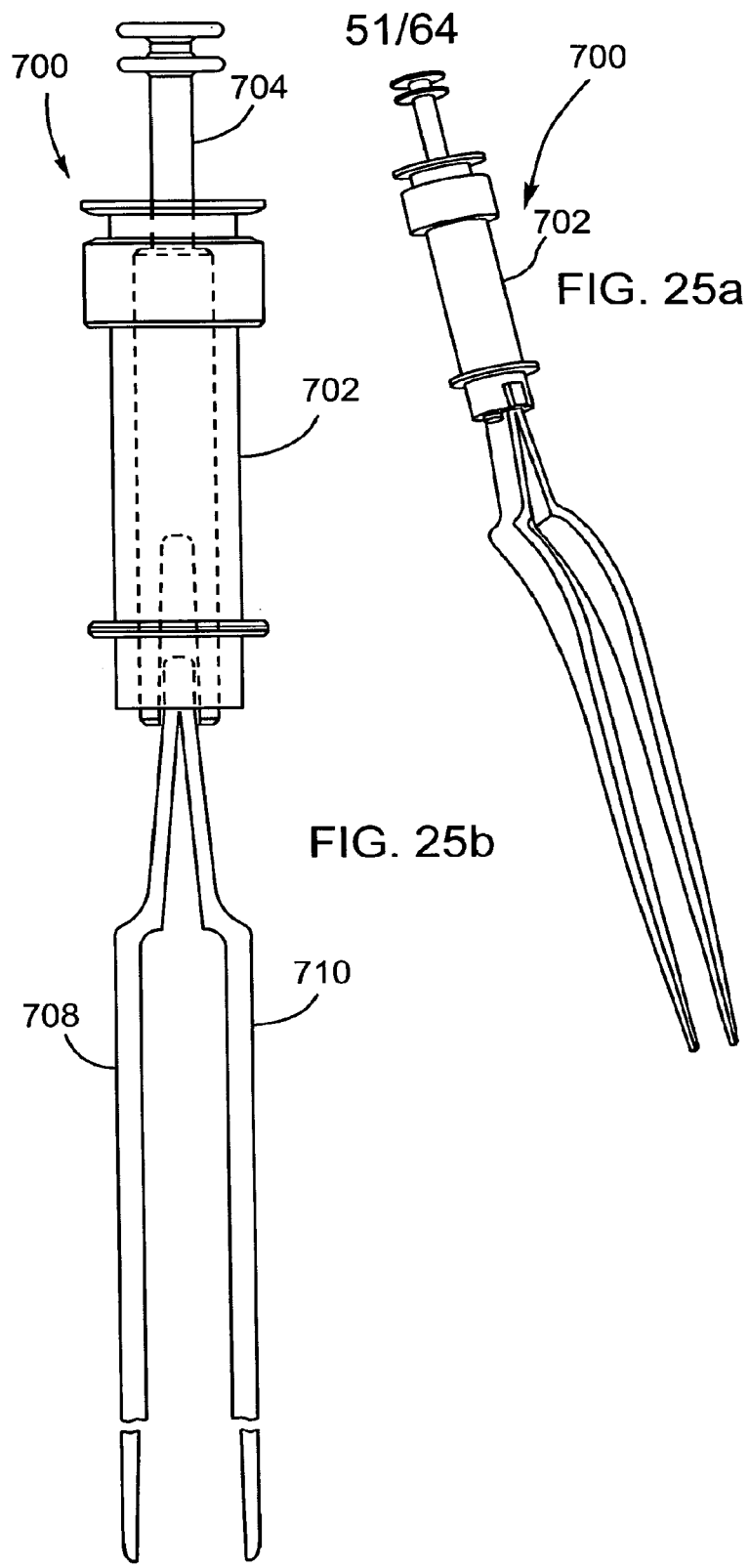

FIGS. 25*a* and 25*b* show another embodiment of a surgical tool 700 which again includes a main housing 702, a center piston 704, and forcep blades 708 and 710, made from a single piece. The forcep blades 708 and 710 are either made in a single piece or two pieces welded together so that opening of the blades is carried out by the spring force at the joint of the two blades. To close the blades the piston 704 translates downwards and with a wedge cut into it, it closes the blades 708 and 710 by elastically deforming the material where the blades 708 and 710 joint.

It will be understood that there are numerous types of surgical tools each having a tool portion which may be of different structure and function (eg. Scissors, scalpels, forceps, etc.) that may be mounted to the end-effector 428 and regardless of the structure or function of these different tool portions when the piston 504 is linearly retracted or linearly extended with respect to said end-effector 428 the tool portion of the surgical tool 430 may be activated. The forceps shown is only exemplary and non-limiting.

4) Surgical End-Effector

As mentioned above, with reference to FIG. 16*a*, the end effecter 428 connected to the end of the robotic wrist unit 424 with the exchangeable surgical tool 430 held. Microsurgical manipulators preferably require end-effectors that are small and lightweight, use different tools, have 2 degree-of-freedom (DOF) actuation, enable fast and automated tool exchange, have 6 DOF tool tip force sensing, have tool clasp force sensing, maintain a sterile barrier between the robot and the tool and/or patient, and easy to assemble.

The end-effector 428 is comprised of both sterile and non-sterile components. Sterile components are exposed to the working atmosphere of the surgical worksite and are not guarded by a bacteria resistant bag in which the non-sterile components of the end-effector 428, and subsequent remaining arm, are protected. Therefore, sterile components are required to be contamination free by the auto-claving process, using high pressure and temperature steam, after each surgery. In order to separate components on the end-effector 428 that are in direct contact with the surgical environment (and surgical tool 430) a sterile barrier needs to be established.

Figure 26A:
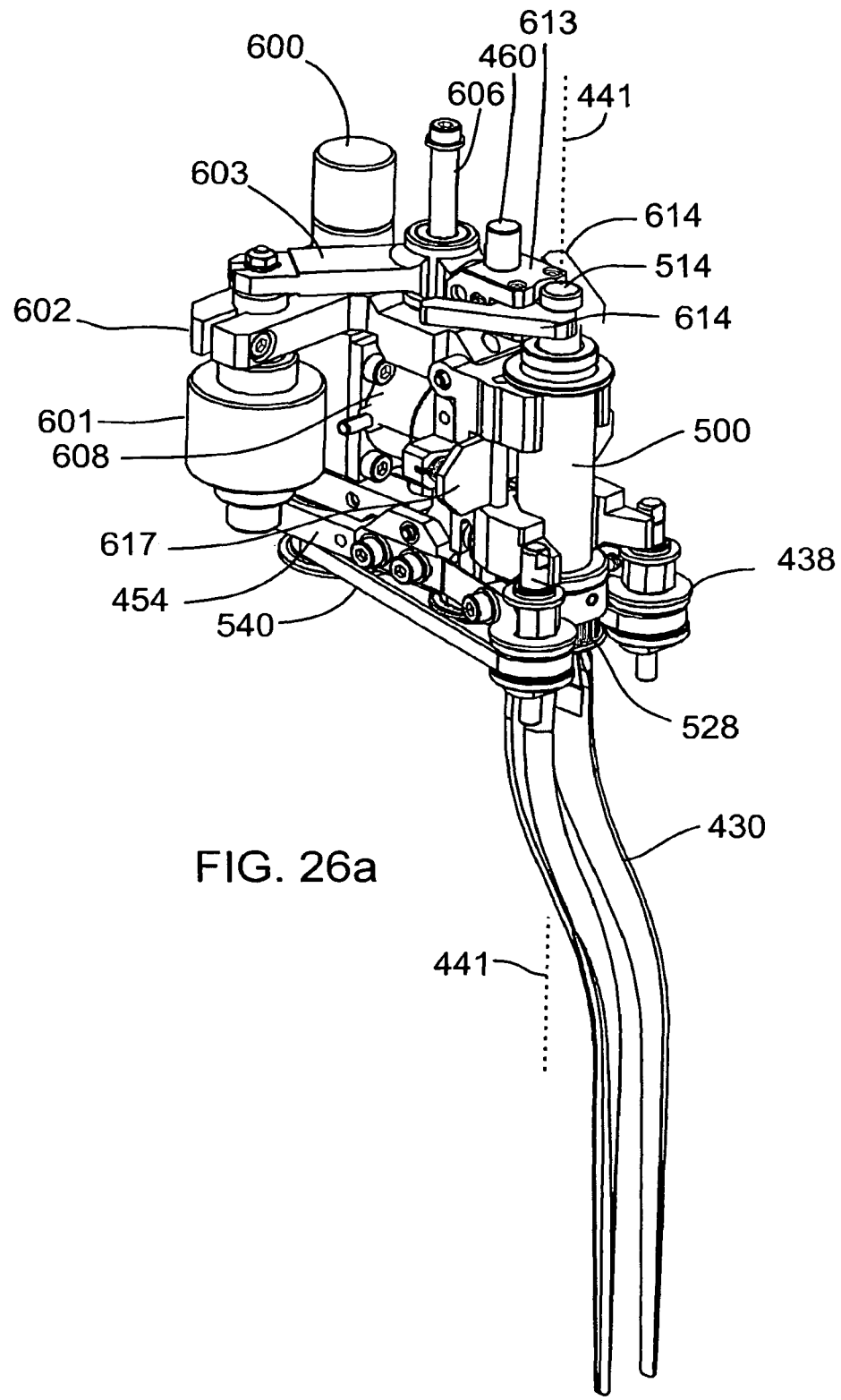
FIG. 26a is an isometric view of an assembled end-effector holding a surgical tool forming part of the present invention.

The size requirement of the end-effector 428 is preferably that it be smaller than the typical human hand and as lightweight as possible, thus driving the overall size of the entire arm. FIG. 26*a* shows an isometric view of the end-effector 428 assembled holding the surgical tool 430. Also, the end-effector 428 preferably is sized/orientated accordingly so as to provide maximum visibility at the tool tips and the work site. In order for this to be achieved, the actuator responsible for tool-actuation is preferably located away from the surgical site. This asymmetrical orientation facilitates two end-effectors being positioned closely to allow small workspaces in a dual-manipulator operating configuration to be discussed hereafter.

In a non-limiting embodiment of the surgical manipulator, an overall size of the end-effector 428 (not including the surgical tool) has a length, width and height of: 70 mm×50 mm×80 mm respectively and a weight of 240 g. These parameters satisfy the size requirements of the end-effector 428, but are exemplary only and not intended to be limiting.

Presently available surgical systems are known to have numerous sterile sub-components and offer a complex means of assembly, causing long exhaustive set-up times. The end-effector 428 disclosed herein advantageously offers minimal assembly components and a set-up time in minutes.

Figure 26B:
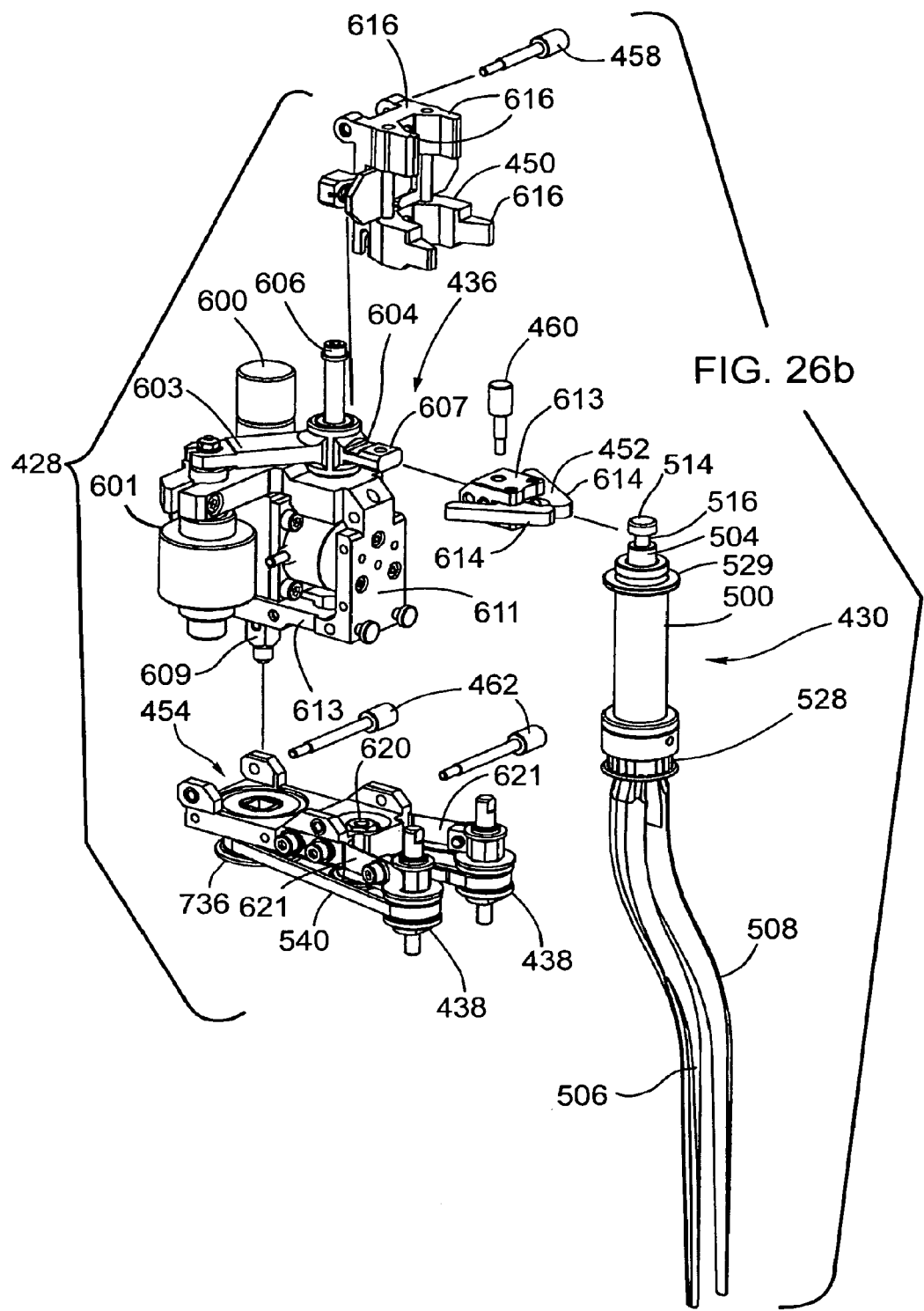
FIG. 26b is a disassembled view of the end-effector and surgical tool.
Figure 26C:
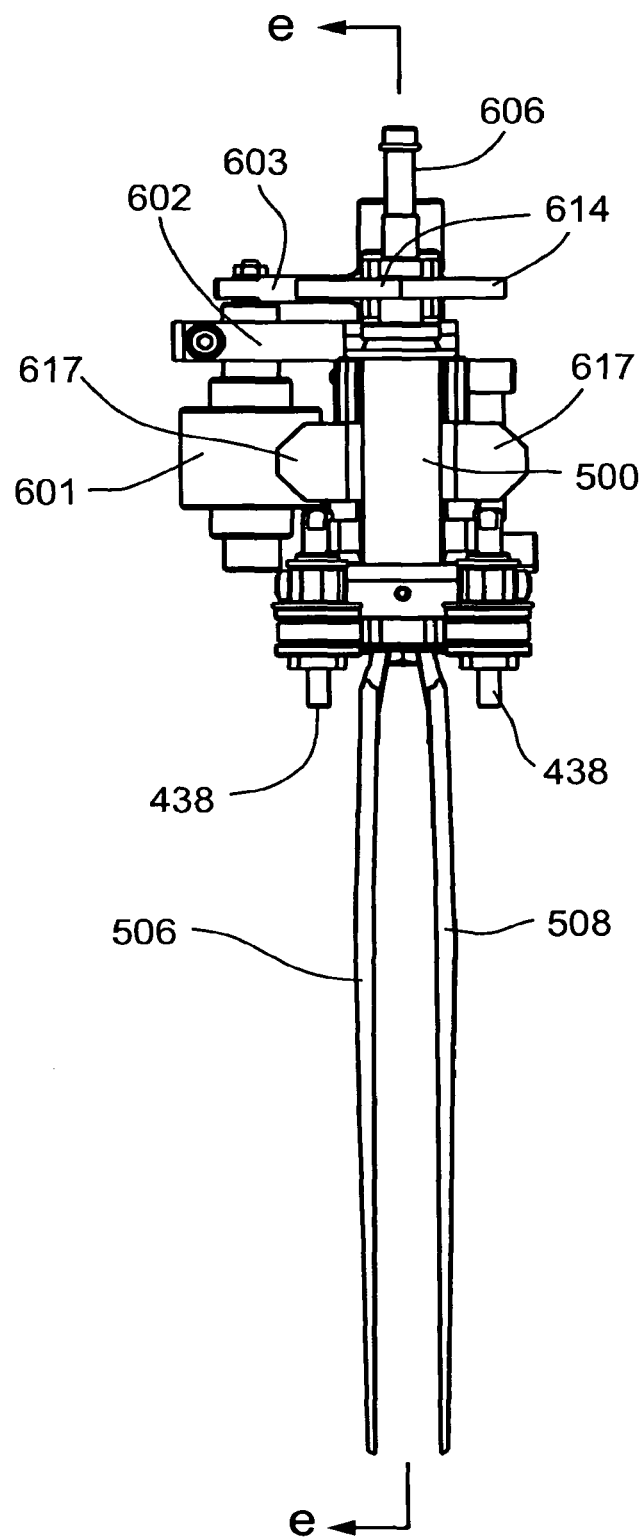

Referring to FIGS. 26*a*, 26*b*, 26*c*, 26*d*, 26*e* and particularly FIG. 26*b*, end-effector 428 includes a main assembly 436 which constitutes the non-sterile member. This is where a protective bag or hard guarding will encapsulate the end-effector 428. End-effector 428 also comprises three main sub-components, including a magnetic tool holder 450, tool actuator 452, and tool-yaw mechanism 454. All these subassemblies have a simple interface to the main assembly 436 for ease of set-up by a nurse. The exploded view in FIG. 26*b* shows how the sterile components are removed. These three sub-components, magnetic tool holder 450, tool actuator 452, and tool-yaw mechanism 454 are located and releasably secured to the main assembly 436 by threaded quick change pins 458, 460 and 462.

For a safety requirement, the surgical tool 430 must have the ability to be manually extracted from the workspace from the top during an emergency. This can be achieved by removing both the magnetic tool holder 450 and tool actuator 452 quick pins 458 and 460 respectively, sliding out the tool actuator 452 and then vertically removing the tool holder 450 containing the surgical tool 430. Another, quicker way would be to manually eject the tool 430 from the tool holder 450 (discussed later) and on a slight angle from vertical, so as to clear the tool flange, extract the tool 430 from the surgical site.

Each of the main assembly 436, and magnetic tool holder 450, tool actuator 452, and tool actuator 452 will be discussed in more detail herebelow.

a) Main Assembly 436

Figure 27A:
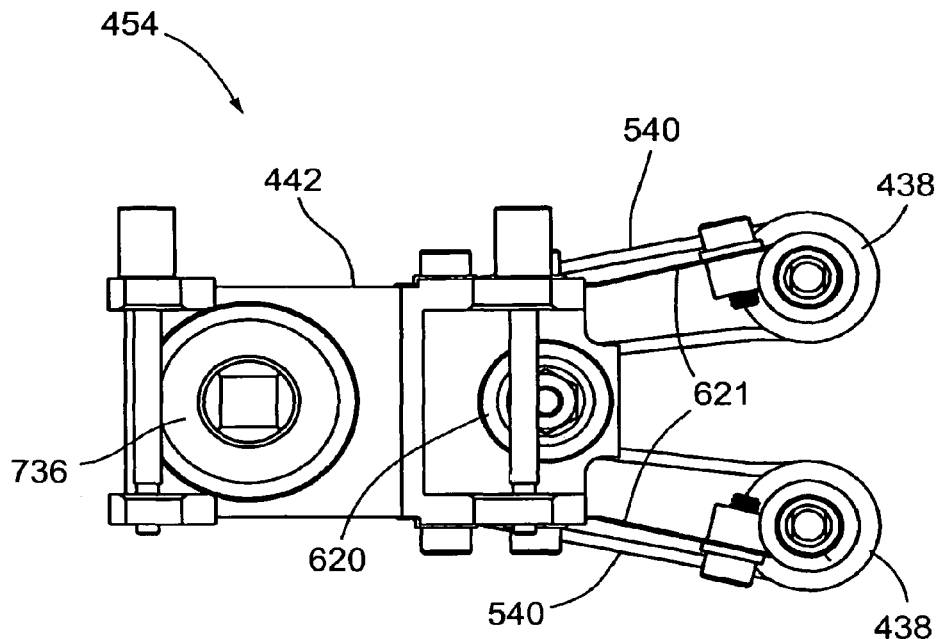
FIG. 27a is a top view of the tool-yaw subassembly.
Figure 27B:
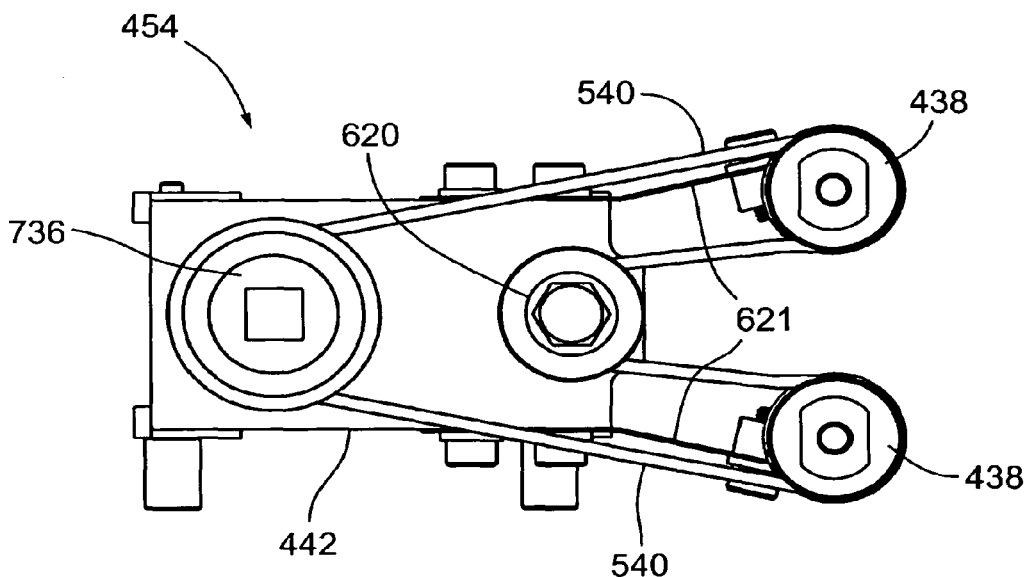
FIG. 27b is a bottom view of the tool-yaw subassembly.
Figure 27C:
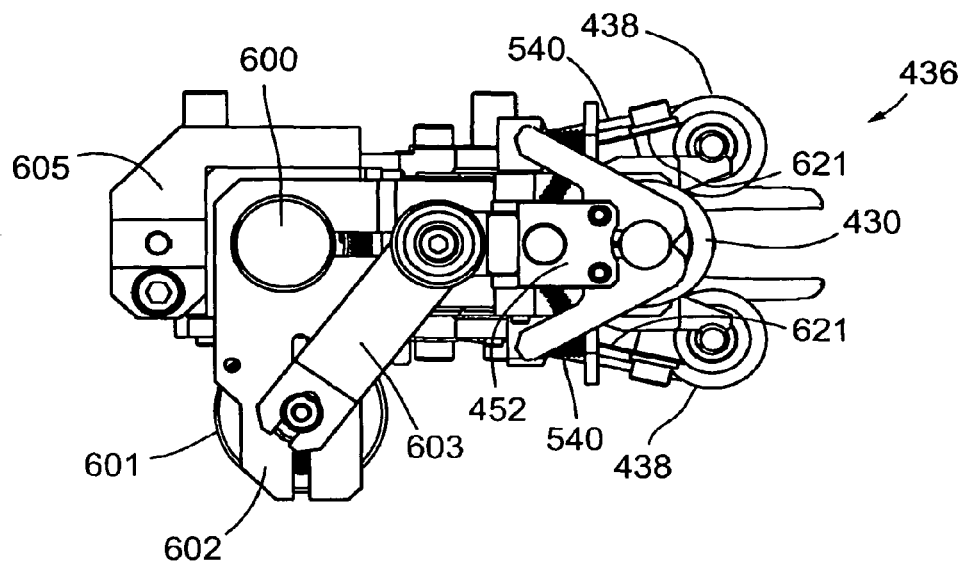
FIG. 27c is a top view of the assembled end-effector.
Figure 27D:
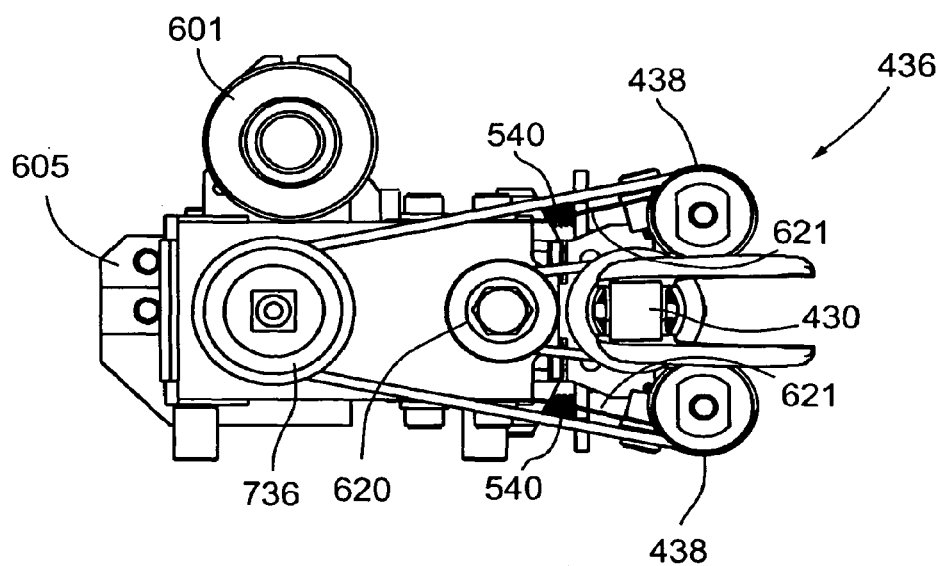
FIG. 27d is a bottom view of the assembled end-effector.
Figure 27E:
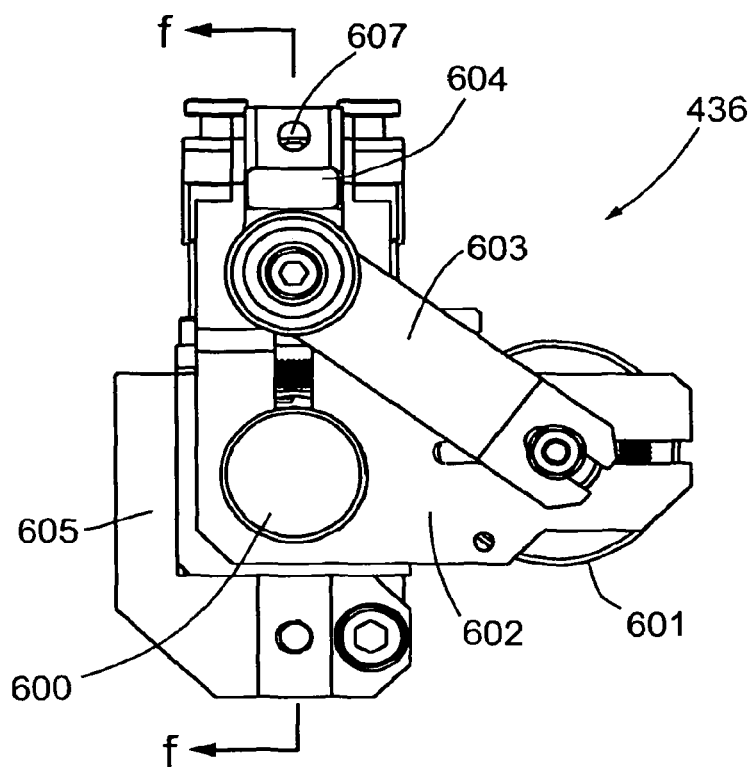
FIG. 27e is a top view of the main end-effector body.
Figure 27F:
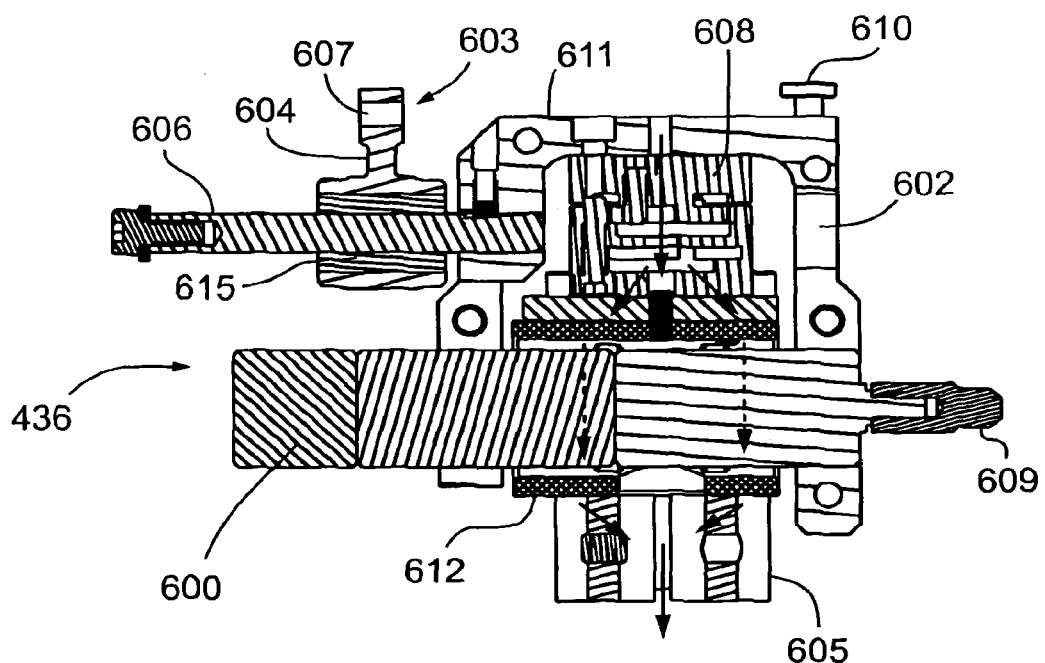
FIG. 27f is a cross-sectional view of FIG. 27e along the line f-f showing the load-path of the tip force monitored by the force-moment sensor.

Referring to FIGS. 27*e* and 27*f*, the main assembly 436 of the end-effector 428 includes all the electronic components, the tool-yaw motor 600, the tool-actuation motor 601, the tool-tip force-moment sensor 608 and the tool-actuation force sensor 604 all mounted on end-effector 428. This forms the core of the end-effector 428 where these components and their adjacent supporting structures are considered to be non-sterile and thus need to be protected by a drape bag. The drape bag will need to cover from the base of the robot all the way through the entire length of the arm until the front face 611 of the end-effector main assembly 436, whereas the remaining subassemblies of the end-effector will be attached to the main assembly via their corresponding interfaces pinching through the drape bag.

Referring in particular to FIG. 27*f*, the tool-yaw motor 600 is mounted onto the motor-support bracket 602, which is an inverted C-shape structure clamping onto both ends of the tool-yaw motor 600. A square drive shaft 609 is attached to the output shaft of the tool-yaw motor 600 which is exposed to the bottom side of the motor-support bracket 602, at which point the drive timing pulley (discussed in a later paragraph) of the tool-yaw subassembly 454 is connected to the square drive shaft 609 for rotation transmission to the tool-yaw axis 441.

Figure 26D:
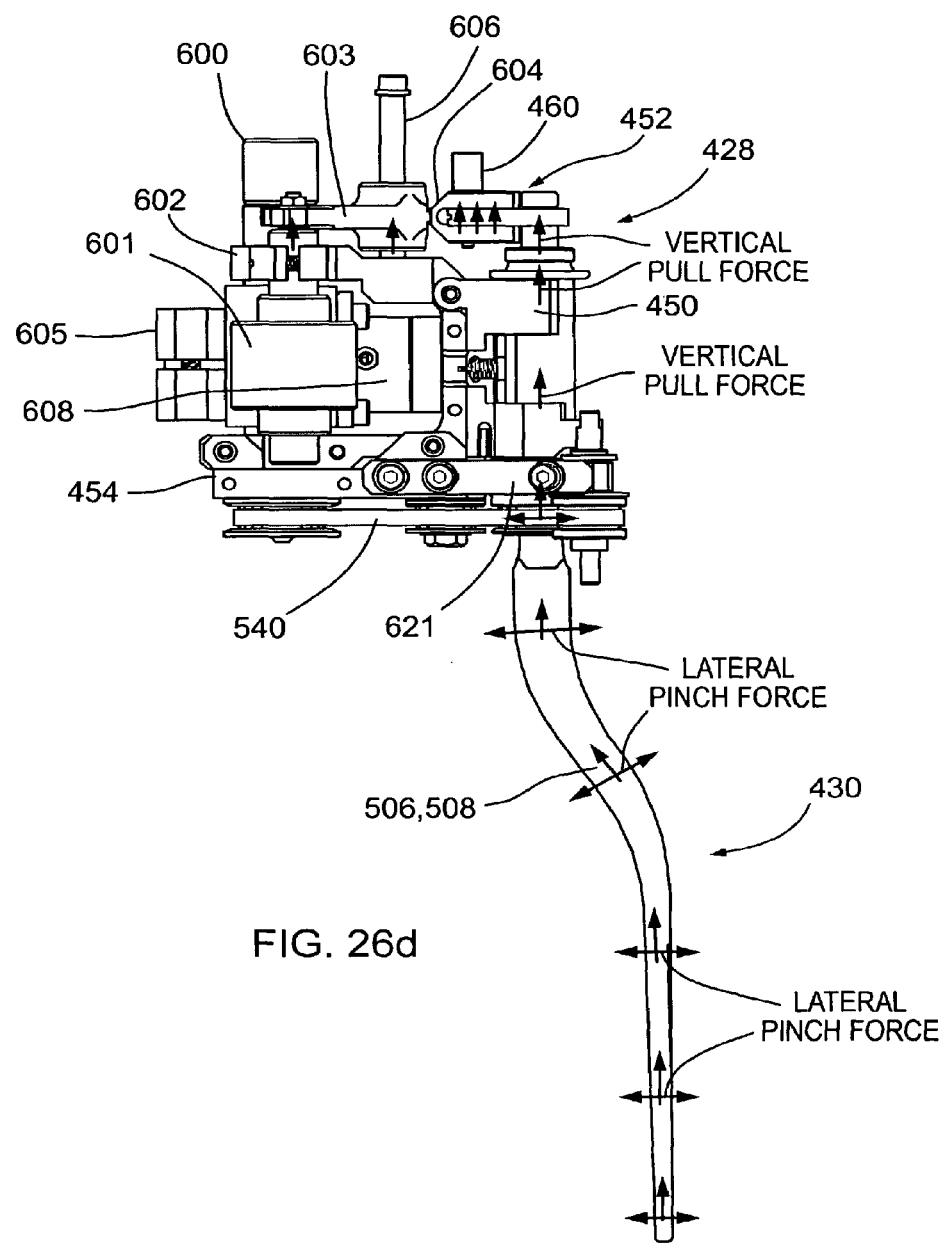
FIG. 26d is a side view of FIG. 26a showing the force-path of the pinch force as a result of tool-actuation.
Figure 26E:
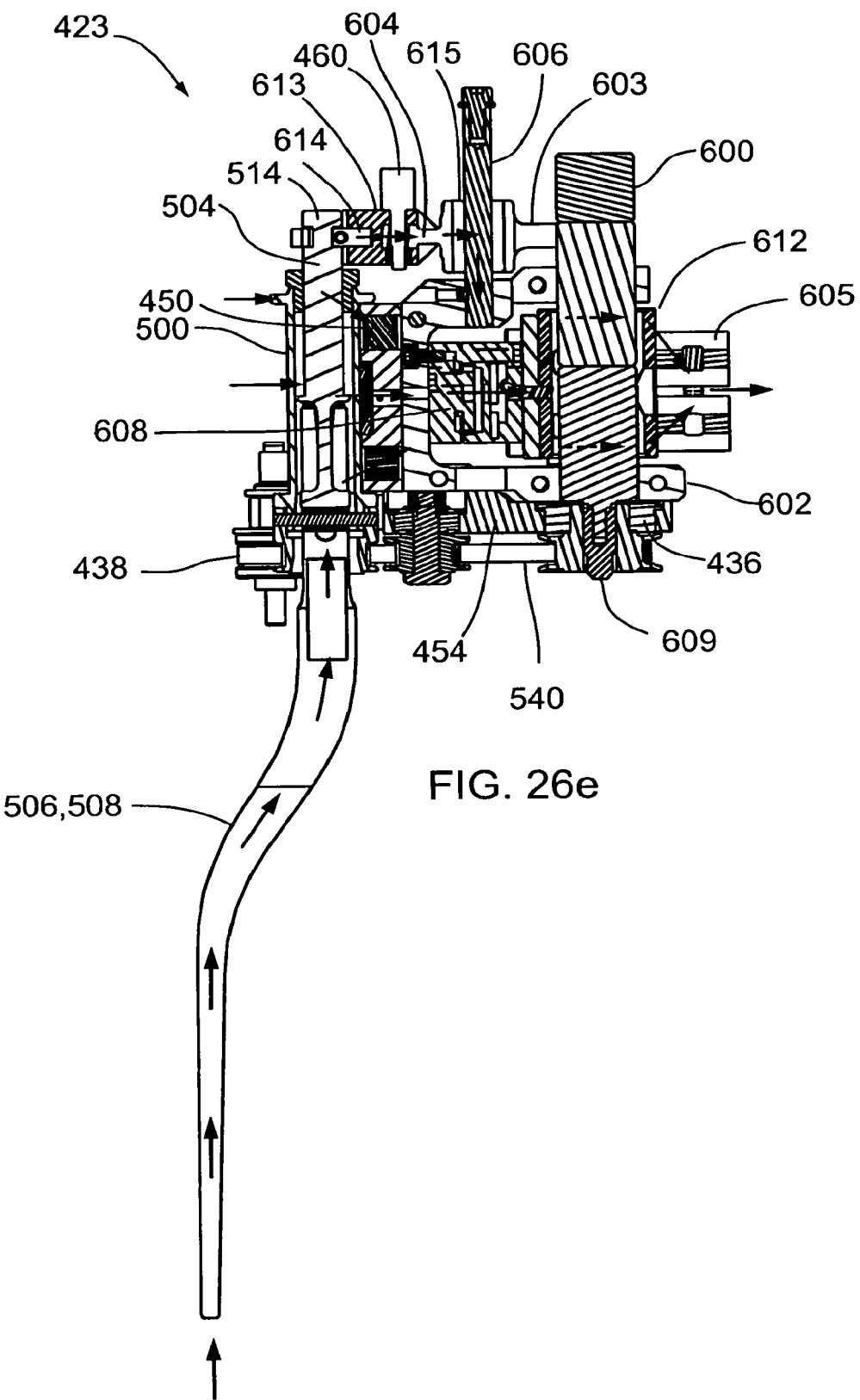
FIG. 26e is a cross-sectional view of the assembled end-effector holding a surgical tool along the line c-c of FIG. 26c showing the load-path of the tip force monitored by the force-moment sensor.

Referring to FIGS. 26*e* and 27*e*, the tool-actuation motor 601 is attached to the motor-support bracket 602 at a lateral extension, arranging the motor 601 in parallel to the tool-yaw motor 600. This motor 601 is a linear actuator, in which its output shaft moves up and down along the major axis of the motor itself, and at the end of which the angled actuator bar 603 is connected. The bar 603 can thus transmit the vertical motion to the tool actuator subassembly 452 which is mounted at the other end of the bar 603. The actuator subassembly 452, upon engaging with the tool-actuation interface (will be discussed in a later paragraph), provides the tool-actuation axis of motion for the end-effector.

Referring to FIG. 27*f*, the tool-tip force-moment sensor 608 is the single mechanical linkage between the motor-support bracket 602 and the base block 605 which interfaces back to the wrist of the robot arm. This is to ensure all of the interactive force and moment at the tool tip is transmitted through the sensor 608 only and back to the base block 605 with no alternative, load paths (will be discussed in a later paragraph). This load path is shown by the arrows in FIG. 27*a*. The base block 605 has a clearance hole 612 through which the tool-yaw motor 600 is passed through without physically contacting any part of the base block 605. The tool-holder subassembly 450, and subsequently the tool 430, is attached to the front face 611 of the motor-support bracket 602. Thus it means except for the base block 605, the remaining components of the entire end-effector are supported at a single interface at the front face of the force-moment sensor 608, see FIG. 26*b*.

Referring again to FIG. 27*f*, the tool-actuation force sensor 604 is mounted on the angled actuation bar 603 between the point where the bar 603 is supported by the vertical guide rod 606 and the interface 607 with the tool-actuator subassembly 452. The sensor 604 takes the form of a strain gauge, at which point on the bar 603 the elastic vertical deflection due to the tool-actuation can be measured (as will be discussed in a later paragraph).

b) Tool-Actuation Mechanism 452

Referring to FIG. 26*d*, the end-effector 428 includes the tool-actuation mechanism 452 that works completely independent from tool yawing mechanism 454 discussed hereinafter. This is achieved using a linear guide support 606 which is coupled to a linear actuator 601 to vertically translate the piston 504 of the surgical tool 430 via the narrow neck section 516 along the tool axis to provide a gripping motion between the two blades 506 and 508 (FIGS. 22*c* and 22*d*). This feature of the end-effector 428 can be utilized whether the tool 430 is rotating about the tool-yaw axis 441 (FIG. 16*a*) or static due to the circular neck section 516 of the tool piston 504. It can also be bypassed when using a surgical tool that doesn't require actuation (e.g. probe, scalpel, cauterizer etc.), with the only requirement being the tool does not possess any mechanical interface to couple with actuation subassembly 452 as does the piston 504 of the forcep tool 430.

Figure 28A:
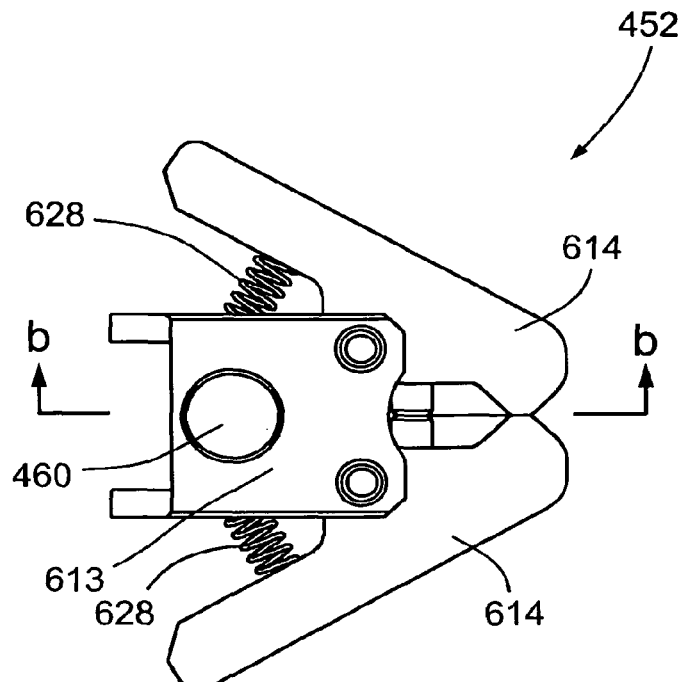
FIG. 28a is a top view of the tool actuator.
Figure 28B:
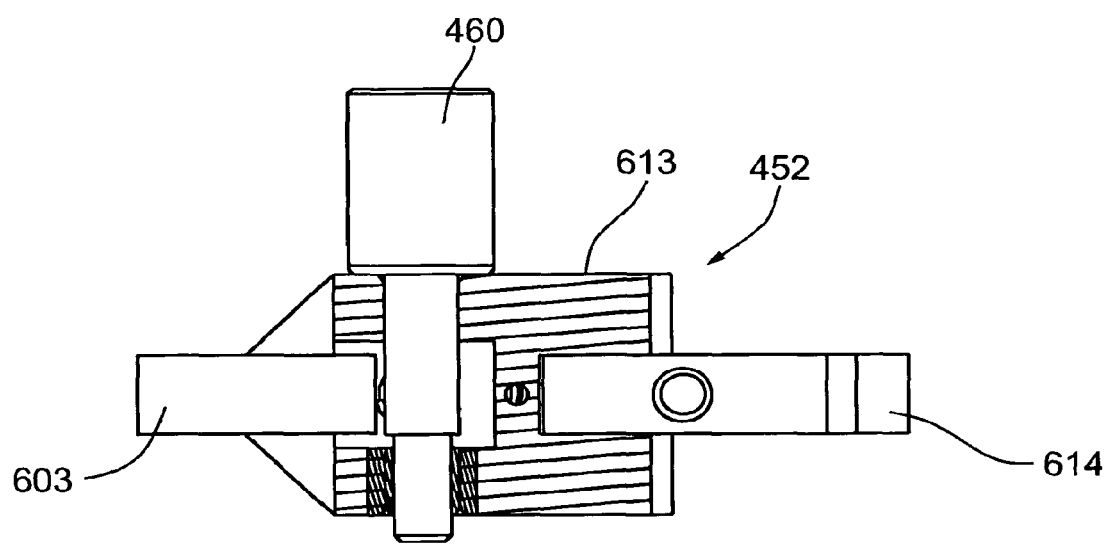

Referring to FIGS. 28a and 28b, the tool actuator mechanism 452 is coupled to an angled actuation bar 603 by a cross-location pin 460. The mechanism includes a pair of pivoting fingers 614 that are secured around the piston member 504 of the forcep surgical tool 430. These fingers 614 are spring loaded by springs 628 to an engaged position, but can be passively opened up for tool removal.

Referring to FIGS. 26e and 27f, the angled actuation bar 603 is guided by a linear ball bearing 615 to the offset actuator position. Strain gauge 604 located on the angled actuation bar 603 enables the sensing of tool-actuation forces. As the cantilever portion of the bracket exhibits deflection, in either direction caused by the reaction as a result of the up and down motion of the piston 504 of the tool 430, the strain gauge 604 will generate a voltage signal which will be fed back to the controller for interpretation. With proper calibration of the strain gauge sensor 604, the vertical force required to actuate the tool can be determined, which can then be translated into a pinching force at the tip of the blades 506 and 508 of the tool 430 (FIG. 22c) given the geometric profile of the cam section 510 of the blades 506 and 508 that are responsible for the closing of the blades 506 and 508 upon the upward sliding of the extension 522 of the piston 504 in between the blades 506 and 508. Refer to the arrows in FIG. 26d for an illustration of how the pinching force at the tips of the blades 506 and 508 is detected by the strain gauge 604.

c) Magnetic Tool Holder 450

Figure 29A:
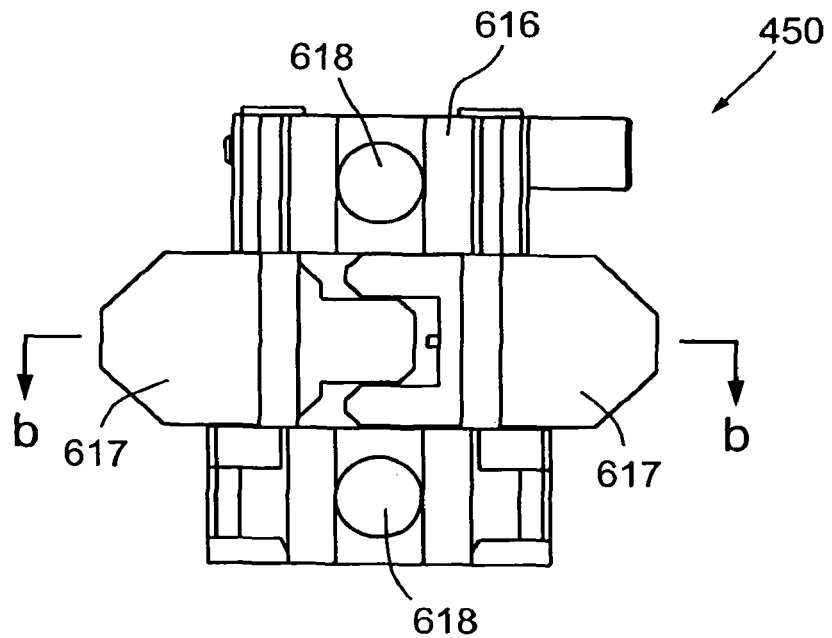
FIG. 29a is a front view of the tool holder.
Figure 29B:
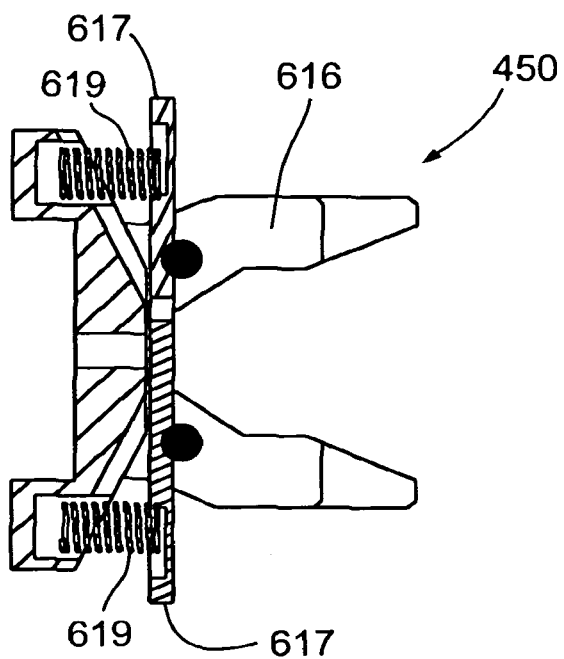
Figure 29E:
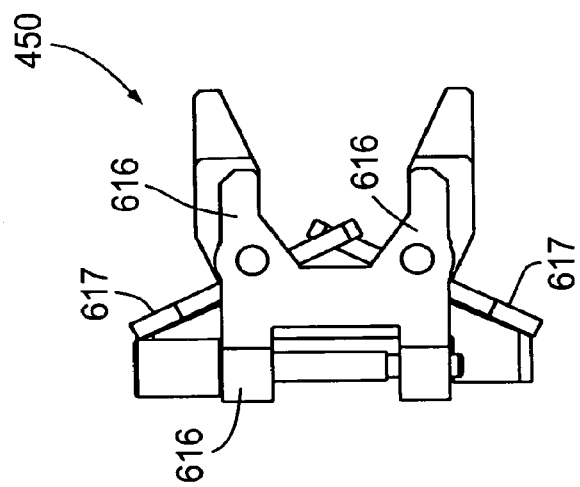
FIG. 29e is a top view of the tool holder showing the tool ejection wings in the ejected configuration.
Figure 29D:
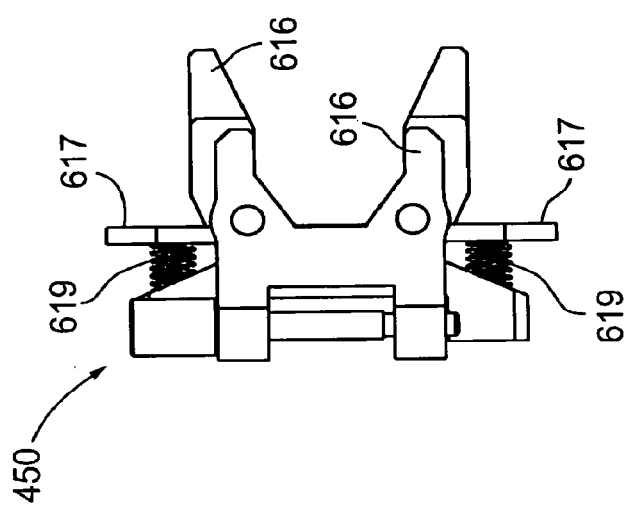
FIG. 29d is a top view of the tool holder showing the tool ejection wings in the engaged configuration.
Figure 29C:
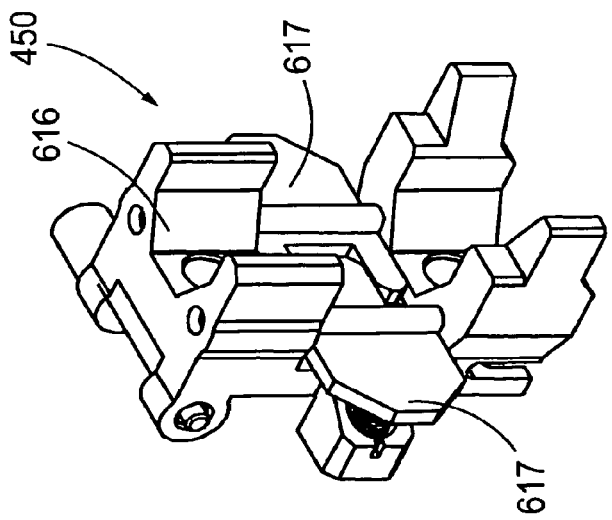
FIG. 29c is an isometric view of the tool holder.

The purpose of the magnetic tool holder 450 is to hold the tool rigidly, but still allowing the tool to rotate easily. This is accomplished by constraining the tool 430 in a support body 616, which in a non-limiting exemplary embodiment shown in FIG. 29c is a generally 'V' shaped block made from ABS plastic having an elongate channel having a size suitable receive therein the cylindrical tool body 500 of surgical tool 430, which allows the tool 430 to rotate within support body 616 with minimal friction. Referring to FIGS. 26b, 29a and 29b, the tool body 500 of the surgical tool 430, preferably made from 400 series stainless steel which is magnetic, is seated in the 'V' block 616 by two rare earth pot magnets 618 imbedded in the 'V' block. The magnetic force and 'V' block reaction forces tangential to the shaft secure the tool 430 radially, whereas flanges 529 on the body 500 of the surgical tool 430 locates and constrains the tool axially (FIG. 22a), due to a close axial fit with the 'V' block body 616. FIGS. 29c to 29e show more detailed views of the magnetic tool holder.

Another capability of the tool holder 450 is that it can enable passive tool exchange for automatic tool change-out. Referring to FIGS. 29c, 29d and 29e, the 'V' block 616 is featured with a tool release mechanism that once compressed can pivot, similar to a scissor action, to strip the tool body 500 away from the magnets 618 and eject the tool 430. FIG. 29d shows the tool-engaged configuration, or when the tool-ejection wings 617 are in closed position. FIG. 29e, on the other hand, shows the tool-ejecting configuration, or when the wings 617 are in opened position. After ejecting the tool, the wings 617 will return to the default closed position by the compression springs 619 located at the back of each wing 617 (best seen in FIGS. 29b and 29d).

Figure 29F:
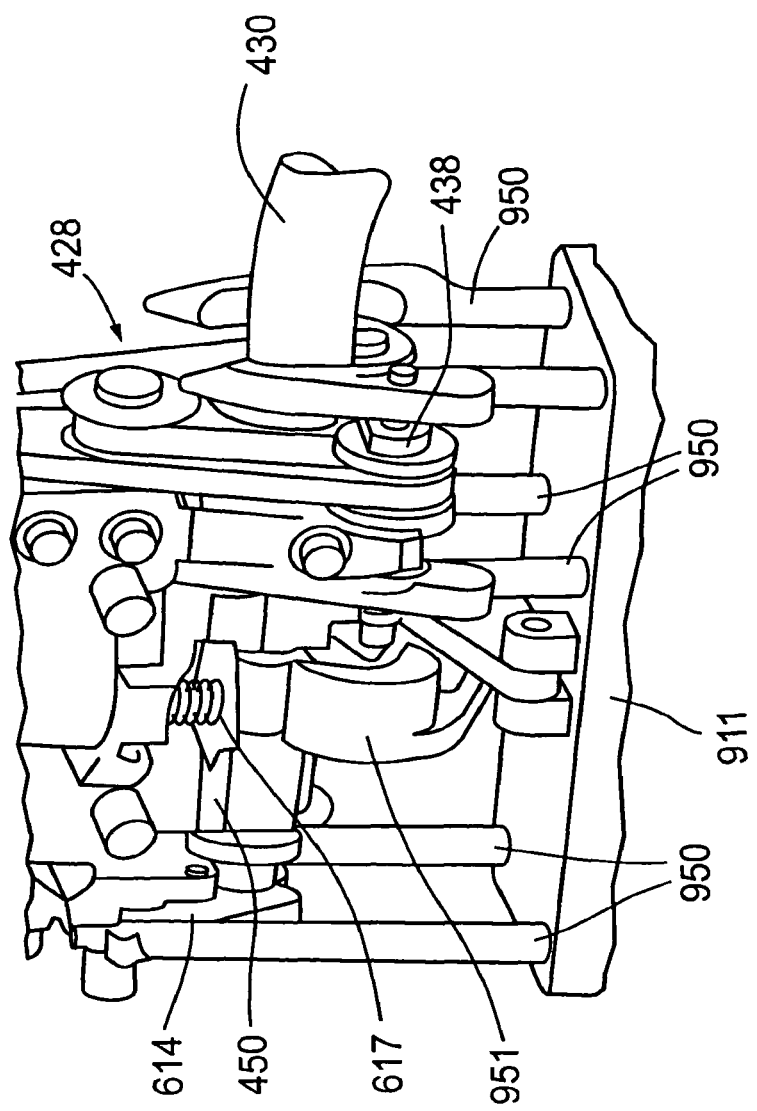
FIG. 29f is an isometric view of the end-effector releasing the tool at the tool tray.

FIG. 29f shows the passive tool changer mechanism on a tool tray 911 for auto tool-changing. Static pins 950, fixed to a tool tray 911 are positioned to engage specific end-effector features to release the tool. These features include the pivoting fingers 614 of the actuator subassembly 452 and the outer idler pulleys 438 of the tool-yaw subassembly 454, both of which are engaging with the tool 430 and needs to be released. The actual ejecting feature, however, lies in the tool-holder 450, from which the ejecting wings 617 need to be pressed backward into the opened position so as to eject the tool 430. This is carried out by the mating ejection latches 951 on the tool tray 911, which line up with the wings 617 and has a spring-loaded pliers-like mechanism to provide a cushioned tool-ejection.

The downward motion of the manipulator 400 is the only active component of this process, in which the end-effector 428 is oriented such that the tool 430 is horizontal when the manipulator 400 pushes down onto the tool tray 911, forcing the end-effector 428 engaging features 614 and 438 to be opened up by the pins 950 on the tool tray 911, whereas the wings 617 are actuated by the ejection latches 951, thus releasing completely the tool 430 onto the tool tray 911. To pickup a tool, the process is reversed. The manipulator 400 brings the empty-handed end-effector 428 over the top of the tool 430 on the tray 911, presses down the end-effector 428 to open up the engaging features 614 and 438 as well as the ejection wings 617, and captures the tool 430 by the magnet 618 on the tool holder 450 of the end-effector 428. The tool tray 911 has multiple sets of pins 950 for each corresponding surgical tool, and also possesses a tool-identification sensor, which upon reading the tag built-in to each tool, the main controller can register which tool the manipulator 400 has picked up. Identification tags on the tool can be a bar code or infra-red tag, which works with a corresponding IR-sensor on the tool tray 911.

d) Tool-Yaw Mechanism 454

The end-effector 428 includes a tool-yaw DOF that is actuated by a servo motor integrated with an anti-backlash spur gearhead and an incremental encoder. Referring to FIG. 26b, bonded to the output shaft of the motor-gear-encoder combo 600 is the previously described square pin 609 that drives a timing pulley 736 from the tool-yaw subassembly 454. Since the tool-yaw mechanism 454 is a removable sterile component, a quick-disconnect coupling from the non-sterile servo actuator main assembly 436 is required. The square pin 609 matched precisely to a square bore on the drive pulley 736 enables torque to be transmitted to the tool yaw mechanism 454, but allows easy de-coupling for auto-claving.

Referring to FIGS. 27a and 27b, tool yaw mechanism 454 includes a frame 442, and through a pair of idler pulleys 438 mounted thereon, a disposable toothed belt 540 engages a complementarily toothed pulley 528 on the surgical tool 430, (see FIG. 26b) on two opposite ends of the pulley diameter. The toothed belt 540 routing is completed by the middle idler pulley 620 mounted on frame 442 which has the same pitch diameter as the outer idler pulleys 438. The bi-directional rotation of the belt 540, driven by the drive pulley 736, converts tangential forces to rotary motion on the surgical tool 430. One of the main attributes that the tool yaw mechanism 454 exhibits is the passive removal and replacement of different surgical tools 430. The open front-framed architecture and belt configuration allows the tool 430 to be ejected/replaced from the front of the tool yaw mechanism 454, avoiding it being tangled around the belt 540. The tool ejection process is further aided by the outer idler pulleys 438, supported by sheet metal flexures 621, which can be passively spread out enough to completely disengage the tool, eliminating any frictional effects. When engaged with the tool 430, the metal flexures 621 allow a constant preload to the timing belt 540 during tool yawing but can also manually collapse, when no tool is present, for easy timing belt replacement. FIGS. 27c and 27d show further details of components making up the end-effector.

It will be appreciated by those skilled in the art that the end-effector 428 disclosed herein may be retrofitted onto any robotic arm assembly and is not restricted to being mounted on manipulator 400 disclosed herein.

Similarly, it will be appreciated by those skilled in the art that the right-angle drive unit 10 disclosed herein may be used in any application requiring conversion of rotational motion along one axis to rotational motion along another axis and is not restricted to being mounted on manipulator 400 disclosed herein.

Haptic Feedback

In order for the surgeon to retain the sense of touch at the hand-controller during a telerobotic operation, haptics is required which means the end-effector must be capable of providing realistic external force and torque sensing at the tool tips and reflecting back to the hand-controller. To obtain accurate haptic feedback, the end-effector is advantageously designed so that forces and torques (moments) at the tool tips are directly registered by the force-moment sensor 608, which measures force and moment through elastic deflection in the direction of interest. The sensor 608 needs to measure the force and moment in all six directions, so that a full 6DOF haptic feedback can be achieved. It needs to have sensing precision within the range of soft tissue interaction, which is roughly 1 to 200 g. The size of the sensor 608 is preferably compact enough to be incorporated into the end-effector design without enlarging the overall end-effector size to an undesirable scale. Given these parameters, the smallest force-moment sensor preferred in the present manipulator is the Nano17 of ATI Industrial Automation, having an overall size of just ø17 mm×14.5 mm long.

The location of the force-moment sensor 608 within the end-effector 428 is important as it determines the eventual precision of the haptic feedback. Ideally, the sensor 608 should be right at the tool tip where the external forces and moments are exerting when the tool is in contact with a foreign object. In practice this is difficult to achieve as it will mean having a delicate electronic component build-in to the surgical tool, which needs to go through auto-claving cycles for sterilization. Also, various tools need to be fitted onto the end-effector 428, thus electronic interfacing is required upon changing of tools which add to the complexity of the end-effector design. Furthermore, sensors on each tool will significantly increase the cost of tool production and subsequently the investment on the overall system by the customers.

Therefore, it is beneficial to keep the miniature force-moment sensor within the end-effector but close to the surgical tool. This will minimize the amount of weight on the free end of the sensor so as to avoid saturating the sensing capacity of the sensor. Also by reducing the physical distance between the tool tips and the point of sensing, signal distortion throughout the load path due to mechanical imperfections, such as backlash, compliance and vibration, can be minimized. The load path is analogous to the current path in an electrical circuit. Optimum force and moment sensing can be achieved when all the forces and moments originating from the tool tips are transmitted through the sensor only and back to the supporting structure at the other end of the sensor, or the "ground", therefore ensuring all tool-tips loads are gathered by the sensor before sending back the force and moment signals back to the controller for interpretation.

FIG. 26e shows a cross-section through the load path of the end-effector 428. The grounded portion consists of the base block 605 that supports the backend of the force-moment sensor 608 only. All of the actuators 600 and 601, the tool-actuation sensor 604, and their corresponding supporting structure are mounted to the front face of the sensor 608 free end. This excess weight read by the sensor 608 can be offset by zeroing out the signal at the controller with the known weights and center-of-gravity distances of each part contributing to the weight measured by the sensor 608, including those of the tool 430. This active gravity compensation technique can be completed by computing the expected dead weight of all parts at the sensor location with the dynamic equations of the manipulator, minus which the filtered signal from the sensor is the pure external forces and moments acting at the tool tips.

Besides tool-tips forces and moments, haptic feedback also includes the tool-actuation force feedback. Referring to FIG. 26d, the closing and opening of the blades 506 and 508 of the tool 430 is achieved by the vertical motion of the piston 504. The piston 504 is carried by the actuator subassembly 452, which is connected back to the tool-actuation motor 601 via the actuation bar 603. The pinch force at the tool tips of the blades 506 and 508, therefore, is transmitted vertically through the above mentioned path. Thus a strain-gauge type sensor 604 is located at middle of the cantilever section of the actuation bar 603 to measure the elastic deformation of the bar 603 to provide tool-actuation force feedback to the controller. The voltage signal generated can be used in force regulation for tool-actuation, or can be reproduced at the hand-controller for tool-actuation haptic feedback via an appropriate human-machine interface.

Figure 30:
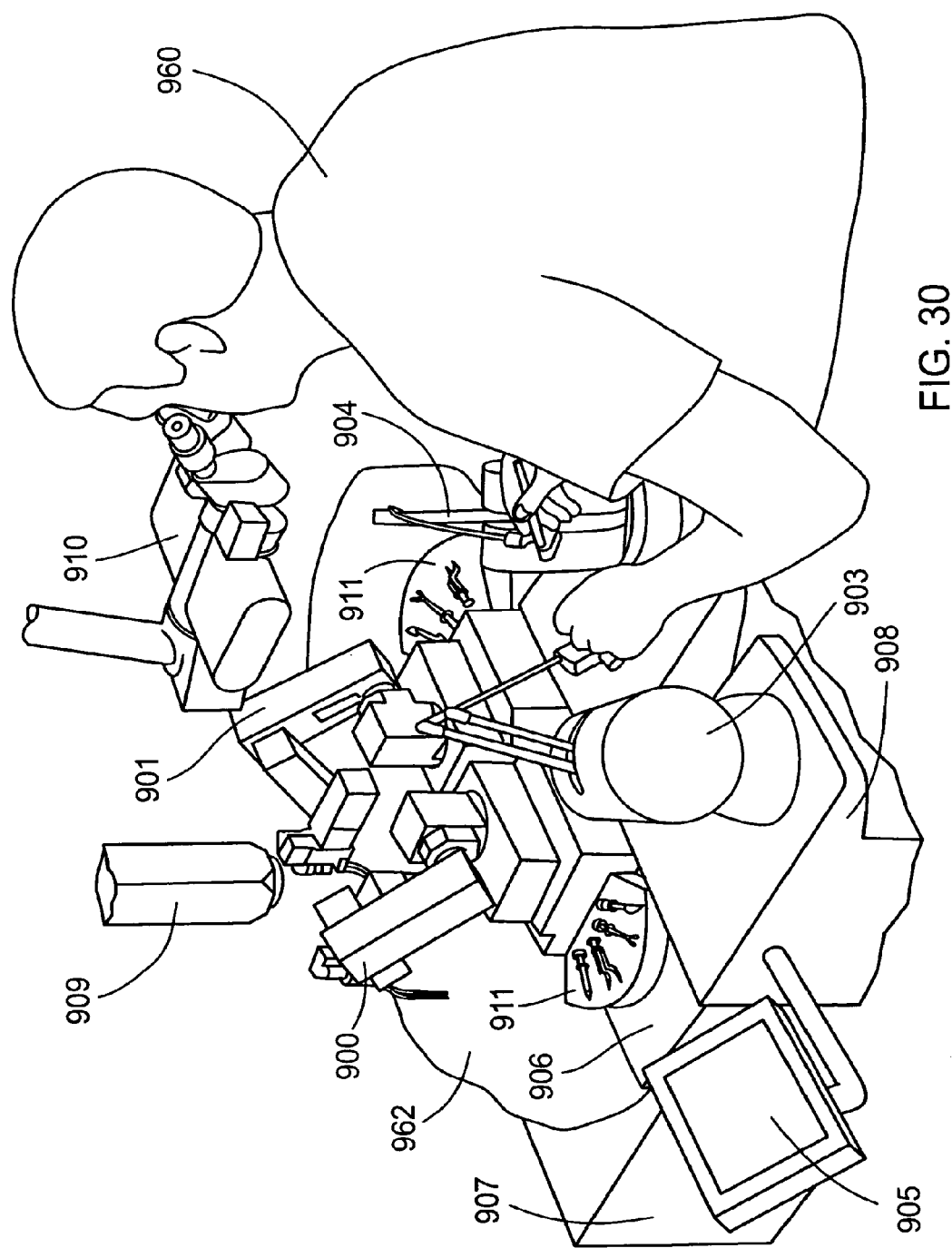
FIG. 30 is a schematic diagram showing the operation concept of a dual-manipulator telerobotic system controlled by a surgeon in a typical operating theatre.

Referring to FIG. 16a, surgical manipulator 400 is designed to be used for surgical operations in a telerobotic system under the direct control of a surgeon 960. In a telerobotic system, a robot and a hand-controller form a master-slave relationship as the operator moves the hand-controller, or the master, to perform the action, and the robot, or the slave, carries out the actual operation as the output by following the hand motions of the operator. Referring to FIG. 30, the telerobotic system is comprised of two portions, the slave which is a mobile platform 906 containing two manipulators 900 and 901, and the master in the form of a workstation 908 including one or more computer monitor, and two haptic devices 903, 904 as hand-controllers, with each manipulator-hand-controller pair mimicking the left and right arm of a surgeon 960 such that dual-hand operation is possible.

The two manipulators 900 and 901 have mirrored configurations to each other, with all components being identical. Thus the surgical manipulator system includes at least two surgical manipulators 900 and 901 configured to be structural mirror images of each other, with one of the surgical manipulator being configured for left handed operation and the other being configured for right handed operation. This configuration is advantageous in that it allows the surgical tools attached to respective end-effectors to be brought into closest proximity with each other in a surgical site on a patient.

There is a communication system coupling the left and right hand-controllers to their respective surgical manipulators for translating movement of the left and right hand-controllers to scaled movement of the first and second surgical manipulators. This scaled motion may be predetermined in software and may be 1:1 in which the move of the surgeons hand on the controller is translated into exactly the same movement of the end-effector. However the ratio need not be 1:1 depending on the surgical procedure involved.

For each of the manipulators 900 and 901, there is a tool tray 911 located near the base of each manipulator. The tool tray 911 holds a number of surgical tools which may or may not be identical to the tools shown in FIGS. 22a to 25b, but are required for the planned surgical procedures. The manipulators 900 and 901 are programmed to change tools automatically at the tool tray 911 upon a single command from the surgeon 960. Both manipulators 900 and 901 are mounted on the mobile platform 906 which can easily be transported to dock with the operating table 907 and undock and remove when the operation is completed. A microscope and/or stereo camera 909, which can be mounted either on the mobile platform 906 or as a fixture in the operating room, provides visual display of the surgical site and/or the overview of the manipulators plus their tools with respect to the patient 962.

A single cable connection using regular network protocol may be used for communication of signals between the manipulators mobile platform 906 and the workstation 908 at which the surgeon 960 is at. The left hand-controller 903 by default controls the left manipulator 900, and the right hand-controller controls the right manipulator 901, although through software selection the surgeon 960 can switch over the communication linkage between the pair if it is required during the operation.

Each of the haptic devices 903 and 904 is a 6DOF hand-controller that can measure a surgeon's hand motion in all six directions of translation and rotation in 3D space. The motion signals are then sent to the intended manipulator through the motion controller, at which the surgeon's input will be reproduced. These signals can also be scaled, such that the surgeon 960 can fully utilize the best resolution of the manipulators motion by having their hand motions at the hand-controllers 903 and 904 scaled down before being carried out by the manipulators. At the hand-controllers 903 and 904, switches are available for the surgeon 960 to control other functions of the manipulators, such as tool-actuation, dead-man switch, and automatic tool changing.

The hand-controllers 903 and 904 also have three to six powered joints to provide haptic feedback to the surgeon 960. The base positions of the hand-controllers 903 and 904 on the workstation 908 can be adjusted to the comfort of the surgeon 960, and with the addition of arm rests the only motion required from the surgeon 960 is at the wrists. Since there is no absolute referencing of the hand-controller motion with respect to that of the manipulators, the surgeon 960 can hold the handles of the hand-controllers 903 and 904 at a comfortable posture, again to minimize fatigue, while the manipulators 900 and 901 are holding the surgical tools in the appropriate positions. Also on the workstation 908, there is one or more computer monitor 905 displaying system status and also providing touch-screen interface to the surgeon 960 and/or nurses for adjusting critical system parameters.

One of the most important settings the surgeon 960 needs to make is the virtual boundaries for the manipulators. Using a preoperative image with registration back to the manipulator, or with a real-time intraoperative image taken by the camera 909, the surgeon 960 can specify on-screen the region at the surgical site where the manipulator with the surgical tool 430 can operate within. If the surgeon 960 commanded the manipulator via the hand-controllers to move near these boundaries, the motion controller will automatically stop the manipulators from moving any further unless the surgeon 960 reverse the motion. This will set a prohibited area where the manipulators cannot move the surgical tools to, such that the surgeon 960 can ensure critical areas in the patient's anatomy is protected. The monitor 905 also displays the real-time video taken by the microscope and/or camera 909.

Alternatively, the microscope/camera 909 video signal can be displayed via a digital eyepiece 910 which mimics that of a conventional microscope if the surgeon 960 prefers. The surgeon 960 together with the workstation 908 can be immediately next to the operating table 907 for telepresence operation, where the surgeon 960 will directly observe the surgical site on the patient 962 without any visual aid. In the case of remote operation, the surgeon 960 and the workstation 908 is at a physical distance from the operating table 907 limited only by the network connection infrastructure available. Visual feedback via the monitor 905 and haptic feedback via the hand-controllers 903 and 904 retain the senses of vision and touch of the surgeon 960 over the physical distance, which makes remote teleoperation possible with the additional benefits of finer and more consistent hand motion, more ergonomic user-interfaces to reduce surgeon 960 fatigue, less intrusive to the surgical theatre, and built-in fail-safe features to protect the patient 962 and the surgeon 960.

Besides teleoperation, the manipulators can also be operated using pre-planned image-guided trajectories. Pre-operative images of the patient's surgical site are taken with an external imager, such as fluoroscope or CT-scanner. The surgeon 960 can then use those images to define where the problem exists, which area the manipulator needs to go to and with which surgical tool. The surgeon 960 can then take an intra-operative image with registration to the manipulator coordinate system, and map it to the pre-operative image with the planned targets. The control software will then interpret the targets into workspace coordinates of the manipulators, thereby allowing the surgeon 960 to specify the complete trajectories of the surgical tool held by the manipulator with respect to the surgical site of the patient 962. Upon execution of the pre-planned trajectories, the surgeon 960 can either start the autonomous motion of the manipulator and pause or rewind at any time at the workstation monitor, or use the hand-controller to control the motion along the prescribed trajectories.

Comparing to the other devices available in the current market, the surgical manipulator described herein has several advantages in the field of microsurgeries, including brain, spine and eye surgery. First of all, this surgical manipulator is smaller than a regular human arm thanks to the right-angle transmission modules and the compactness of the other actuation components, which allows easy access to the surgical site and minimizes intrusion to the operating room. Although being compact in size, this manipulator has broad enough motion range and reach to accomplish tasks requiring bigger manipulator workspace such as suturing. The 6DOF available means dexterous motion is capable in any given direction. With high-power brushless servo motors deployed at each joint, relatively heavier-duty tasks such as tissue-retraction and bone-drilling for pedicle screw is made possible. The smallest step size achievable at the tool tip, due to the use of the right-angle transmission modules as well as high resolution sensors, amplifiers and motion controllers, matches the finger motion resolution of the best brain surgeons. The auto tool-changing capability as a result of the end-effector design reduces the tool-changing time and also human-error. The end-effector structure forces the load-path to go through the force-moment, and the consequent high fidelity of haptic feedback retains the sense of touch of the surgeon, without which the surgeon would lose a significant amount of surgical techniques and know-how.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES

Foothill Hospital—neuroArm
7237626: Microsurgical robot system; 2006 Dec. 26
20070032906: Microsurgical robot system; 2007 Feb. 8
Intuitive Surgical—di Vinci
7,121,781; Surgical instrument with a universal wrist; 2006 Oct. 17
7,107,090: Devices and methods for presenting and regulating auxiliary information on an image display of a telesurgical system to assist an operator in performing a surgical procedure; 2006 Sep. 12
7,087,049: Repositioning and reorientation of master/slave relationship in minimally invasive telesurgery; 2006 Aug. 8
7,083,571: Medical robotic arm that is attached to an operating table; 2006 Aug. 1
7,074,179: Method and apparatus for performing minimally invasive cardiac procedures; 2006 Jul. 11
7,066,926: Platform link wrist mechanism; 2006 Jun. 27
7,048,745: Surgical robotic tools, data architecture, and use; 2006 May 23
6,994,708: Robotic tool with monopolar electro-surgical scissors; 2006 Feb. 7
6,991,627: Articulated surgical instrument for performing minimally invasive surgery with enhanced dexterity and sensitivity; 2006 Jan. 31
6,951,535: Tele-medicine system that transmits an entire state of a subsystem; 2005 Oct. 4
6,936,042: Surgical tools for use in minimally invasive telesurgical applications; 2005 Aug. 30
6,933,695: Ceiling and floor mounted surgical robot set-up arms; 2005 Aug. 23
6,905,491: Apparatus for performing minimally invasive cardiac procedures with a robotic arm that has a passive joint and system which can decouple the robotic arm from the input device; 2005 Jun. 14
6,905,460: Method and apparatus for performing minimally invasive surgical procedures; 2005 Jun. 14
6,902,560: Roll-pitch-roll surgical tool; 2005 Jun. 7
6,879,880: Grip strength with tactile feedback for robotic surgery; 2005 Apr. 12
6,871,117: Modularity system for computer assisted surgery; 2005 Mar. 22
6,866,671: Surgical robotic tools, data architecture, and use; 2005 Mar. 15
6,840,938: Bipolar cauterizing instrument; 2005 Jan. 11
6,837,883: Arm cart for telerobotic surgical system; 2005 Jan. 4
6,788,018: Ceiling and floor mounted surgical robot set-up arms; 2004 Sep. 7
6,783,524: Robotic surgical tool with ultrasound cauterizing and cutting instrument; 2004 Aug. 31
6,770,081: In vivo accessories for minimally invasive robotic surgery and methods; 2004 Aug. 3
6,766,204: Alignment of master and slave in a minimally invasive surgical apparatus; 2004 Jul. 20
6,746,443: Roll-pitch-roll surgical tool; 2004 Jun. 8
6,699,235: Platform link wrist mechanism; 2004 Mar. 2
6,685,698: Roll-pitch-roll surgical tool; 2004 Feb. 3
6,676,684: Roll-pitch-roll-yaw surgical tool; 2004 Jan. 13
6,659,939: Cooperative minimally invasive telesurgical system; 2003 Dec. 9
6,645,196: Guided tool change; 2003 Nov. 11
6,594,552: Grip strength with tactile feedback for robotic surgery; 2003 Jul. 15
6,491,701: Mechanical actuator interface system for robotic surgical tools: 2002 Dec. 10
6,459,926: Repositioning and reorientation of master/slave relationship in minimally invasive telesurgery; 2002 Oct. 1
6,441,577: Manipulator positioning linkage for robotic surgery; 2002 Aug. 27
6,394,998: Surgical tools for use in minimally invasive telesurgical applications; 2002 May 28
6,371,952: Articulated surgical instrument for performing minimally invasive surgery with enhanced dexterity and sensitivity; 2002 Apr. 16
6,364,888: Alignment of master and slave in a minimally invasive surgical apparatus; 2002 Apr. 2
6,346,072: Multi-component telepresence system and method; 2002 Feb. 12
6,331,181: Surgical robotic tools, data architecture, and use; 2001 Dec. 18
6,312,435: Surgical instrument with extended reach for use in minimally invasive surgery; 2001 Nov. 6
6,309,397: Accessories for minimally invasive robotic surgery and methods; 2001 Oct. 30
D444,555: Interface for a medical instrument; 2001 Jul. 3
6,246,200: Manipulator positioning linkage for robotic surgery; 2001 Jun. 12
D441,862: Portion of an interface for a medical instrument; 2001 May 8
D441,076: Adaptor for a medical instrument; 2001 Apr. 24
6,206,903: Surgical tool with mechanical advantage; 2001 Mar. 27
D438,617: Portion of an adaptor for a medical instrument; 2001 Mar. 6
6,132,368: Multi-component telepresence system and method; 2000 Oct. 17
5,807,377: Force-reflecting surgical instrument and positioning mechanism for performing minimally invasive surgery with enhanced dexterity and sensitivity; 1998 Sep. 15
5,797,900: Wrist mechanism for surgical instrument for performing minimally invasive surgery with enhanced dexterity and sensitivity; 1998 Aug. 25
5,792,135: Articulated surgical instrument for performing minimally invasive surgery with enhanced dexterity and sensitivity; 1998 Aug. 11
Computer Motion (Intuitive) $_iV$ Zeus, AESOP
06804581: Automated endoscope system optimal positioning; 2004 Oct. 12,
(05907664) 1999 May 25, (05878193) 1999 Mar. 2, (05841950) 1998 Nov. 24,
(05815640) 1998 Sep. 29, (05754741) 1998 May 19, (05657429) 1997 Aug. 12, (05553198) 1996 Sep. 3, (05515478) 1996 May 7,
06132441: Rigidly-linked articulating wrist with decoupled motion transmission; 2000 Oct. 17
06892112: Modularity system for computer assisted surgery; 2005 May 10,
(06871117) 2005 Mar. 22, (06836703) 2004 Dec. 28, (06799088) 2004 Sep. 28,
(06785593) 2004 Aug. 31, (06728599) 2004 Apr. 27
06839612: Microwrist system for surgical procedures; 2005 Jan. 4

06905491: Apparatus for performing minimally invasive cardiac procedures with a robotic arm that has a passive joint and system which can decouple the robotic arm from the input device; 2005 Jun. 14
20040186345_6: Medical robot arm that is attached to an operating table; 2004 Sep. 23
JPL (MicroDexterity)—RAMS & Others
5784542: Decoupled six degree-of-freedom teleoperated robot system; 1998 Jul. 21
5710870: Decoupled six degree-of-freedom robot manipulator; 1998 Jan. 20
6676669: Surgical manipulator; 2004 Jan. 13
6702805: Manipulator; 2004 Mar. 9
MAKO—HGS
WO/2006/091494, PCT/US2006/005700: Haptic guidance system and method; 2006 Aug. 31
20060142657: Haptic guidance system and method; 2006 Jun. 29
07206627: System and method for intra-operative haptic planning of a medical procedure; 2007 Apr. 17
Mazor—SpineAssist
6837892: Miniature bone-mounted surgical robot; 2005 Jan. 4
Integrated Surgical—Robodoc
5769092: Computer-aided system for revision total hip replacement surgery; 1998 Jun. 23
5976122: Articulated surgical instrument for performing minimally invasive surgery with enhanced dexterity and sensitivity; 1999 Nov. 2
ArmStrong (Prosurgics)—PathFinder
20040142803: Tool holder arrangement; 2004 Jul. 22
05766126: Goniometric robotic arrangement; 1998 Jun. 16
06349245: Method of and apparatus for registration of a robot; 2002 Feb. 19
Endovia (Hansen)—Laprotek
20040176751: Robotic Medical Instrument System; 2004 Sep. 9
6843793: Surgical Instrument; 2005 Jan. 18
6810281: Medical mapping system; 2004 Oct. 26
6860878: Interchangeable instrument; 2005 Mar. 1
6692485: Articulated apparatus for telemanipulator system; 2004 Feb. 17
6554844: Surgical instrument; 2003 Apr. 29
Cable Drive References:
4903536: Compact cable transmission with cable differential; 1990 Feb. 27
5046375: Compact Cable Transmission with Cable Differential; 1991 Sep. 10
5207114: Compact Cable Transmission with Cable Differential; 1993 May 4
5388480: Pretensioning mechanism for tension element drive systems; 1995 Feb. 14
5269728: Differential drive; 1993 Dec. 14
7281447: Articulated mechanism comprising a cable reduction gear for use in a robot arm; 2007 Oct. 16
5429015: Two degree of freedom robotic manipulator constructed from rotary drives; 1995 Jul. 4
5553509: Three degree of freedom robotic manipulator constructed from rotary drives; 1996 Sep. 10

Therefore what is claimed is:

1. A surgical manipulator comprising:
   i) a serially jointed surgical manipulator arm, comprising;
      three or more consecutively coupled right-angle drive mechanisms;
      each right-angle drive mechanism including
         an input pulley having an input axis and an output pulley having an output axis, said input axis being perpendicular and intersecting with said input axis, and including a bi-directional coupling mechanism for coupling said input pulley and said output pulley; and
         a motor drive unit directly coupled to said input pulley for rotating said input pulley about said input axis wherein rotation of said input pulley is translated into rotation of said output pulley by said bi-directional coupling mechanism about said output axis;
   ii) a robotic wrist mounted on a last of said three or more consecutively coupled right-angle drive mechanisms so that when said last of said three or more consecutively coupled right-angle drive mechanisms output pulley is rotated, said robotic wrist rotates about said last mechanisms output axis, said robotic wrist including a wrist output shaft and a wrist-roll axis; and
   iii) an end-effector mounted to said wrist output shaft, said end-effector including gripping means for releasibly gripping a surgical tool wherein said end-effector is rotatable about said wrist-roll axis;
   wherein said end-effector includes
   a) an assembly including an interface configured to be attached to said serially jointed surgical manipulator arm, a tool-yaw motor, a tool-actuation motor;
   b) a magnetic tool holder mounted to said assembly and being detachable therefrom, said magnetic tool holder being configured to automatically engage and release a surgical tool;
   c) a tool-actuation mechanism mounted to said assembly and being detachable therefrom, said tool-actuation mechanism being configured to automatically engage and release a piston on the surgical tool, said tool-actuation mechanism being coupled to said tool-actuation motor; and
   d) a tool-yaw drive mechanism mounted to said assembly and being detachable therefrom, said tool-yaw drive mechanism being coupled to said tool-yaw motor, wherein upon activation of said tool-yaw drive mechanism the surgical tool engaged by said magnetic tool holder rotates about a tool-yaw axis and wherein upon activation of said tool-actuation mechanism the piston of the engaged surgical tool is linearly retracted or linearly extended with respect to said end-effector thereby activating a tool portion of the surgical tool.

2. The surgical manipulator according to claim 1 wherein said interface includes a base block which interfaces to a wrist of a robotic arm, including a motor-support bracket on which the tool-actuation motor and the tool-yaw motor are mounted, and wherein said assembly includes a tool-tip force-moment sensor which is a single mechanical linkage between said motor-support bracket and said base block.

3. The surgical manipulator according to claim 1 wherein said tool-actuation motor is a linear actuator having an output shaft which moves up and down along a major axis of said tool-actuation motor and, at a distal end portion of said output shaft, an actuator bar is connected at a first end portion thereof, said actuator bar having a second end portion supported by a vertical guide rod and including an interface which couples to said tool-actuation mechanism, wherein said actuator bar transmits vertical motion of said output shaft to said tool-actuation mechanism which is mounted at said second end of the bar such that said vertical motion provides a tool-actuation axis of motion for said end-effector.

4. The surgical manipulator according to claim 3 including a tool-actuation force sensor mounted on said actuator bar between a point where said actuator bar is supported by said vertical guide rod and said interface with the tool-actuation mechanism.

5. The surgical manipulator according to claim 4 wherein said tool-actuation force sensor is a strain gauge, at which point on the bar on which said force sensor is mounted, any elastic vertical deflection due to actuation of the surgical tool can be measured.

6. The surgical manipulator according to claim 1 wherein said tool-yaw mechanism includes a frame, on which is mounted a pair of idler pulleys, a middle idler pulley and a drive pulley, including a toothed belt being routed on said idler pulleys, said middle idler pulley and said drive pulley, said toothed belt being configured to engage a toothed pulley on the surgical tool, on two opposite ends of a diameter of said toothed pulley, and wherein bi-directional rotation of the toothed belt driven by said drive pulley converts tangential forces to rotary motion of the surgical tool.

7. The surgical manipulator according to claim 6 wherein said frame has an open front-framed architecture and a toothed belt routing configuration on said idler pulleys and said middle idler pulley configured to allow the surgical tool to be ejected/replaced from said end-effector.

8. The surgical manipulator according to claim 1 wherein said magnetic tool holder, said tool-actuation mechanism, and said tool-yaw mechanism are sterile subassemblies, with quick release and attachment features for quickly attaching and detaching them to and from said assembly.

9. The surgical manipulator according to claim 1 wherein, when in operation, said end-effector is coupled to a robotic wrist, which is connected to a robotic lower arm, which is connected to a robotic fore arm, which is connected to a surgical manipulator base, and wherein said assembly, said tool-yaw mechanism and said tool-actuation mechanism, are encapsulated in a protective drape bag which covers from the base of the surgical manipulator all the way through the entire length of the robotic fore arm, the robotic lower arm and the robotic wrist and up to a front face of said assembly.

10. The surgical manipulator according to claim 1 wherein said surgical manipulator is a first surgical manipulator, including at least a second surgical manipulator and wherein said first surgical manipulator and said at least a second surgical manipulator are configured to be structural mirror images of each other, said first surgical manipulator being configured for left handed operation and said at least a second surgical manipulator being configured for right handed operation to allow the surgical tools attached to respective end-effectors to be brought into proximity with each other in a surgical site on a patient.

11. The surgical manipulator according to claim 1 wherein said at least first, second and third right-angle drive mechanisms each include
  a) a housing and wherein said first drive mechanism includes a harmonic drive mounted on said housing being connected to said input pulley for rotation about said input axis;
  b) an output drive shaft having an output axis of rotation, said output shaft being connected to said output pulley, said output pulley being mounted in said housing for rotation about said output axis, said input and output pulleys being mounted in said housing and positioned with respect to each other such that said input axis is perpendicular to, and intersecting with said output axis;
  c) said bi-directional coupling mechanism for coupling said first input pulley and said first output pulley comprising
    a cable drive mounted in said housing, said cable drive including,
    at least one flexible cable, said input and output pulleys each including at least one cable guide for receiving therein said at least one flexible cable,
    idler means for guiding said at least one flexible cable between said input and output pulleys,
  wherein when the input pulley rotates in one direction about said input axis, said at least one flexible cable pulls the output pulley and output shaft to rotate in one direction about said output axis of rotation, and when the input pulley rotates in the other direction about said input axis, said at least one flexible cable pulls the output pulley and output shaft to rotate in an opposite direction about said output axis.

12. The surgical manipulator according to claim 10 incorporated into a surgical manipulator system, the surgical manipulator system comprising:
  a) left and right hand controllers with the right hand controller being associated with the first surgical manipulator and the left hand controller being associated with the second surgical manipulator, said at least first and second hand controllers being configured to be operated by a surgeon; and
  b) communication system coupling said left and right hand controllers to said at least first and second surgical manipulators for translating movement of said left and right hand controllers to scaled movement of said at least first and second surgical manipulators.

13. The surgical manipulator system according to claim 12 including a vision system focused on a work area including an area of a patient to be operated on and focused on the end-effectors and associated surgical tools attached to said at least two surgical manipulators, said vision system including display means for displaying images of said work area to a surgeon.

14. The surgical manipulator system according to claim 13 configured for teleoperation wherein said surgeon is located remotely from said patient.

15. The surgical manipulator system according to claim 12 wherein said end-effector includes a tool-tip force-moment sensor mounted to said end-effector and configured to sense tool tip force and moment at a tip of the surgical tool, and wherein said end-effector includes a tool-actuation force sensor mounted thereon configured to measure actuation forces on a tip of the surgical tool, and wherein said communication system coupling said left and right hand controllers to said at least first and second surgical manipulators is configured to communicate said forces and moments to said left and right handed controllers providing haptic feedback to said surgeon.

16. The surgical manipulator system according to claim 15 wherein said tool-actuation force sensor is a strain gauge.

* * * * *